(12) United States Patent
Shelton et al.

(10) Patent No.: US 11,008,375 B2
(45) Date of Patent: *May 18, 2021

(54) GIP-GLP-1 DUAL AGONIST COMPOUNDS AND METHODS

(71) Applicant: Zealand Pharma A/S, Glostrup (DK)

(72) Inventors: Anne Pernille Tofteng Shelton, Glostrup (DK); Pia Nørregaard, Glostrup (DK); Jacob Ulrik Fog, Glostrup (DK); Carsten Boye Knudsen, Glostrup (DK)

(73) Assignee: Zealand Pharma A/S, Søborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/112,926

(22) Filed: Aug. 27, 2018

(65) Prior Publication Data

US 2019/0218270 A1 Jul. 18, 2019

Related U.S. Application Data

(63) Continuation of application No. 15/034,778, filed as application No. PCT/EP2014/073970 on Nov. 6, 2014, now Pat. No. 10,093,713.

(30) Foreign Application Priority Data

Nov. 6, 2013 (EP) .................................... 13191843
Jul. 14, 2014 (EP) .................................... 14176878

(51) Int. Cl.
*C07K 14/645* (2006.01)
*C07K 14/605* (2006.01)
*A61K 38/00* (2006.01)

(52) U.S. Cl.
CPC .......... *C07K 14/645* (2013.01); *C07K 14/605* (2013.01); *A61K 38/00* (2013.01)

(58) Field of Classification Search
CPC .... A61K 38/00; C07K 14/605; C07K 14/645; A61P 11/00; A61P 19/08; A61P 19/10; A61P 1/16; A61P 29/00; A61P 3/00; A61P 3/04; A61P 3/06; A61P 3/10; A61P 7/02; A61P 9/00; A61P 9/10; A61P 9/12

See application file for complete search history.

(56) References Cited

U.S. PATENT DOCUMENTS

| | | | |
|---|---|---|---|
| 4,288,627 A | 9/1981 | Kubicek |
| 5,118,666 A | 6/1992 | Habener |
| 5,120,712 A | 6/1992 | Habener |
| 5,424,286 A | 6/1995 | Eng |
| 5,512,549 A | 4/1996 | Chen et al. |
| 5,523,449 A | 6/1996 | Prasad et al. |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,795,861 A | 8/1998 | Kolterman et al. |
| 5,846,747 A | 12/1998 | Thorens et al. |
| 5,846,937 A | 12/1998 | Drucker |
| 6,006,753 A | 12/1999 | Efendic |
| 6,051,689 A | 4/2000 | Thorens |
| 6,110,703 A | 8/2000 | Egel-Mitani et al. |
| 6,114,304 A | 9/2000 | Kolterman et al. |
| 6,136,784 A | 10/2000 | L'Italien et al. |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,410,511 B2 | 6/2002 | L'Italien et al. |
| 6,451,974 B1 | 9/2002 | Hansen |
| 6,458,924 B2 | 10/2002 | Knudsen et al. |
| 6,506,724 B1 | 1/2003 | Hiles et al. |
| 6,528,486 B1 | 3/2003 | Larsen et al. |
| 6,703,359 B1 | 3/2004 | Young et al. |
| 6,767,887 B1 | 7/2004 | Hoffmann et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 7,056,734 B1 | 6/2006 | Egan et al. |
| 7,115,569 B2 | 10/2006 | Beeley et al. |

(Continued)

FOREIGN PATENT DOCUMENTS

| AU | 3247799 A | 9/1999 |
|---|---|---|
| AU | 2008326324 A1 | 5/2009 |

(Continued)

OTHER PUBLICATIONS

U.S. Appl. No. 14/116,268, Just et al.
U.S. Appl. No. 14/516,216, filed Apr. 23, 2015, Riber et al.
U.S. Appl. No. 14/517,497, filed Apr. 23, 2015, Riber et al.
U.S. Appl. No. 14/843,047, filed May 5, 2016, Zealand Pharma A/S.
U.S. Appl. No. 60/132,018, Prickett et al.
U.S. Appl. No. 61/784,294, Tolborg et al.
Abbrecht et al., "Erythrocyte life-span in mice acclimatized to different degrees of hypoxia," J Appl Physiol. 32(4):443-445 (1972).
Action Closing Prosecution in Inter Partes Reexam 95/000,276, mailed Mar. 17, 2011 (25 pages).
Adelhorst et al., "Structure-activity studies of glucagon-like peptide-1," J Biol Chem 269(9):6275-6278 (1994).

(Continued)

*Primary Examiner* — Marcela M Cordero Garcia
(74) *Attorney, Agent, or Firm* — Clark & Elbing LLP

(57) ABSTRACT

The present invention relates to acylated GIP analogues which have dual GIP and GLP-1 activity, and their use in the treatment of metabolic disorders.

6 Claims, 6 Drawing Sheets

Specification includes a Sequence Listing.

(56) References Cited

U.S. PATENT DOCUMENTS

| | | |
|---|---|---|
| 7,138,375 B2 | 11/2006 | Beeley et al. |
| 7,153,825 B2 | 12/2006 | Young et al. |
| 7,157,555 B1 | 1/2007 | Beeley et al. |
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |
| 7,348,404 B2 | 3/2008 | Holm et al. |
| 7,399,489 B2 | 7/2008 | Kolterman et al. |
| 7,407,932 B2 | 8/2008 | Young et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,741,269 B2 | 6/2010 | Young et al. |
| 7,803,766 B2 | 9/2010 | Cruz |
| 7,858,740 B2 | 12/2010 | Beeley et al. |
| 7,928,065 B2 | 4/2011 | Young et al. |
| 7,935,786 B2 | 5/2011 | Larsen |
| 7,994,122 B2 | 8/2011 | Riber et al. |
| 8,026,210 B2 | 9/2011 | Young et al. |
| 8,057,822 B2 | 11/2011 | Prickett et al. |
| 8,097,698 B2 | 1/2012 | Knudsen et al. |
| 8,263,550 B2 | 9/2012 | Beeley et al. |
| 8,288,338 B2 | 10/2012 | Young et al. |
| 8,445,647 B2 | 5/2013 | Prickett et al. |
| 8,642,540 B2 | 2/2014 | Meier et al. |
| 8,642,541 B2 | 2/2014 | Meier et al. |
| 8,642,727 B2 | 2/2014 | Larsen et al. |
| 8,680,049 B2 | 3/2014 | Meier et al. |
| 8,685,919 B2 | 4/2014 | Meier et al. |
| RE45,313 E | 12/2014 | Larsen et al. |
| 9,089,538 B2 | 7/2015 | Neerup et al. |
| 9,156,901 B2 | 10/2015 | Riber et al. |
| 9,169,310 B2 | 10/2015 | Riber et al. |
| 9,180,169 B2 | 11/2015 | Tolborg et al. |
| 9,259,477 B2 | 2/2016 | Tolborg et al. |
| 9,403,894 B2 | 8/2016 | Meier et al. |
| 9,453,064 B2 | 9/2016 | Just et al. |
| 9,649,362 B2 | 5/2017 | Neerup et al. |
| 9,750,788 B2 | 9/2017 | Kadereit et al. |
| 9,790,262 B2 | 10/2017 | Shandler et al. |
| 9,896,495 B2 | 2/2018 | Riber et al. |
| 9,969,787 B2 | 5/2018 | Just et al. |
| 9,975,939 B2 | 5/2018 | Tolborg et al. |
| 9,988,429 B2 | 6/2018 | Riber et al. |
| 10,004,786 B2 | 6/2018 | Riber et al. |
| 10,093,713 B2 * | 10/2018 | Shelton ................ C07K 14/605 |
| 10,100,097 B2 * | 10/2018 | Just ..................... C07K 14/605 |
| 10,131,702 B2 | 11/2018 | Just et al. |
| 10,253,078 B2 * | 4/2019 | Shelton ..................... A61P 9/12 |
| 2002/0137666 A1 | 9/2002 | Beeley et al. |
| 2004/0106547 A1 | 6/2004 | Larsen et al. |
| 2005/0070469 A1 | 3/2005 | Bloom et al. |
| 2006/0057137 A1 | 3/2006 | Steiness |
| 2006/0194719 A1 | 8/2006 | Ebbehoj et al. |
| 2006/0293232 A1 | 12/2006 | Levy et al. |
| 2007/0111940 A1 | 5/2007 | Larsen et al. |
| 2009/0088369 A1 | 4/2009 | Steiness |
| 2010/0099601 A1 | 4/2010 | Weiss |
| 2010/0190701 A1 | 7/2010 | Day et al. |
| 2010/0240883 A1 | 9/2010 | Wu et al. |
| 2011/0144008 A1 | 6/2011 | Larsen et al. |
| 2011/0230397 A1 | 9/2011 | Carriero et al. |
| 2011/0245165 A1 | 10/2011 | Larsen et al. |
| 2011/0286981 A1 | 11/2011 | Meier et al. |
| 2011/0286982 A1 | 11/2011 | Meier et al. |
| 2011/0293586 A1 | 12/2011 | Meier et al. |
| 2011/0293587 A1 | 12/2011 | Meier et al. |
| 2011/0312878 A1 | 12/2011 | Larsen |
| 2012/0178670 A1 | 7/2012 | Riber et al. |
| 2013/0053304 A1 | 2/2013 | Wang et al. |
| 2013/0143793 A1 | 6/2013 | Neerup et al. |
| 2013/0157929 A1 | 6/2013 | Riber et al. |
| 2013/0157935 A1 | 6/2013 | Meier et al. |
| 2013/0157953 A1 | 6/2013 | Petersen et al. |
| 2013/0210722 A1 | 8/2013 | Larsen et al. |
| 2013/0316941 A1 | 11/2013 | Hamprecht et al. |
| 2014/0011733 A1 | 1/2014 | Fosgerau et al. |
| 2014/0080757 A1 | 3/2014 | Tolborg et al. |
| 2014/0127174 A1 | 5/2014 | Meier et al. |
| 2014/0127175 A1 | 5/2014 | Meier et al. |
| 2014/0187483 A1 | 7/2014 | Steiness |
| 2014/0336107 A1 | 11/2014 | Tolborg et al. |
| 2014/0336356 A1 | 11/2014 | Larsen et al. |
| 2015/0080295 A1 | 3/2015 | Meier et al. |
| 2015/0111817 A1 | 4/2015 | Riber et al. |
| 2015/0111826 A1 | 4/2015 | Riber et al. |
| 2015/0210744 A1 | 7/2015 | Riber et al. |
| 2015/0299281 A1 | 10/2015 | Just et al. |
| 2015/0322130 A1 | 11/2015 | DiMarchi et al. |
| 2015/0376257 A1 | 12/2015 | Riber et al. |
| 2016/0000883 A1 | 1/2016 | Fosgerau et al. |
| 2016/0009777 A1 | 1/2016 | Tolborg et al. |
| 2016/0082118 A1 | 3/2016 | Tolborg et al. |
| 2016/0120951 A1 | 5/2016 | Riber et al. |
| 2016/0184400 A1 | 6/2016 | Neerup et al. |
| 2016/0257729 A1 | 9/2016 | Just et al. |
| 2016/0304576 A1 | 10/2016 | Meier et al. |
| 2016/0347813 A1 | 12/2016 | Hamprecht et al. |
| 2017/0107267 A1 | 4/2017 | Larsen et al. |
| 2018/0141990 A1 | 5/2018 | Riber et al. |

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 1076066 A1 | 2/2001 |
| EP | 1196444 B1 | 6/2003 |
| EP | 1329458 A2 | 7/2003 |
| EP | 1421950 A1 | 5/2004 |
| EP | 2025684 A1 | 2/2009 |
| EP | 2028192 A1 | 2/2009 |
| EP | 1525219 B1 | 5/2009 |
| EP | 2112161 A2 | 10/2009 |
| JP | H07504670 A | 5/1995 |
| JP | 2001011095 A | 1/2001 |
| JP | 2007-524584 A | 8/2007 |
| JP | 2007-525495 A | 9/2007 |
| JP | 2011-524418 A | 9/2011 |
| JP | 2012-511900 A | 5/2012 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-97/46584 A1 | 12/1997 |
| WO | WO-98/05351 A1 | 2/1998 |
| WO | WO-98/08531 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |
| WO | WO-98/50351 A1 | 11/1998 |
| WO | WO-99/07404 A1 | 2/1999 |
| WO | WO-99/25727 A2 | 5/1999 |
| WO | WO-99/25728 A1 | 5/1999 |
| WO | WO-99/40788 A1 | 8/1999 |
| WO | WO-99/43707 A1 | 9/1999 |

(56) References Cited

FOREIGN PATENT DOCUMENTS

| | | |
|---|---|---|
| WO | WO-99/43708 A1 | 9/1999 |
| WO | WO-99/46283 A1 | 9/1999 |
| WO | WO-99/49788 A1 | 10/1999 |
| WO | WO-99/64060 A1 | 12/1999 |
| WO | WO-00/09666 A2 | 2/2000 |
| WO | WO-00/34331 A2 | 6/2000 |
| WO | WO-00/41546 A2 | 7/2000 |
| WO | WO-00/41548 A2 | 7/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | WO-01/04156 A1 | 1/2001 |
| WO | WO-01/32158 A2 | 5/2001 |
| WO | WO-02/34285 A2 | 5/2002 |
| WO | WO-03/022304 A1 | 3/2003 |
| WO | WO-03/053339 A2 | 7/2003 |
| WO | WO-03/053460 A1 | 7/2003 |
| WO | WO-03/082898 A2 | 10/2003 |
| WO | WO-2004/005342 A1 | 1/2004 |
| WO | WO-2004/062685 A2 | 7/2004 |
| WO | WO-2004/096854 A2 | 11/2004 |
| WO | WO-2005/072045 A2 | 8/2005 |
| WO | WO-2005/077072 A2 | 8/2005 |
| WO | WO-2006/051110 A2 | 5/2006 |
| WO | WO-2006/097537 A2 | 9/2006 |
| WO | WO-2006/121860 A2 | 11/2006 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/095737 A1 | 8/2007 |
| WO | WO-2007/100535 A2 | 9/2007 |
| WO | WO-2008/010101 A2 | 1/2008 |
| WO | WO-2008/071010 A1 | 6/2008 |
| WO | WO-2008/071972 A1 | 6/2008 |
| WO | WO-2008/101017 A2 | 8/2008 |
| WO | WO-2008/152403 A1 | 12/2008 |
| WO | WO-2008/155257 A1 | 12/2008 |
| WO | WO-2009/030738 A1 | 3/2009 |
| WO | WO-2009/067636 A2 | 5/2009 |
| WO | WO-2009/077737 A2 | 6/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/011439 A2 | 1/2010 |
| WO | WO-2010/014946 A2 | 2/2010 |
| WO | WO-2010/016940 A2 | 2/2010 |
| WO | WO-2010/029159 A2 | 3/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2010/096052 A1 | 8/2010 |
| WO | WO-2010/148089 A1 | 12/2010 |
| WO | WO-2011/006497 A1 | 1/2011 |
| WO | WO-2011/080103 A1 | 7/2011 |
| WO | WO-2011/084808 A2 | 7/2011 |
| WO | WO-2011/088837 A1 | 7/2011 |
| WO | WO-2011/094337 A1 | 8/2011 |
| WO | WO-2011/117416 A1 | 9/2011 |
| WO | WO-2011/117417 A1 | 9/2011 |
| WO | WO-2011/119657 A1 | 9/2011 |
| WO | WO-2011/134471 A1 | 11/2011 |
| WO | WO-2011/160630 A2 | 12/2011 |
| WO | WO-2011/160633 A1 | 12/2011 |
| WO | WO-2012/062803 A1 | 5/2012 |
| WO | WO-2012/062804 A1 | 5/2012 |
| WO | WO-2012/098462 A1 | 7/2012 |
| WO | WO-2012/130866 A1 | 10/2012 |
| WO | WO-2012/140117 A1 | 10/2012 |
| WO | WO-2012/150503 A2 | 11/2012 |
| WO | WO-2012/153196 A2 | 11/2012 |
| WO | WO-2012/167744 A1 | 12/2012 |
| WO | WO-2013/041678 A1 | 3/2013 |
| WO | WO-2013/092703 A2 | 6/2013 |
| WO | WO-2013/164483 A1 | 11/2013 |
| WO | WO-2013/192131 A1 | 12/2013 |
| WO | WO-2014/016300 A1 | 1/2014 |
| WO | WO-2014/041195 A1 | 3/2014 |
| WO | WO-2014/096150 A1 | 6/2014 |
| WO | WO-2015/067715 A2 | 5/2015 |
| WO | WO-2015/067716 A1 | 5/2015 |
| WO | WO-2015/124612 A1 | 8/2015 |
| WO | WO-2016/066744 A2 | 5/2016 |
| WO | WO-2016/166289 A1 | 10/2016 |

OTHER PUBLICATIONS

Ali et al., "Cardiomyocyte glucagon receptor signaling modulates outcomes in mice with experimental myocardial infarction," Mol Metab. 4(2):132-143 (2015).

Ally et al., "Rapid determination of creatine, phosphocreatine, purine bases and nucleotides (ATP, ADP, AMP, GTP, GDP) in heart biopsies by gradient ion-pair reversed-phase liquid chromatography," J Chromatogr. 575(1):19-27 (1992).

Altschul et al., "Local alignment statistics," Methods Enzymol. 266:460-480 (1996).

Arnold, "Heart failure," <http://www.merckmanuals.com/home/heart_and_blood_vessel_disorders/heart_failure/heart_failure.html?qt=congestive_heart_failure&alt=sh>, retrieved on Feb. 8, 2015 (12 pages).

Authier et al., "Endosomal proteolysis of glucagon at neutral pH generates the bioactive degradation product miniglucagon-(19-29)," Endocrinology. 144(12):5353-5364 (2003).

Bailey et al., "Glucagon-like peptide-1 and the entero-insular axis in obese hyperglycaemic (ob/ob) mice," Life Sci. 40(6):521-525 (1987).

Ban et al., "Cardioprotective and vasodilatory actions of glucagon-like peptide 1 receptor are mediated through both glucagon-like peptide 1 receptor-dependent and -independent pathways," Circulation. 117(18):2340-2350 (2008).

Bedford et al., "Amino acid structure and 'difficult sequences' in solid phase peptide synthesis," Int J Peptide Protein Res. 40(3-4):300-7 (1992).

Behme et al., "Glucagon-like peptide 1 improved glycemic control in Type 1 diabetes," BMC Endocr Disord. 3(1):3 (2003) (9 pages).

Bell, "Heart failure: the frequent, forgotten, and often fatal complication of diabetes," Diabetes Care. 26(8):2433-41 (2003).

Bhat et al., "A DPP-IV-resistant triple-acting agonist of GIP, GLP-1 and glucagon receptors with potent glucose-lowering and insulinotropic actions in high-fat-fed mice," Diabetologia 56(6):1417-24 (2013).

Blache et al., "Endopeptidase from rat liver membranes, which generates miniglucagon from glucagon," J Biol Chem. 268(29):21748-21753 (1993).

Bork, "Powers and pitfalls in sequence analysis: the 70% hurdle," Genome Research 10, 398-400, 2000.

Bowie et al., "Deciphering the message in protein sequences: tolerance to amino acid substitutions," Science. 247(4948):1306-10 (1990).

Burcelin et al., "Long-lasting antidiabetic effect of a dipeptidyl peptidase IV-resistant analog of glucagon-like peptide-1," Metabolism. 48(2):252-258 (1999).

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.

Buse et al., "The effect of epinephrine, glucagon, and the nutritional state on the oxidation of branched chain amino acids and pyruvate by isolated hearts and diaphragms of the rat," J Biol Chem. 248(2):697-706 (1973).

(56) References Cited

OTHER PUBLICATIONS

Buse, "Progressive use of medical therapies in type 2 diabetes," Diabetes Spectrum. 13(4):211-20 (2000).
Byrne et al., "Inhibitory effects of hyperglycaemia on fed jejunal motility: potential role of hyperinsulinaemia," Eur J Clin Invest. 28(1):72-78 (1998).
Carpenter et al., "Rational design of stable lyophilized protein formulations: some practical advice," Pharm Res. 14(8):969-75 (1997).
Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).
Chabenne et al., "Optimization of the native glucagon sequence for medicinal purposes," J Diabetes Sci Technol. 4(6):1322-31 (2010).
Chan et al., "Suppression of weight gain by glucagon in obese Zucker rats," Exp Mol Path. 40(3):320-327 (1984).
Chen et al., "Evidence that the diabetes gene encodes the leptin receptor: identification of a mutation in the leptin receptor gene in db/db mice," Cell. 84(3):491-5 (1996).
Chen et al., "Tissue-specific expression of unique mRNAs that encode proglucagon-derived peptides or exendin 4 in the lizard," J Biol Chem. 272(7):4108-15 (1997).
Christensen et al., "Lixisenatide, a novel GLP-1 receptor agonist for the treatment of type 2 diabetes mellitus," IDrugs 12(8):503-13 (2009).
Cleland et al., "The development of stable protein formulations: a close look at protein aggregation, deamidation, and oxidation," Crit Rev Ther Drug Carrier Syst. 10(4):307-77 (1993).
Cohen et al., "Oxyntomodulin suppresses appetite and reduces food intake in humans," J Clin Endocrinol Metab. 88(10):4696-4701 (2003).
Coleman, "Effects of parabiosis of obese with diabetes and normal mice," Diabetologia. 9(4):294-8 (1973).
Communication from the European Patent Office for European Patent Application No. 08875673.9, dated Jul. 4, 2012 (6 pages).
Curriculum Vitae (CV) of Keld Fosgerau, Ph.D. (9 pages).
D'Alessio et al., "Glucagon-like peptide 1 enhances glucose tolerance both by stimulation of insulin release and by increasing insulin-independent glucose disposal," J Clin Invest. 93(5):2263-66 (1994).
Dakin et al., "Oxyntomodulin inhibits food intake in the rat," Endocrinology. 142(10):4244-4250 (2001).
Dakin et al., "Peripheral oxyntomodulin reduces food intake and body weight gain in rats," Endocrinology. 145(6):2687-2695 (2004).
Day et al., "A new glucagon and GLP-1 co-agonist eliminates obesity in rodents," Nat Chem Biol. 5(10):749-757 (2009).
De Boer et al., "The tac promoter: a functional hybrid derived from the trp and lac promoters," Proc Natl Acad Sci USA. 80(1):21-5 (1983).
Deacon et al., "Dipeptidyl peptidase IV inhibition potentiates the insulinotropic effect of glucagon-like peptide 1 in the anesthetized pig," Diabetes. 47(5):764-9 (1998).
Deacon et al., "Dipeptidyl peptidase IV resistant analogues of glucagon-like peptide-1 which have extended metabolic stability and improved biological activity," Diabetologia. 41(3):271-8 (1998).
Decision in Inter Partes Reexam for U.S. Appl. No. 95/000,276, mailed Nov. 25, 2013 (29 pages).
Delgado et al., "The uses and properties of PEG-linked proteins," Crit Rev Ther Drug Carrier Syst. 9(3,4):249-304 (1992).
Diamant et al., "Diabetic cardiomyopathy in uncomplicated type 2 diabetes is associated with the metabolic syndrome and systemic inflammation," Diabetologia 48(8):1669-70 (2005).
Dickstein et al., "ESC Guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM)," Eur Heart J. 29(19):2388-442 (2008).
Druce et al., "Investigation of structure-activity relationships of Oxyntomodulin (Oxm) using Oxm analogs," Endocrinology. 150(4):1712-1721 (2009).
Drucker, "Glucagon-like peptides," Diabetes. 47(2):159-69 (1998).
Ebert et al., "Gastric inhibitory polypeptide," Clin Gastroenterol. 9(3):679-98 (1980).
Edvell et al., "Initiation of increased pancreatic islet growth in young normoglycemic mice (Umeå +/?)," Endocrinology. 140(2):778-83 (1999).
Ehrlich, "DNA cloning in Bacillus subtilis," Proc Natl Acad Sci USA. 75(3):1433-6 (1978).
EMEA Humalog Information: European Public Assessment Report (EPAR) and Scientific Discussions, 2006 (11 pages).
Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
England et al., "Glucagon carboxyl-terminal derivatives: Preparation, purification and characterization," Biochemistry. 21(5):940-950 (1982).
European Search Opinion and Extended European Search Report for European Patent Application No. 08016668.9, dated Jan. 27, 2009 (5 pages).
European Search Report for European Patent Application No. 09002937, dated Mar. 15, 2010 (5 pages).
European Search Report for European Patent Application No. 99610043, dated Jan. 18, 2000 (2 pages).
European Search Report from European Patent Application No. 07016032.0, completed Jan. 28, 2008 (8 pages).
Experimental Report provided in response to opposition filed against European Patent No. 1525219, filed Oct. 5, 2011 (4 pages).
Extended European Search Report for European Patent Application No. 08016668, dated Jan. 14, 2009 (4 pages).
Extended European Search Report for European Patent Application No. 11774431.8, dated Sep. 30, 2013 (11 pages).
Fang et al., "Diabetic cardiomyopathy: evidence, mechanisms, and therapeutic implications, " Endocr Rev. 25(4):543-67 (2004).
Farah et al., "Studies on the pharmacology of glucagon," J Pharmacol Exp Ther. 129:49-55 (1960).
Finan et al., "Reappraisal of GIP Pharmacology for Metabolic Diseases," Trends Mol Med. 22(5):359-76 (2016).
Fineman et al., "AC2993 (Synthetic Exendin-4) Improved Glycemic Control in Patients With Type 2 Diabetes During 28 Days of Treatment in a Multicenter, Randomized, Triple-Blind, Placebo-Controlled Study," Diabetes 51 (Supplement 2):A85, Abstract 343-OR, Abstract Book 62"d Scientific Sessions. POSTER. Jun. 14-18, 2002.
Fineman et al., Abstract 343-OR: "AC2993 (Synthetic Exendin-4) added to existing metformin (Met) and/or Sulfonylurea (SFU) treatment improved glycemic control in patients with type 2 diabetes (DM2) during 28 days of treatment," Diabetes. 51(Supplement 2):A85, Abstract Book, 62nd Scientific Sessions (2002) (3 pages).
First Examination Report for New Zealand Patent Application No. 702333, dated Jun. 2, 2016 (4 pages).
Fosgerau et al., "The novel GLP-1-gastrin dual agonist, ZP3022, increases beta-cell mass and prevents diabetes in db/db mice, " Diabetes Obes Metab. 15(1):62-71 (2013).
Francis et al., "PEGylation of cytokines and other therapeutic proteins and peptides: the importance of biological optimisation of coupling techniques," Int J Hematol. 68(1):1-18 (1998).
Frandsen et al., "Glucagon: structure-function relationships investigated by sequence deletions," Hoppe Seylers Z Physiol Chem. 362(6):665-677 (1981).
Gault et al., "Administration of an acylated GLP-1 and GIP preparation provides added beneficial glucose-lowering and insulinotropic actions over single incretins in mice with Type 2 diabetes and obesity," Clin Sci (Lond). 121(3):107-17 (2011).
Gelfanov et al., Discovery and structural optimization of high affinity co-agonists at the glucagon and GLP-1 receptors. Understanding Biology Using Peptides. Sylvie E. Blondelle, 763-764 (2005).

(56) References Cited

OTHER PUBLICATIONS

Goldstein et al., "Effects of chronic heart failure on the capacity of glucagon to enhance contractility and adenyl cyclase activity of human papillary muscles," Circulation. 44(4):638-648 (1971).
Gombotz et al. "Biodegradable polymers for protein and peptide drug delivery," Bioconjug Chem. 6(4):332-351 (1995).
Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).
Greig et al., "Once daily injection of exendin-4 to diabetic mice achieves long-term beneficial effects on blood glucose concentrations," Diabetologia. 42(1):45-50 (1999).
Grieve et al., "Emerging cardiovascular actions of the incretin hormone glucagon-like peptide-1: Potential therapeutic benefits beyond glycaemic control?," Br J Pharmacol. 157(8):1340-51 (2009).
Grounds of Appeal by F. Hoffmann-La Roche AG for European U.S. Pat. No. 1525219, filed Aug. 10, 2012 (35 pages).
Grounds of Appeal by Novo Nordisk A/S for European Patent No. 1525219, filed Aug. 3, 2012 (27 pages).
Gunn et al., "Central glucagon-like peptide-I in the control of feeding," Biochem Soc Trans. 24(2):581-4 (1996).
Guo et al., "3'-end-forming signals of yeast mRNA," Mol Cell Biol. 15(11):5983-90 (1995).
Göke et al., "Distribution of GLP-1 binding sites in the rat brain: Evidence that exendin-4 is a ligand of brain GLP-1 binding sites," Eur J Neurosci. 7(11):2294-2300 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Haffner et al., "Intensive lifestyle intervention or metformin on inflammation and coagulation in participants with impaired glucose tolerance," Diabetes. 54(5):1566-72 (2005).
Hamad et al., "Pharmacologic therapy of chronic heart failure," Am J Cardiovasc Drugs. 7(4):235-48 (2007).
Hansson, "Inflammation, atherosclerosis, and coronary artery disease," N Engl J Med. 352(16):1685-95 (2005).
Harikae, "The effects of a behavioral program in the obese NIDDM patients-observations on daily activity, degree of obesity and blood sugar control," Bulletin of the School of Nursing, Yamaguchi Prefectural University 2:1-13/E (1998) (Abstract in English).
Heinrich et al., "Pre-proglucagon messenger ribonucleic acid: nucleotide and encoded amino acid sequences of the rat pancreatic complementary deoxyribonucleic acid," Endocrinology. 115(6):2176-81 (1984).
Hjorth et al., "Glucagon and glucagon-like peptide 1: Selective receptor recognition via distinct peptide epitopes," J Biol Chem. 269(48):30121-30124 (1994).
Holst, "Enteroglucagon," Annu Rev Physiol. 59:257-71 (1997).
Holst, "Glucagon-like peptide-1, a gastrointestinal hormone with a pharmaceutical potential," Curr Med Chem. 6(11):1005-17 (1999).
Holst, "The physiology of glucagon-like peptide 1," Physiol Rev. 87(4): 1409-39 (2007).
Hostrup et al., Modification of Peptides and Proteins. Delivery Technologies for Biopharmaceuticals: Peptides, Proteins, Nucleic Acids and Vaccines. Jorgensen, Nielsen, 171-91 (2009).
Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
Hui et al., "The short half-life of glucagon-like peptide-1 in plasma does not reflect its long-lasting beneficial effects," Eur J Endocrinol. 146(6):863-9 (2002).
ICH Harmonised Tripartite Guideline, Feb. 5, 1998 (39 pages).
Igaki et al., "Investigation of effectiveness of low intensity exercise on body fat reduction in diabetics," J.Japan Phys Ther Assoc, 26:270-4 (1999). English abstract included.
Ingwall et al., "Is the failing heart energy starved? On using chemical energy to support cardiac function," Circ Res. 95(2):135-45 (2004).
International Dictionary of Medicine and Biology in Three Volumes: vol. II. John Wiley & Sons, New York,1328 (1986) (3 pages).
International Preliminary Examination Report for International Application No. PCT/DK03/00463, dated Sep. 20, 2004 (5 pages).
International Preliminary Report on Patentability for International Patent Application No. PCT/EP2014/073970, dated May 10, 2016 (10 pages).
International Preliminary Report on Patentability for International Patent Application No. PCT/EP2014/073971, dated May 10, 2016 (5 pages).
International Preliminary Report on Patentability for PCT/EP2013/069286, completed Jan. 19, 2015 (40 pages).
International Preliminary Report on Patentability for PCT/GB2008/002041, dated Dec. 17, 2009 (7 pages).
International Search Report and Written Opinion for International Application No. PCT/EP2015/075120, dated Jul. 15, 2016 (13 pages).
International Search Report and Written Opinion for International Application No. PCT/IB2012/001090, dated Jan. 25, 2013 (15 pages).
International Search Report and Written Opinion for International Patent Application No. PCT/EP2012/071766, dated Feb. 15, 2013 (9 pages).
International Search Report and Written Opinion for International Patent Application No. PCT/EP2014/073970, dated Aug. 26, 2015 (15 pages).
International Search Report and Written Opinion for International Patent Application No. PCT/EP2014/073971, dated Mar. 5, 2015 (7 pages).
International Search Report and Written Opinion for PCT/EP2013/059319, dated Sep. 12, 2013 (12 pages).
International Search Report and Written Opinion for PCT/EP2013/065519, dated Dec. 6, 2013 (11 pages).
International Search Report and Written Opinion for PCT/EP2013/069286, dated Dec. 18, 2013 (16 pages).
International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for International Application No. PCT/DK00/00393, dated Nov. 8, 2000 (3 pages).
International Search Report for International Application No. PCT/DK03/00463, dated Oct. 22, 2003 (7 pages).
International Search Report for International Application No. PCT/DK2010/000099, dated Dec. 2, 2010 (2 pages).
International Search Report for International Application No. PCT/DK2011/000067, dated Dec. 9, 2011 (4 pages).
International Search Report for International Application No. PCT/DK2011/050133 dated Oct. 6, 2011 (5 pages).
International Search Report for International Application No. PCT/IB2012/000134, dated Jun. 25, 2012 (3 pages).
International Search Report for International Application No. PCT/DK2011/050018, dated May 30, 2011 (6 pages).
International Search Report for PCT/DK2011/000072, dated Dec. 6, 2011 (3 pages).
International Search Report for PCT/GB2008/002041, dated Sep. 9, 2008 (3 pages).
International Search Report for PCT/GB2008/004157, dated Jun. 4, 2009 (21 pages).
Irwin et al., "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biol Chem. 386(7):679-87 (2005).

(56) References Cited

OTHER PUBLICATIONS

Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).
Jaya et al., "Mechanism of hypocholesterolemic action of glucagon," J Biosci. 12(2):111-4 (1987).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation.," Circulation. 119(14):1977-2016 (2009).
Joshi et al., "The estimation of glutaminyl deamidation and aspartyl cleavage rates in glucagon," Int J Pharm. 273(1-2):213-219 (2004).
Juntti-Berggren et al., "The antidiabetogenic effect of GLP-1 is maintained during a 7-day treatment period and improves diabetic dyslipoproteinemia in NIDDM patients," Diabetes Care. 19(11):1200-6 (1996).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Kitamura, "Is the "drug holiday" harmful?," Keio J Med. 25(3):131-7 (1976).
Kiyose et al., "Glucose tolerance screening method using a combination of fasting plasma glucose and hemoglobin A1c," J. Japan Diab Soc, 30:325-331 (1987). English abstract included.
Knudsen et al., "Potent derivatives of glucagon-like peptide-1 with pharmacokinetic properties suitable for once daily administration," J Med Chem. 43(9):1664-1669 (2000).
Korc, "Islet growth factors: curing diabetes and preventing chronic pancreatitis?," J Clin Invest. 92(3):1113-4 (1993).
Krchnák et al., "Aggregation of resin-bound peptides during solid-phase peptide synthesis. Prediction of difficult sequences," Int J Pept Protein Res. 42(5):450-4 (1993).
Larsen et al., "Glucagon-like peptide-1 infusion must be maintained for 24 h/day to obtain acceptable glycemia in type 2 diabetic patients who are poorly controlled on sulphonylurea treatment," Diabetes Care. 24(8):1416-21 (2001).
Larsen et al., "Sequence-assisted peptide synthesis (SAPS)," J Peptide Res. 52(6):470-6 (1998).
Lazar et al., "Transforming growth factor alpha: mutation of aspartic acid 47 and leucine 48 results in different biological activities," Mol. Cell. Biol. 8, 1247-52, 1988.
Lefèbvre, "The intriguing diversity of the glucagon gene products," Curr Diab Rep. 2(3):201-2 (2002).
Leiter et al., "Influence of dietary carbohydrate on the induction of diabetes in C57BL/KsJ-db/db diabetes mice," J Nutr. 113(1):184-95 (1983).
Levey et al., "Activation of adenyl cyclase by glucagon in cat and human heart," Circ Res. 24(2):151-6 (1969).
Lopaschuk et al., "Measurements of fatty acid and carbohydrate metabolism in the isolated working rat heart," Mol Cell Biochem. 172(1-2):137-47 (1997).
Loyter et al., "Mechanisms of DNA uptake by mammalian cells: fate of exogenously added DNA monitored by the use of fluorescent dyes," Proc Natl Acad Sci USA. 79(2):422-6 (1982).
Lvoff et al., "Glucagon in heart failure and in cardiogenic shock. Experience in 50 patients," Circulation. 45(3):534-42 (1972).
López-Delgado et al., "Effects of glucagon-like peptide 1 on the kinetics of glycogen synthase a in hepatocytes from normal and diabetic rats," Endocrinology. 139(6):2811-17 (1998).
Madsen et al., "Structure-activity and protraction relationship of long-acting glucagon-like peptide-1 derivatives: importance of fatty acid length, polarity, and bulkiness," J Med Chem. 50(24):6126-32 (2007).
Malde et al., "Understanding interactions of gastric inhibitory polypeptide (GIP) with its G-protein coupled receptor through NMR and molecular modeling," J Pept Sci. 13(5):287-300 (2007).

Manhart et al., "Structure-function analysis of a series of novel GIP analogues containing different helical length linkers," Biochemistry. 42(10):3081-8 (2003).
Manning et al., "Stability of protein pharmaceuticals," Pharm Res. 6(11):903-18 (1989).
Matsumoto et al., "Plasma Incretin Levels and Dipeptidyl Peptidase-4 Activity in Patients with Obstructive Sleep Apnea," Ann Am Thorac Soc. 13(8):1378-87 (2016).
Matthes et al., "Simultaneous rapid chemical synthesis of over one hundred oligonucleotides on a microscale," EMBO J. 3(4):801-5 (1984).
Mayer et al., "Effect of glucagon on cyclic 3',5'-AMP, phosphorylase activity and contractility of heart muscle of the rat," Circ Res. 26(2):225-33 (1970).
McKee et al., "Receptor binding and adenylate cyclase activities of glucagon analogues modified in the N-terminal region," Biochemistry. 25(7):1650-1656 (1986).
Mehta, "Diabetic cardiomyopathy: insights into pathogenesis, diagnostic challenges, and therapeutic options," Intl J Pharm Sci Res. 3(10):3565-3576 (2012).
Meier et al., "Absence of a memory effect for the insulinotropic action of glucagon-like peptide 1 (GLP-1) in healthy volunteers," Horm Metab Res. 35(9):551-6 (2003).
Meurer et al., "Properties of native and in vitro glycosylated forms of the glucagon-like peptide-1 receptor antagonist exendin (9-39)," Metabolism. 48(6):716-24 (1999).
Meyer et al., Effects of conformation on the Chemical Stability of Pharmaceutically Relevant Polypeptides. *Rational design of stable protein formulations*. Carpenter and Manning, 85-6 (2002).
Mojsov, "Structural requirements for biological activity of glucagon-like peptide-I," Int J Pept Protein Res. 40(3-4):333-43 (1992).
Nauck et al., "Glucagon-like peptide 1 and its potential in the treatment of non-insulin-dependent diabetes mellitus," Horm Metab Res. 29(9):411-6 (1997).
Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem 67(5):1982-91 (1996).
NCBI Blast for Accession No. 721913A, retrieved on Dec. 15, 2009 (1 page).
Neubauer et al., "Myocardial phosphocreatine-to-ATP ratio is a predictor of mortality in patients with dilated cardiomyopathy," Circulation. 96(7):2190-6 (1997) (9 pages).
Neumann et al., "Gene transfer into mouse lyoma cells by electroporation in high electric fields," EMBO J. 1(7):841-5 (1982).
Nikolaidis et al., "Active metabolite of GLP-1 mediates myocardial glucose uptake and improves left ventricular performance in conscious dogs with dilated cardiomyopathy," Am J Physiol Heart Circ Physiol. 289(6):H2401-8 (2005).
Nikolaidis et al., "Recombinant glucagon-like peptide-1 increases myocardial glucose uptake and improves left ventricular performance in conscious dogs with pacing-induced dilated cardiomyopathy," Circulation. 110(8):955-61 (2004).
Notarized Affidavit from the British Library regarding European Journal of Endocrinology, vol. 146, No. 6, Jun. 2002, mailed Apr. 21, 2011 (5 pages).
Notice of Allowance and Allowed Claims for U.S. Appl. No. 13/383,783, dated Jun. 22, 2015 (5 pages).
Notice of Allowance, previously Allowed Claims and Amendment after Allowance for U.S. Appl. No. 13/704,299, dated Jun. 26, 2015 (15 pages).
Notice of Allowance, previously Allowed Claims and Amendment after Allowance for U.S. Appl. No. 14/029,529, dated Jun. 29, 2015 (14 pages).
Notice of Appeal of Opposition Decision for European Patent No. 1525219 by F. Hoffmann-La Roche AG, filed May 21, 2012 (1 page).
Notice of Appeal of Opposition Decision for European Patent No. 1525219 by Novo Nordisk A/S, filed Apr. 23, 2012 (1 page).
Notice of Opposition to a European Patent for European Patent No. 1525219 on behalf of Novo Nordisk A/S, dated Feb. 25, 2010 (24 pages).

(56) References Cited

OTHER PUBLICATIONS

O'Shaughnessy et al., "Alpha-difluoromethylornithine as treatment for metastatic breast cancer patients," Clin Cancer Res. 5(11):3438-44 (1999) (8 pages).
Office Action for Colombian Application No. 16089238, dated Sep. 13, 2017 (18 pages).
Opposition to European Patent No. 1525219 on behalf of F. Hoffman-La Roche AG, dated Feb. 25, 2010 (34 pages).
Orskov, "Glucagon-like peptide-1, a new hormone of the entero-insular axis," Diabetologia. 35(8):701-11 (1992).
Overgaard et al., "Inotropes and vasopressors: review of physiology and clinical use in cardiovascular disease," Circulation. 118(10):1047-56 (2008).
Owens et al., "Insulins today and beyond," Lancet. 358(9283):739-46 (2001).
Pan et al., "Design of a long acting peptide functioning as both a glucagon-like peptide-1 receptor agonist and a glucagon receptor antagonist," J Biol Chem. 281(18):12506-12515 (2006).
Parkes et al., "Insulinotropic actions of exendin-4 and glucagon-like peptide-1 in vivo and in vitro," Metabolism. 50(5):583-9 (2001).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Parlevliet et al., "Oxyntomodulin ameliorates glucose intolerance in mice fed a high-fat diet," Am J Physiol Endocrinol Metab. 294(1):E142-E147 (2008).
Partial European Search Report for European Patent Application No. 03005786, dated Oct. 23, 2003 (6 pages).
Partial European Search Report for European Patent Application No. 99610043, dated Jan. 18, 2000 (4 pages).
PDR Medical Dictionary. Medical Economics, Montvale, New Jersey, p. 522 (1995) (3 pages).
Pederson et al., "Improved glucose tolerance in Zucker Fatty Rats by oral administration of the dipeptidyl peptidase IV inhibitor isoleucine thiazolidide," Diabetes. 47(8):1253-8 (1998).
Periasamy et al., "Molecular basis of diastolic dysfunction," available in PMC Jul. 6, 2009, published in final edited form as: Heart Fail Clin. 4(1):13-21 (2008) (13 pages).
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002, *Diabetologia* 45 (Suppl. 1):A147, Abstract No. 447 (2002) (2 pages).
Pocai et al., "Glucagon-like peptide 1/glucagon receptor dual agonism reverses obesity in mice," Diabetes. 58(10):2258-66 (2009).
Pocai, "Glucagon signaling in the heart: activation or inhibition?," Mol Metab. 4(2):81-2 (2015).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273(16):9778-84 (1998).
Poon et al., "Exenatide improves glycemic control and reduces body weight in subjects with type 2 diabetes: a dose-ranging study," Diabetes Technol Ther. 7(3):467-77 (2005).
Pratesi et al., "Poly-L-aspartic acid as a carrier for doxorubicin: a comparative in vivo study of free and polymer-bound drug," Br J Cancer. 52(6):841-848 (1985).
Prescribing information for Victoza (31 pages).
Pridal et al., "Absorption of glucagon-like peptide-1 can be protracted by zinc or protamine," Int J Pharm 136:53-59 (1996).
Protest of U.S. Appl. No. 12/664,534 Pursuant 37 CFR 1.291, dated Jan. 13, 2010 (14 pages).
Raufman et al., "Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist," J Biol Chem. 266(5):2897-902 (1991).

Raufman et al., "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).
Raufman, "Bioactive peptides from lizard venoms," Regul Pept. 61(1):1-18 (1996).
Ritzel et al., "A synthetic glucagon-like peptide-1 analog with improved plasma stability," J Endocrinol. 159(1):93-102 (1998).
Roach et al., "Improved postprandial glycemic control during treatment with humalog Mix25, a novel protamine-based insulin lispro formulation. Humalog Mix25 Study Group," Diabetes Care. 22(8):1258-61 (1999).
Robberecht et al., "Comparative efficacy of seven synthetic glucagon analogs, modified in position 1, 2, and/or 12, on liver and heart adenylate cyclase from rat," Peptides. 7(Suppl 1):109-12 (1986).
Rolin et al., "The long-acting GLP-1 derivative NN2211 ameliorates glycemia and increases beta-cell mass in diabetic mice," Am J Physiol Endocrinol Metab. 283(4):E745-52 (2002).
Rooman et al., "Gastrin stimulates beta-cell neogenesis and increases islet mass from transdifferentiated but not from normal exocrine pancreas tissue," Diabetes. 51(3):686-90 (2002).
Rose et al., "Insulin proteinase liberates from glucagon a fragment known to have enhanced activity against $Ca^{2+}$ + $Mg^{2+}$-dependent ATPase," Biochem J. 256(3):847-51 (1988).
Runge et al., "Differential structural properties of GLP-1 and exendin-4 determine their relative affinity for the GLP-1 receptor N-terminal extracellular domain," Biochemistry. 46(19):5830-40 (2007).
Saraceni et al., "Effects of glucagon-like peptide-1 and long-acting analogues on cardiovascular and metabolic function," Drugs R D. 8(3):145-53 (2007).
Sowden et al., "Oxyntomodulin increases intrinsic heart rate in mice independent of the glucagon-like peptide-1 receptor," Am J Physiol Regul Integr Comp Physiol. 292(2): R962-70 (2007).
Sporn et al., "Chemoprevention of cancer," Carcinogenesis. 21(3):525-530 (2000).
Stoffers et al., "Insulinotropic glucagon-like peptide 1 agonists stimulate expression of homeodomain protein IDX-1 and increase islet size in mouse pancreas," Diabetes. 49(5):741-8 (2000).
Suarez-Pinzon et al., "Combination therapy with epidermal growth factor and gastrin increases beta-cell mass and reverses hyperglycemia in diabetic NOD mice," Diabetes. 54(9):2596-601 (2005).
Suarez-Pinzon et al., "Combination therapy with glucagon-like peptide-1 and gastrin induces beta-cell neogenesis from pancreatic duct cells in human islets transplanted in immunodeficient diabetic mice," Cell Transplant. 17(6):631-40 (2008).
Suarez-Pinzon et al., "Combination therapy with glucagon-like peptide-1 and gastrin restores normoglycemia in diabetic NOD mice," Diabetes. 57(12):3281-8 (2008) (10 pages).
Table of Claims anticipated by WO 00/09666 (9 pages).
Tang-Christensen et al., "Central administration of GLP-1-(7-36) amide inhibits food and water intake in rats," Am J. Physiol. 271(4 Pt 2):R848-56 (1996).
Thorkildsen et al., "The exendin analogue ZP10 increases insulin mRNA expression in db/db mice," Nedergaard Symposium, Odense, Denmark, Jan. 24, 2002 (Poster presentation).
Thorkildsen et al., "ZP10—A New GLP-1 agonist that increases insulin mRNA expression," Nedergaard Symposium, Odense, Denmark, Jan. 24, 2002 (abstract only) (1 page).
Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002, Poster presentation.
Tomita et al., "Pancreatic islets of obese hyperglycemic mice (ob/ob)," Pancreas. 7(3):367-375 (1992).
Tourrel et al., "Glucagon-like peptide-1 and exendin-4 stimulate beta-cell neogenesis in streptozotocin-treated newborn rats resulting in persistently improved glucose homeostasis at adult age," Diabetes 50(7):1562-70 (2001).

(56) References Cited

OTHER PUBLICATIONS

Tourrel et al., "Persistent improvement of type 2 diabetes in the Goto-Kakizaki rat model by expansion of the beta-cell mass during the prediabetic period with glucagon-like peptide-1 or exendin-4," Diabetes. 51(5):1443-52 (2002).
Transition Therapeutics Inc., "Lilly and Transition Therapeutics announce licensing and collaboration agreement. Lilly to acquire exclusive rights to gastrin based therapies program for diabetes," <http://www.transitiontherapeutics.com/media/news.php>, retrieved May 28, 2015 (2 pages).
Transition Therapeutics Inc., "Positive preclinical data with Novo Nordisk A/S long-acting GLP-1 analog and gastrin combination presented at American Diabetes Association Meeting," <http://www.transitiontherapeutics.com/media/news.php>, retrieved on May 28, 2015 (1 page).
Translation of Office Action for Japanese Patent Application No. 2004-518465, dated Nov. 24, 2009 (6 pages).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Turton et al., "A role for glucagon-like peptide-1 in the central regulation of feeding," Nature 379(6560):69-72 (1996).
U.S. Appl. No. 14/095,667, filed Dec. 3, 2013 (99 pages).
U.S. Appl. No. 14/116,268, filed Nov. 7, 2013 (164 pages).
U.S. Appl. No. 15/852,458, filed Dec. 22, 2017 (57 pages).
U.S. Appl. No. 60/132,018, filed Apr. 30, 1999 (101 pages).
U.S. Appl. No. 61/784,294, filed Mar. 14, 2013 (54 pages).
Uesaka et al., "Glucagon-like peptide isolated from the eel intestine: Effects on atrial beating," J Exp Bio. 204(Pt 17):3019-26 (2001).
Underwood et al., "Crystal structure of glucagon-like peptide-1 in complex with the extracellular domain of the glucagon-like peptide-1 receptor," J Biol Chem. 285(1):723-30 (2010).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-10312 (1998).
Uttenthal et al., "Molecular forms of glucagon-like peptide-1 in human pancreas and glucagonomas," J Clin Endocrinol Metabol. 61(3):472-479 (1985).
Villa-Komaroff et al., "A bacterial clone synthesizing proinsulin," Proc Natl Acad Sci USA. 75(8):3727-31 (1978).
Wang et al., "Glucagon-like peptide-1 treatment delays the onset of diabetes in 8 week-old db/db mice," Diabetologia. 45(9):1263-73 (2002).
Warnica, "Acute coronary syndromes (Heart Attack; Myocardial Infarction; Unstable Angina)," <http://www.merckmanuals.com/home/heart_and_blood_vessel_disorders/coronary_artery_disease/acute_coronary_syndromes_heart_attack_myocardial_infarction_unstable_angina.html?qt-congestive_heart_failure&alt=sh>, retrieved on Feb. 8, 2015 (8 pages).
Wermuth et al., "Glossary of terms used in medicinal chemistry," Pure & Appl Chem. 70(5):1129-43 (1998).
Wettergren et al., "Truncated GLP-1 (proglucagon 78-107-amide) inhibits gastric and pancreatic functions in man," Dig Dis Sci. 38(4):665-73 (1993).
White, "A review of potential cardiovascular uses of intravenous glucagon administration," J Clin Pharmacol. 39(5):442-7 (1999).
Wiberg et al., "Replication and expression in mammalian cells of transfected DNA; description of an improved erythrocyte ghost fusion technique," Nucleic Acids Res. 11(21):7287-7302 (1983).

Wodarz et al., "Specific therapy regimes could lead to long-term immunological control of HIV," Proc Natl Acad Sci U.S.A. 96(25):14464-9 (1999).
Written Opinion for PCT/DK2011/000072, dated Dec. 6, 2011 (6 pages).
Written Opinion for Singapore Application No. 201209089-0, dated Nov. 8, 2013 (10 pages).
Written Opinion for Singapore Patent Application No. 2012078382, dated Feb. 17, 2015 (12 pages).
Written Opinion of the International Searching Authority for PCT/GB2008/002041, dated Sep. 9, 2008 (6 pages).
Xu et al., "Exendin-4 stimulates both beta-cell replication and neogenesis, resulting in increased beta-cell mass and improved glucose tolerance in diabetic rats," Diabetes. 48(12):2270-6 (1999).
Yabe et al., "Quantitative measurements of cardiac phosphorus metabolites in coronary artery disease by 31P magnetic resonance spectroscopy," Circulation. 92(1):15-23 (1995) (14 pages).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes. 48(5):1026-34 (1999).
Young et al., "Physiological and genetic factors affecting transformation of Bacillus subtilis," J Bacteriol. 81:823-9 (1961).
Zalipsky, "Functionalized poly(ethylene glycol) for preparation of biologically relevant conjugates," Bioconjug Chem. 6(2):150-165 (1995).
Zander et al., "Additive glucose-lowering effects of glucagon-like peptide-1 and metformin in type 2 diabetes," Diabetes Care. 24(4):720-5 (2001).
Zhao et al., "Direct effects of glucagon-like peptide-1 on myocardial contractility and glucose uptake in normal and postischemic isolated rat hearts," J Pharmacol Exp Ther. 317(3):1106-13 (2006).
Zhou et al., "Glucagon-like peptide 1 and exendin-4 convert pancreatic AR42J cells into glucagon- and insulin-producing cells," Diabetes. 48(12): 2358-66 (1999).
Zhu et al.,"The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).
International Search Report and Written Opinion for PCT/EP2016/058359, dated Jul. 15, 2016 (13 pages).
Lorenz et al., "Recent progress and future options in the development of GLP-1 receptor agonists for the treatment of diabesity," Bioorg Med Chem Lett. 23(14):4011-8 (2013).
Gault et al., "A Novel Glucagon-like Peptide-1 (GLP-1)/Glucagon Hybrid Peptide with Triple-acting Agonist Activity at Glucose-dependent Insulinotropic Polypeptide, GLP-1, and Glucagon Receptors and Therapeutic Potential in High Fat-fed Mice," J Biol Chem. 288(49): 35581-91 (2013).
Gault et al., "Glucose-dependent insulinotropic polypeptide analogues and their therapeutic potential for the treatment of obesity-diabetes," Biochem Biophys Res Commun. 308(2): 207-13 (2003).
Patterson et al., "A hydrophobic site on the GLP-1 receptor extracellular domain orients the peptide ligand for signal transduction," Mol Metab. 2(2):86-91 (2013).
Patel et al., "Co-agonist of glucagon and GLP-1 reduces cholesterol and improves insulin sensitivity independent of its effect on appetite and body weight in diet-induced obese C57 mice," Can J Physiol Pharmacol. 91(12):1009-15 (2013).
Gutniak et al., "Antidiabetogenic effect of glucagon-like peptide-1 (7-36)amide in normal subjects and patients with diabetes mellitus," N Engl J Med. 326(20):1316-22 (1992).
Perfetti et al., "Glucagon-like peptide-1: a major regulator of pancreatic beta-cell function," Eur J Endocrinol. 143(6): 717-25 (2000).

\* cited by examiner

GIP-GLP-1 DUAL AGONIST COMPOUNDS AND METHODS

FIELD OF THE INVENTION

The invention relates to compounds having agonist activity at both the GIP and GLP-receptors, and to their use in the treatment of metabolic disorders.

BACKGROUND OF THE INVENTION

Diabetes and obesity are increasing health problems globally and are associated with various other diseases, particularly cardiovascular diseases (CVD), obstructive sleep apnea, stroke, peripheral artery disease, microvascular complications and osteoarthritis. There are 246 million people worldwide with diabetes, and by 2025 it is estimated that 380 million will have diabetes. Many have additional cardiovascular risk factors including high/aberrant LDL and triglycerides and low HDL. Cardiovascular diseases account for about 50% of the mortality in people with diabetes, and the morbidity and mortality rates relating to obesity and diabetes underscore the medical need for efficacious treatment options.

Incretins are gastrointestinal hormones that regulate blood glucose by enhancing glucose-stimulated insulin secretion (Drucker, D J and Nauck, M A, Lancet 368: 1696-705 (2006)). To date there are two known incretins: glucagon-like peptide-1 (GLP-1), and glucose-dependent insulinotropic polypeptide (GIP). The incretin GLP-1 is derived from the pre-proglucagon gene. Pre-proglucagon is a 158-amino acid precursor polypeptide that is processed in different tissues to form a number of different proglucagon-derived peptides, including glucagon, GLP-1, glucagon-like peptide-2 (GLP-2) and oxyntomodulin (OXM). Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GIP is a 42-amino acid peptide derived by proteolytic processing from a 133-amino acid precursor, pre-pro-GIP. All the peptides are involved in a wide variety of physiological functions, including glucose homeostasis, insulin secretion, gastric emptying, and intestinal growth, as well as the regulation of food intake.

The discovery of the incretins has led to the development of two new classes of drugs for the treatment of diabetes mellitus. Thus, injectable GLP-1 receptor agonists, and small molecule compounds (oral DPP-4 inhibitors) that inhibit enzymatic inactivation of both endogenous GLP-1 and GIP, are now on the market (GLP-1 receptor agonists: Byetta™, Bydureon™ Lixisenatide™ and Victoza™; and DPP-4 inhibitors: Januvia™, Galvus™, Onglyza™ and Trajenta™). Apart from the acute effects of GLP-1 and GIP on insulin secretion, the incretins have some long-term effects. Evidence from several laboratories shows that GLP-1 receptor agonists protect pancreatic β-cells by inhibiting apoptosis and enhancing proliferation. For instance, a study by Farilla et al. showed that GLP-1 has anti-apoptotic effects in human islets (Farilla, L, Endocrinology 144: 5149-58 (2003)). Such effects have not been reported for GIP until recently. Weidenmaier et al. reported that a DPP-4 resistant GIP analogue had anti-apoptotic effects (Weidenmaier, S D, PLOS One 5(3): e9590 (2010)). Interestingly, in a mouse model of diabetes and obesity, the combination of the GLP-1 receptor agonist Liraglutide and an acylated GIP analogue showed superior glucose-lowering and insulino-tropic effects compared to treatment with Liraglutide and GIP analogue alone (Gault, V A, Clinical Science 121: 107-117 (2011)).

Chronic treatment with GLP-1 receptor agonists causes significant weight loss in diabetic humans. Interestingly, extended use of DPP-4 inhibitors in similar patients does not consistently change body weight. Evidence suggests (Matthias Tschop oral presentation at ADA (American Diabetes Association), 2011) that body weight loss associated with GLP-1 agonist treatment is enhanced when GLP-1 and GIP are co-administered. In rodents, co-administration of GLP-1 and GIP results in greater body weight loss than GLP-1 treatment alone (Finan, Sci Transl Med. 2013; 5(209): 209ra151. Irwin N et al, 2009, Regul Pept; 153: 70-76. Gault et al, 2011, Clin Sci; 121:107-117). Thus, in addition to improving blood glucose control, GIP may also enhance GLP-1-mediated body weight loss.

Recently, different peptides have been shown to bind and activate both the GIP and the GLP-1 receptor and to suppress body weight gain and reduce food intake (see, for example WO2012/088116, WO2010/148089, WO2012/167744, WO 2913/164483, WO 2014/096145, WO 2014/096150 and WO 2014/096149). However, most of these peptides have short terminal elimination half-life (T½).

SUMMARY OF THE INVENTION

Broadly, the present invention concerns acylated and truncated GIP analogues which comprise one or more substitutions as compared to wild-type GIP and which may have the property of an altered, preferably increased GLP-1 activity, e.g., as assessed in in vitro efficacy assays and an altered, preferably increased terminal elimination half-life (T½), as assessed in in vivo studies in mice.

It has been found in animals that GIP-GLP1 dual acting receptor agonists are superior to existing and marketed GLP-1 analogues because the dual agonists offer improved glycemic control, and enhanced body weight loss. The GIP-GLP1 dual agonists disclosed herein (also referred to as GIP analogues) may thus be used as therapeutics for metabolic disorders including, but not limited to, type 2 diabetes mellitus, obesity and related disorders.

The invention provides a GIP analogue having the general Formula I:

(SEQ ID NO: 56)
$R^1$-Tyr-X2-Glu-Gly-Thr-Phe-Thr-Ser-Asp-X10-Ser-Ile-X13-Leu-X15-X16-Ψ-Ala-X19-X20-X21-Phe-X23-X24-Trp-Leu-X27-X28-X29-X30-$R^2$ (I)

wherein
$R^1$ is H, $C_{1-4}$ alkyl, acetyl, formyl, benzoyl, trifluoroacetyl or pGlu;
X2 is selected from Aib and D-Ala;
X10 is selected from Tyr and Leu;
X13 is selected from Ala, Tyr and Aib;
X15 is selected from Asp and Glu;
X16 is selected from Glu and Lys;
X19 is selected from Gln and Ala;
X20 is selected from Lys and Arg;
X21 is selected from Ala and Glu;
X23 is selected from Val and Ile;
X24 is selected from Asn and Glu;
X27 is selected from Leu, Glu and Val;
X28 is selected from Ala, Ser and Arg;

X29 is selected from Aib, Ala, and Gln;
X30 is selected from Lys, Gly and Y1, or is absent;
Y1 (when present) is selected from Gly-Pro-Ser-Ser-Gly-Ala-Pro-Pro-Pro-Ser (SEQ ID NO: 57), Lys-Pro-Ser-Ser-Gly-Ala-Pro-Pro-Pro-Ser (SEQ ID NO: 58), Gly-Pro-Ser-Ser-Gly-Ala-Pro-Pro-Pro-Ser (SEQ ID NO: 59), Pro-Ser-Ser-Gly-Ala-Pro-Pro-Pro-Ser (SEQ ID NO: 60) and Pro-Ser-Ser-Gly-Ala-Pro-Pro-Pro-Ser (SEQ ID NO: 61);

ψ is a residue of Lys, Arg, Orn or Cys in which the side chain is conjugated to a substituent having the formula —$Z^1$ or —$Z^2$—$Z^1$; where:

—$Z^1$ is a fatty chain having a polar group at one end of the chain and a connection to ψ or $Z^2$, —X— at the end of the chain distal from the polar group, wherein the polar group comprises a carboxylic acid or a carboxylic acid bioisostere, a phosphonic acid, or a sulfonic acid group;

and —X— is a bond, —CO—, —SO—, or —$SO_2$—;

—$Z^2$— (if present) is a spacer of formula:

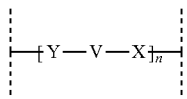

connecting $Z^1$ to ψ;
wherein:
each Y is independently —NH, —NR, —S or —O, where R is alkyl, a protecting group or forms a linkage to another part of the spacer $Z^2$;
each X is independently a bond, CO—, SO—, or $SO_2$—;
with the proviso that when Y is —S, the X to which it is bound is a bond;
each V is independently a bivalent organic moiety linking Y and X;
and n is 1-10;
and
$R^2$ is —$NH_2$ or —OH;
or a pharmaceutically acceptable salt or solvate thereof.

The invention also provides a GIP analogue having the general Formula Ib:

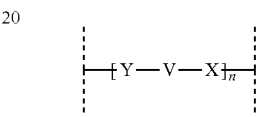

(SEQ ID NO: 56)
$R^1$-Tyr-X2-Glu-Gly-Thr-Phe-Thr-Ser-Asp-X10-Ser-Ile-

X13-Leu-X15-X16-Ψ-Ala-X19-X20-X21-Phe-X23-X24-Trp-

Leu-X27-X28-X29-X30-$R^2$ (Ib)

wherein
$R^1$ is H, $C_{1-4}$ alkyl, acetyl, formyl, benzoyl, trifluoroacetyl or pGlu;
X2 is selected from Aib and D-Ala;
X10 is selected from Tyr and Leu;
X13 is selected from Ala, Tyr and Aib;
X15 is selected from Asp and Glu;
X16 is selected from Glu and Lys;
X19 is selected from Gln and Ala;
X20 is selected from Lys and Arg;
X21 is selected from Ala and Glu;
X23 is selected from Val and Ile;
X24 is selected from Asn and Glu;
X27 is selected from Leu, Glu and Val;
X28 is selected from Ala, Ser and Arg;
X29 is selected from Aib, Ala, Glu and Gln;
X30 is selected from Lys, Gly and Y1, or is absent;

Y1 (when present) is selected from Gly-Pro-Ser-Ser-Gly-Ala-Pro-Pro-Pro-Ser (SEQ ID NO: 57), Lys-Pro-Ser-Ser-Gly-Ala-Pro-Pro-Pro-Ser (SEQ ID NO: 58), Gly-Pro-Ser-Ser-Gly-Ala-Pro-Pro-Pro-Ser (SEQ ID NO: 59), Pro-Ser-Ser-Gly-Ala-Pro-Pro-Pro-Ser (SEQ ID NO: 60) and Pro-Ser-Ser-Gly-Ala-Pro-Pro-Pro-Ser (SEQ ID NO: 61);

ψ is a residue of Lys, Arg, Orn or Cys in which the side chain is conjugated to a substituent having the formula —$Z^1$ or —$Z^2$—$Z^1$; where:

—$Z^1$ is a fatty chain having a polar group at one end of the chain and a connection to 44 or $Z^2$, —X— at the end of the chain distal from the polar group, wherein the polar group comprises a carboxylic acid or a carboxylic acid bioisostere, a phosphonic acid, or a sulfonic acid group;

and —X— is a bond, —CO—, —SO—, or —$SO_2$—;

—$Z^2$— (if present) is a spacer of formula:

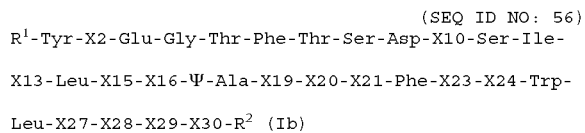

connecting $Z^1$ to ψ;
wherein:
each Y is independently —NH, —NR, —S or —O, where R is alkyl, a protecting group or forms a linkage to another part of the spacer $Z^2$;
each X is independently a bond, CO—, SO—, or $SO_2$—;
with the proviso that when Y is —S, the X to which it is bound is a bond;
each V is independently a bivalent organic moiety linking Y and X;
and n is 1-10;
and
$R^2$ is —$NH_2$ or —OH;
or a pharmaceutically acceptable salt or solvate thereof.

The invention further provides a GIP analogue having the general Formula II:

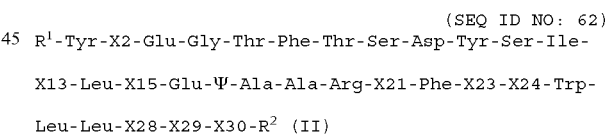

(SEQ ID NO: 62)
$R^1$-Tyr-X2-Glu-Gly-Thr-Phe-Thr-Ser-Asp-Tyr-Ser-Ile-

X13-Leu-X15-Glu-Ψ-Ala-Ala-Arg-X21-Phe-X23-X24-Trp-

Leu-Leu-X28-X29-X30-$R^2$ (II)

wherein
$R^1$ is H, $C_{1-4}$ alkyl, acetyl, formyl, benzoyl, trifluoroacetyl or pGlu;
X2 is selected from Aib and D-Ala;
X13 is selected from Ala, Tyr;
X15 is selected from Asp and Glu;
X21 is selected from Ala and Glu;
X23 is selected from Val and Ile;
X24 is selected from Asn and Glu;
X28 is selected from Ala, Ser;
X29 is selected from Ala, Glu and Gln; and
X30 is selected from Lys, Gly and Y1, or is absent;
Y1 (when present) is selected from Gly-Pro-Ser-Ser-Gly-Ala-Pro-Pro-Pro-Ser (SEQ ID NO: 57), Lys-Pro-Ser-Ser-Gly-Ala-Pro-Pro-Pro-Ser (SEQ ID NO: 58), Gly-Pro-Ser-Ser-Gly-Ala-Pro-Pro-Pro-Ser (SEQ ID NO: 59), Pro-Ser-Ser-Gly-Ala-Pro-Pro-Pro-Ser (SEQ ID NO: 60) and Pro-Ser-Ser-Gly-Ala-Pro-Pro-Pro-Ser (SEQ ID NO: 61);

ψ is a residue of Lys, Arg, Orn or Cys in which the side chain is conjugated to a substituent having the formula —$Z^1$ or —$Z^2$—$Z^1$; where:

—$Z^1$ is a fatty chain having a polar group at one end of the chain and a connection to ψ or $Z^2$, —X— at the end of the chain distal from the polar group, wherein the polar group comprises a carboxylic acid or a carboxylic acid bioisostere, a phosphonic acid, or a sulfonic acid group;

and —X— is a bond, —CO—, —SO—, or —$SO_2$—;

—$Z^2$— (if present) is a spacer of formula:

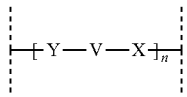

connecting $Z^1$ to ψ;
wherein:
each Y is independently —NH, —NR, —S or —O, where R is alkyl, a protecting group or forms a linkage to another part of the spacer $Z^2$;
each X is independently a bond, CO—, SO—, or $SO_2$—;
with the proviso that when Y is —S, the X to which it is bound is a bond;
each V is independently a bivalent organic moiety linking Y and X;
and n is 1-10;
and
$R^2$ is —$NH_2$ or —OH;
or a pharmaceutically acceptable salt or solvate thereof.

For the avoidance of doubt, in all aspects of the invention, those positions which are not expressly stated to permit variability are fixed and may only include the stated residue.

Combinations of residues which may be present at some of the variable positions from 1 to 29 include:
Gln19, Arg20, Ala21;
Aib2, Gln19, Arg20, Ala21;
Asp15, Gln19, Arg20, Ala21;
Aib2, Ala13, Gln19, Arg20, Ala21;
Lys16, Gln19, Arg20, Ala21;
Aib2, Ala13, Gln19, Arg20, Ala21;
Aib2, Asp15, Gln19, Arg20, Ala21;
Aib2, Lys16, Gln19, Arg20, Ala21;
Aib2, Asp15, Lys16, Gln19, Arg20, Ala21;
Leu27, Ala28, Gln29;
Glu24, Leu27, Ala28, Gln29;
Gln19, Arg20, Ala21; Leu27, Ala28, Gln29;
Gln19, Arg20, Ala21; Glu24, Leu27, Ala28, Gln29;
Asp15, Gln19, Arg20, Ala21;
Glu15, Gln19, Arg20, Ala21;
Aib2, Glu15, Gln19, Arg20, Ala21;
Aib2, Glu15, Lys16, Gln19, Arg20, Ala21;
Glu15, Leu27, Ala28, Gln29;
Glu15, Gln19, Arg20, Ala21; Leu27, Ala28, Gln29;
Glu15, Gln19, Arg20, Ala21, Glu24;
Aib2, Glu15, Gln19, Arg20, Ala21, Glu24;
Aib2, Ala13, Asp15, Gln19, Arg20, Ala21, Glu24;
Aib2, Ala13, Asp15, Gln19, Arg20, Ile23, Glu24;
Aib2, Glu15, Lys16, Gln19, Arg20, Ala21, Glu24;
Aib2, Ala13, Gln19, Arg20, Ala21, Glu24;
Asp15, Ile23, Gln29
Glu15, Glu24, Leu27, Ala28, Gln29;
Glu15, Gln19, Arg20, Ala21; Glu24, Leu27, Ala28, Gln29;
Ala19, Lys20, Glu21;
Ala13, Ala19, Lys20, Glu21;
Ala19, Lys20, Glu21, Ser28;
Ala19, Lys20, Glu21, Ala29;
Ala19, Lys20, Glu21, Ser28, Ala29;
Glu15, Ala19, Lys20, Glu21;
Ala13, Asp15, Ala19, Lys20, Glu21;
Glu15, Ala19, Lys20, Glu21, Ser28;
Glu15, Ala19, Lys20, Glu21, Ala29;
Ala13, Asp15, Ala19, Lys20, Glu21, Ala29;
Glu15, Ala19, Lys20, Glu21, Ser28, Ala29;
Glu16, Ala19, Lys20, Glu21;
Ala13, Asp15, Glu24, Gln29
Glu16, Ala19, Lys20, Glu21, Ser28;
Glu16, Ala19, Lys20, Glu21, Ala29;
Glu16, Ala19, Lys20, Glu21, Ser28, Ala29;
Ala13, Asp15, Ile23;
Glu27, Ser28, Ala29;
Glu16, Glu27, Ser28, Ala29;
Ala19, Lys20, Glu21, Glu27, Ser28, Ala29;
Glu16, Ala19, Lys20, Glu21, Glu27, Ser28, Ala29;
Val27, Aib29;
Asn24, Val27, Aib29;
Ala13, Asp15, Glu27;
Asn24, Aib29;
Glu15, Glu27;
Glu15, Glu24; and
Leu10, or any of the above in combination with Leu10.

In some embodiments, positions 1 to 29 of the GIP analogue have a maximum of 8 changes (within the constraints of Formula I) compared to the sequence:

(SEQ ID NO: 63)
Y-Aib-EGTFTSDYSIYLDKKAQRAFVEWLLAQ e.g. a maximum of 1, 2, 3, 4, 5, 6 or 7 changes compared to that sequence.

If positions 1 to 29 of the GIP analogue have 6 or more changes compared to that sequence, then they may possess all of Ala19, Lys20 and Glu21. They may also possess one or both of Ser28 and Ala29.

If the analogue does not possess Ala19, Lys20 and Glu21, then positions 1 to 29 typically have 4 or fewer changes compared to that sequence.

In other embodiments, positions 1 to 29 of the GIP analogue have a maximum of 6 changes (within the constraints of Formula I) compared to the sequence (SEQ ID NO: 64)
Y-Aib-EGTFTSDYSIYLEKKAAKEFVEWLLSA
or (SEQ ID NO: 65)
Y-Aib-EGTFTSDYSIYLDEKAAKEFIEWLESA e.g. a maximum of 1, 2, 3, 4 or changes compared to one of those sequences.

It may be desirable that such analogues retain one, two, or all of Ala19, Lys20 and Glu21.

They may additionally possess one or more of the following:
Glu15 and/or Glu16;
Ser28 and/or Ala29;
Val27 and/or Aib29;
Asn24, Val27 and/or Aib29;
Asn24 and/or Aib29;
Glu15 and/or Glu27;
Ala13, Glu15 and/or Glu16;
Ala13, Ser28 and/or Ala29;

Ala13, Val27 and/or Aib29;
Ala13, Asn24, Val27 and/or Aib29;
Ala13, Asn24 and/or Aib29;
Ala13, Glu15 and/or Glu27;
Asp15 and/or Glu16;
Asp15, Ser28 and/or Ala29;
Asp15, Val27 and/or Aib29;
Asp15, Asn24, Val27 and/or Aib29;
Asp15, Asn24 and/or Aib29;
Asp15 and/or Glu27;
Glu15 or Glu16 and/or Ile23;
Ile23, Ser28 and/or Ala29;
Ile23, Val27 and/or, Aib29;
Ile23, Asn24, Val27 and/or Aib29;
Ile23, Asn24 and/or Aib29;
Glu15, Ile23 and/or Glu27.
Aib2 and/or Ala13;
Aib2 and/or Tyr13;
Asp15 and/or Glu16;
Ile23 and/or Glu24;
DAla, Ser28 and/or Ala29;
Asn24 and/or, Arg20;
Asn24 and/or, Ala29.

Specific combinations of residues which may be present at the variable positions between 1 and 29 include:
Aib2, Tyr10, Tyr13, Asp15, Lys16, Gln19, Arg20, Ala21, Val23, Glu24, Leu27, Ala28, Gln29;
D-Ala2, Tyr10, Tyr13, Asp15, Lys16, Gln19, Arg20, Ala21, Val23, Glu24, Leu27, Ala28, Gln29;
Aib2, Tyr10, Tyr13, Glu15, Lys16, Ala19, Lys20, Glu21, Val23, Glu24, Leu27, Ser28, Ala29;
Aib2, Tyr10, Aib13, Asp15, Lys16, Gln19, Arg20, Ala21, Val23, Glu24, Leu27, Ala28, Gln29;
Aib2, Tyr10, Tyr13, Asp15, Lys16, Gln19, Arg20, Ala21, Val23, Asn24, Leu27, Ala28, Aib29;
Aib2, Tyr10, Tyr13, Asp15, Glu16, Ala19, Lys20, Glu21, Ile23, Glu24, Glu27, Ser28, Ala29;
Aib2, Tyr10, Ala13, Asp15, Lys16, Gln19, Arg20, Ala21, Val23, Asn24, Val27, Ala28, Aib29;
Aib2, Tyr10, Ala13, Glu15, Lys16, Gln19, Arg20, Ala21, Val23, Glu24, Leu27, Ala28, Gln29;
Aib2, Leu10, Ala13, Glu15, Lys16, Gln19, Arg20, Ala21, Val23, Glu24, Leu27, Ala28, Gln29;
Aib2, Tyr10, Tyr13, Glu15, Lys16, Gln19, Arg20, Ala21, Val23, Glu24, Leu27, Arg28, Ala29;
Aib2, Leu10, Ala13, Asp15, Lys16, Gln19, Arg20, Ala21, Val23, Asn24, Val27, Ala28 Aib29;
Aib2, Tyr10, Ala13, Asp15, Lys16, Gln19, Arg20, Ala21, Val23, Glu24, Val27, Ala28, Aib29;
Aib2, Tyr10, Ala13, Glu15, Lys16, Gln19, Arg20, Ala21, Val23, Glu24, Glu27, Ala28, Gln29;
Aib2, Tyr10, Ala13, Glu15, Lys16, Gln19, Arg20, Ala21, Val23, Glu24, Glu27, Ala28, Gln29;
Aib2, Leu10, Ala13, Glu15, Lys16, Gln19, Arg20, Ala21, Val23, Glu24, Glu27, Ala28, Gln29;
Aib2, Tyr10, Ala13, Asp15, Lys16, Gln19, Arg20, Ala21, Val23, Glu24, Leu27, Ala28, Gln29;
D-Ala2, Tyr10, Ala13, Asp15, Lys16, Gln19, Arg20, Ala21, Val23, Glu24, Leu27, Ala28, Gln29;
Aib2, Tyr10, Ala13, Glu15, Lys16, Ala19, Lys20, Glu21, Val23, Glu24, Leu27, Ser28, Ala29;
Aib2, Tyr10, Ala13, Asp15, Lys16, Gln19, Arg20, Ala21, Val23, Glu24, Leu27, Ala28, Gln29;
Aib2, Tyr10, Ala13, Asp15, Lys16, Gln19, Arg20, Ala21, Val23, Asn24, Leu27, Ala28, Aib29;
Aib2, Tyr10, Ala13, Asp15, Glu16, Ala19, Lys20, Glu21, Ile23, Glu24, Glu27, Ser28, Ala29;
Aib2, Tyr10, Ala13, Glu15, Lys16, Gln19, Arg20, Ala21, Val23, Glu24, Leu27, Arg28, Ala29;
Aib2, Tyr10, Tyr13, Asp15, Lys16, Gln19, Arg20, Ala21, Ile23, Glu24, Leu27, Ala28, Gln29;
D-Ala2, Tyr10, Tyr13, Asp15, Lys16, Gln19, Arg20, Ala21, Ile23, Glu24, Leu27, Ala28, Gln29;
Aib2, Tyr10, Tyr13, Glu15, Lys16, Ala19, Lys20, Glu21, Ile23, Glu24, Leu27, Ser28, Ala29;
Aib2, Tyr10, Aib13, Asp15, Lys16, Gln19, Arg20, Ala21, Ile23, Glu24, Leu27, Ala28, Gln29;
Aib2, Tyr10, Tyr13, Asp15, Lys16, Gln19, Arg20, Ala21, Ile23, Asn24, Leu27, Ala28, Aib29;
Aib2, Tyr10, Ala13, Asp15, Lys16, Gln19, Arg20, Ala21, Ile23, Asn24, Val27, Ala28, Aib29;
Aib2, Tyr10, Ala13, Glu15, Lys16, Gln19, Arg20, Ala21, Ile23, Glu24, Leu27, Ala28, Gln29;
Aib2, Leu10, Ala13, Glu15, Lys16, Gln19, Arg20, Ala21, Ile23, Glu24, Leu27, Ala28, Gln29;
Aib2, Tyr10, Tyr13, Glu15, Lys16, Gln19, Arg20, Ala21, Ile23, Glu24, Leu27, Arg28, Ala29;
Aib2, Leu10, Ala13, Asp15, Lys16, Gln19, Arg20, Ala21, Ile23, Asn24, Val27, Ala28 Aib29;
Aib2, Tyr10, Ala13, Asp15, Lys16, Gln19, Arg20, Ala21, Ile23, Glu24, Val27, Ala28, Aib29;
Aib2, Tyr10, Ala13, Glu15, Lys16, Gln19, Arg20, Ala21, Ile23, Glu24, Glu27, Ala28, Gln29;
Aib2, Tyr10, Ala13, Glu15, Lys16, Gln19, Arg20, Ala21, Ile23, Glu24, Glu27, Ala28, Gln29;
Aib2, Leu10, Ala13, Glu15, Lys16, Gln19, Arg20, Ala21, Ile23, Glu24, Glu27, Ala28, Gln29.

Residues 1-29 of Formula I may have the sequence:

```
                                                  (SEQ ID NO: 66)
Y-Aib-EGTFTSDYSIYLDKΨPAQRAFVEWLLAQ;

(SEQ ID NO: 67)
Y-DAla-EGTFTSDYSIYLDKΨPAQRAFVEWLLAQ;

(SEQ ID NO: 68)
Y-Aib-EGTFTSDYSIYLEKΨPAAKEFVEWLLSA;

(SEQ ID NO: 69)
Y-Aib-EGTFTSDYSI-Aib-LDKΨPAQRAFVEWLLAQ;

(SEQ ID NO: 70)
Y-Aib-EGTFTSDYSIYLDKΨPAQRAFVNWLLA-Aib;

(SEQ ID NO: 71)
Y-Aib-EGTFTSDYSIYLDEΨPAAKEFIEWLESA;

(SEQ ID NO: 72)
Y-Aib-EGTFTSDYSIALDKΨPAQRAFVNWLVA-Aib;

(SEQ ID NO: 73)
Y-Aib-EGTFTSDYSIALEKΨPAQRAFVEWLLAQ;

(SEQ ID NO: 74)
Y-Aib-EGTFTSDLSIALEKΨPAQRAFVEWLLAQ;

(SEQ ID NO: 75)
Y-Aib-EGTFTSDYSIYLEKΨPAQRAFVEWLLRA;

(SEQ ID NO: 76)
Y-Aib-EGTFTSDLSIALDKΨPAQRAFVNWLVA-Aib;

(SEQ ID NO: 77)
Y-Aib-EGTFTSDYSIALDKΨPAQRAFVEWLVA-Aib;

(SEQ ID NO: 78)
Y-Aib-EGTFTSDYSIALEKΨPAQRAFVEWLEAQ;

(SEQ ID NO: 79)
Y-Aib-EGTFTSDLSIALEKΨPAQRAFVEWLEAQ;
```

Y-Aib-EGTFTSDYSIALEKΨPAQRAFVEWLLAQ; (SEQ ID NO: 73)

Y-DAla-EGTFTSDYSIALEKΨPAQRAFVEWLLAQ; (SEQ ID NO: 80)

Y-Aib-EGTFTSDLSIALEKΨPAQRAFVEWLLAQ; (SEQ ID NO: 74)

Y-Aib-EGTFTSDYSIALDKΨPAQRAFVEWLLAQ; (SEQ ID NO: 81)

Y-DAla-EGTFTSDYSIALDKΨPAQRAFVEWLLAQ; (SEQ ID NO: 82)

Y-Aib-EGTFTSDYSIALDKΨPAQRAFVEWLLAAP; (SEQ ID NO: 83)

Y-Aib-EGTFTSDYSIALDKΨPAAKEFVEWLLSA; (SEQ ID NO: 84)

Y-Aib-EGTFTSDYSIALDEΨPAQRAFVEWLLAQ; (SEQ ID NO: 85)

Y-Aib-EGTFTSDYSIALDKΨPAQKAFVEWLLAA; (SEQ ID NO: 86)

Y-Aib-EGTFTSDYSIALDEΨPAQRAFVEWLLAA; (SEQ ID NO: 87)

Y-Aib-EGTFTSDYSIYLDKΨPAQREFVEWLLAQ; (SEQ ID NO: 88)

Y-Aib-EGTFTSDYSIALDKΨPAQREFVEWLLAQ; (SEQ ID NO: 89)

Y-Aib-EGTFTSDYSIALDKΨPAQKEFVEWLLAQ; (SEQ ID NO: 90)

Y-Aib-EGTFTSDYSIALDKΨPAQKEFVEWLLAA; (SEQ ID NO: 91)

Y-Aib-EGTFTSDYSIALDKΨPAQRAFIEWLLAQ [[-]]; (SEQ ID NO: 92)

Y-Aib-EGTFTSDYSIALDKΨPAQRAFVEWLLAQ; (SEQ ID NO: 81)

Y-Aib-EGTFTSDYSIALDKΨPAQKEFVEWLLAA; (SEQ ID NO: 91)

Y-Aib-EGTFTSDYSIYLDKΨPAQRAFVEWLLAE; (SEQ ID NO: 93)
or

Y-Aib-EGTFTSDYSIALDKΨPAQRAFVEWLLAE. (SEQ ID NO: 94)

Residues 1-29 of Formula I may have the sequence:

Y-Aib-EGTFTSDYSIYLDK-K([17-carboxy-heptadecanoyl]-isoGlu-Peg3-Peg3)-AQRAFVEWLLAQ; (SEQ ID NO: 130)

Y-Aib-EGTFTSDYSIYLDK-K([19-Carboxy-nonadecanoyl]-isoGlu-Peg3-Peg3)-AQRAFVEWLLAQ; (SEQ ID NO: 131)

Y-Aib-EGTFTSDYSIYLDK-K([17-carboxy-heptadecanoyl]-isoGlu)-AQRAFVEWLLAQ; (SEQ ID NO: 132)

Y-Aib-EGTFTSDYSIYLDK-K([17-carboxy-heptadecanoyl]-isoGlu-GSGSGG)-AQRAFVEWLLAQ; (SEQ ID NO: 133)

Y-Aib-EGTFTSDYSIYLDK-K([17-carboxy-heptadecanoyl]-Peg3-Peg3)-AQRAFVEWLLAQ; (SEQ ID NO: 134)

Y-Aib-EGTFTSDYSIYLDK-K([17-carboxy-heptadecanoyl]-isoGlu-Peg3-Peg3-Peg3)-AQRAFVEWLLAQ; (SEQ ID NO: 135)

Y-Aib-EGTFTSDYSIYLDK-K([17-carboxy-heptadecanoyl]-Dapa-Peg3-Peg3)-AQRAFVEWLLAQ; (SEQ ID NO: 136)

Y-Aib-EGTFTSDYSIYLDK-K([19-Carboxy-nonadecanoyl]-isoGlu-Peg3-Peg3-Peg3)-AQRAFVEWLLAQ; (SEQ ID NO: 137)

Y-DAla-EGTFTSDYSIYLDK-K([17-carboxy-heptadecanoyl]-isoGlu-Peg3-Peg3)-AQRAFVEWLLAQ; (SEQ ID NO: 138)

Y-Aib-EGTFTSDYSIYLEK-K([17-carboxy-heptadecanoyl]-isoGlu-Peg3-Peg3)-AAKEFVEWLLSA; (SEQ ID NO: 139)

Y-Aib-EGTFTSDYSI-Aib-LDK-K([17-carboxy-heptadecanoyl]-isoGlu-Peg3-Peg3)-AQRAFVEWLLAQ; (SEQ ID NO: 140)

Y-Aib-EGTFTSDYSIYLDK-K([17-carboxy-heptadecanoyl]-isoGlu-Peg3-Peg3)-AQRAFVNWLLA-Aib; (SEQ ID NO: 141)

Y-Aib-EGTFTSDYSIYLDE-K([17-carboxy-heptadecanoyl]-isoGlu-Peg3-Peg3)-AAKEFIEWLESA; (SEQ ID NO: 13)

Y-Aib-EGTFTSDYSIALDK-K([17-carboxy-heptadecanoyl]-isoGlu-Peg3-Peg3)-AQRAFVNWLVA-Aib; (SEQ ID NO: 142)

Y-Aib-EGTFTSDYSIALDK-K[19-carboxy-nonadecanoyl]-isoGlu-Peg3-Peg3)-AQRAFVNWLVA-Aib; (SEQ ID NO: 143)

Y-Aib-EGTFTSDYSIALEK-K([17-carboxy-heptadecanoyl]-isoGlu-Peg3-Peg3)-AQRAFVEWLLAQ; (SEQ ID NO: 144)

Y-Aib-EGTFTSDLSIALEK-K([17-carboxy-heptadecanoyl]-isoGlu-Peg3-Peg3)-AQRAFVEWLLAQ; (SEQ ID NO: 145)

Y-Aib-EGTFTSDYSIYLEK-K([17-carboxy-heptadecanoyl]-isoGlu-Peg3-Peg3)-AQRAFVEWLLRA; (SEQ ID NO: 18)

Y-Aib-EGTFTSDLSIALDK-K([17-carboxy-heptadecanoyl]-isoGlu-Peg3-Peg3)-AQRAFVNWLVA-Aib; (SEQ ID NO: 146)

(SEQ ID NO: 147)
Y-Aib-EGTFTSDYSIALDK-K([17-carboxy-heptadecanoyl]-isoGlu-Peg3-Peg3)-AQRAFVEWLVA-Aib;

(SEQ ID NO: 148)
Y-Aib-EGTFTSDYSIALEK-K([17-carboxy-heptadecanoyl]-isoGlu-Peg3-Peg3)-AQRAFVEWLEAQ;

(SEQ ID NO: 149)
Y-Aib-EGTFTSDLSIALEK-K([17-carboxy-heptadecanoyl]-isoGlu-Peg3-Peg3)-AQRAFVEWLEAQ;

(SEQ ID NO: 150)
Y-Aib-EGTFTSDYSIALEK-K[19-carboxy-nonadecanoyl]-isoGlu-Peg3-Peg3)-AQRAFVEWLLAQ;

(SEQ ID NO: 151)
Y-Aib-EGTFTSDLSIALEK-K[19-carboxy-nonadecanoyl]-isoGlu-Peg3-Peg3)-AQRAFVEWLEAQ;
or (SEQ ID NO:152)
Y-Aib-EGTFTSDLSIALEK-K([19-carboxy-nonadecanoyl]-isoGlu-Peg3-Peg3)-AQRAFVEWLLAQ;

(SEQ ID NO: 28)
Y-Aib-EGTFTSDYSIYLEK-K([19-carboxy-nonadecanoyl]-isoGlu-Peg3-Peg3)-AQRAFVEWLLRA;

(SEQ ID NO: 153)
Y-DAla-EGTFTSDYSIYLDK-K([19-carboxy-nonadecanoyl]-isoGlu-Peg3-Peg3)-AQRAFVEWLLAQ;

(SEQ ID NO: 154)
Y-Aib-EGTFTSDYSIALEK-K([19-carboxy-nonadecanoyl]-isoGlu-Peg3-Peg3)-AQRAFVEWLLAQ;

(SEQ ID NO: 155)
Y-DAla-EGTFTSDYSIALEK-K([19-carboxy-nonadecanoyl]-isoGlu-Peg3-Peg3)-AQRAFVEWLLAQ;

(SEQ ID NO: 152)
Y-Aib-EGTFTSDLSIALEK-K([19-carboxy-nonadecanoyl]-isoGlu-Peg3-Peg3)-AQRAFVEWLLAQ;

(SEQ ID NO: 156)
Y-Aib-EGTFTSDYSIYLDK-K([19-carboxy-nonadecanoyl]-Peg3-Peg3)-AQRAFVEWLLAQ;

(SEQ ID NO: 157)
Y-Aib-EGTFTSDYSIYLDK-K([19-carboxy-nonadecanoyl]-IsoGlu)-AQRAFVEWLLAQ;

(SEQ ID NO: 158)
Y-Aib-EGTFTSDYSIYLDK-K([19-carboxy-nonadecanoyl]-Dapa-Peg3-Peg3)-AQRAFVEWLLAQ;

(SEQ ID NO: 24)
Y-Aib-EGTFTSDLSIALEK-K([17-carboxy-heptadecanoyl]-isoGlu-Peg3-Peg3)-AQRAFVEWLEAQK;

(SEQ ID NO: 159)
Y-Aib-EGTFTSDYSIALDK-K([19-carboxy-nonadecanoyl]-isoGlu-Peg3-Peg3)-AQRAFVEWLLAQ;

(SEQ ID NO: 160)
Y-DAla-EGTFTSDYSIALDK-K([19-carboxy-nonadecanoyl]-isoGlu-Peg3-Peg3)-AQRAFVEWLLAQ;

(SEQ ID NO: 161)
Y-Aib-EGTFTSDYSIALDK-K([19-carboxy-nonadecanoyl]-isoGlu-Peg3-Peg3)-AQRAFVEWLLAA;

(SEQ ID NO: 162)
Y-Aib-EGTFTSDYSIALDK-K([19-carboxy-nonadecanoyl]-isoGlu-Peg3-Peg3)-AAKEFVEWLLSA;

(SEQ ID NO: 163)
Y-Aib-EGTFTSDYSIALDE-K([19-carboxy-nonadecanoyl]-isoGlu-Peg3-Peg3)-AQRAFVEWLLAQ;

(SEQ ID NO: 164)
Y-Aib-EGTFTSDYSIALDE-K([19-carboxy-nonadecanoyl]-isoGlu-Peg3-Peg3)-AQRAFVEWLLAA;

(SEQ ID NO: 165)
Y-Aib-EGTFTSDYSIALDK-K([19-carboxy-nonadecanoyl]-isoGlu-Peg3-Peg3)-AQKAFVEWLLAA;

(SEQ ID NO: 166)
Y-Aib-EGTFTSDYSIYLDK-K([19-carboxy-nonadecanoyl]-isoGlu-Peg3-Peg3)-AQREFVEWLLAQ;

(SEQ ID NO: 167)
Y-Aib-EGTFTSDYSIALDK-K([19-carboxy-nonadecanoyl]-isoGlu-Peg3-Peg3)-AQREFVEWLLAQ;

(SEQ ID NO: 168)
Y-Aib-EGTFTSDYSIALDK-K([19-carboxy-nonadecanoyl]-isoGlu-Peg3-Peg3)-AQKEFVEWLLAQ;

(SEQ ID NO: 169)
Y-Aib-EGTFTSDYSIALDK-K([19-carboxy-nonadecanoyl]-isoGlu-Peg3-Peg3)-AQKEFVEWLLAA;

(SEQ ID NO: 170)
Y-Aib-EGTFTSDYSIALDK-K([19-carboxy-nonadecanoyl]-isoGlu-Peg3-Peg3)-AQRAFIEWLLAQ;

(SEQ ID NO: 171)
Y-Aib-EGTFTSDYSIALDK-K([17-carboxy-heptadecanoyl]-isoGlu-Peg3-Peg3)-AQRAFVEWLLAQ;

(SEQ ID NO: 172)
Y-Aib-EGTFTSDYSIALDK-K((19-Carboxy-nonadecanoyl)-[(Piperazine-1-yl)-acetyl]-Peg3-Peg3)-AQRAFVEWLLAQ;
or (SEQ ID NO: 173)
Y-Aib-EGTFTSDYSIALDK-K((19-Carboxy-nonadecanoyl)-[(Piperazine-1-yl)-acetyl]-Peg3-Peg3)-AQKEFVEWLLAA.

The peptide backbone of Formula I may have the sequence:

Y-Aib-EGTFTSDYSIYLDKΨPAQRAFVEWLLAQGPSSGAPPPS; (SEQ ID NO: 95)

Y-DAla-EGTFTSDYSIYLDKΨPAQRAFVEWLLAQGPSSGAPPPS; (SEQ ID NO: 96)

Y-Aib-EGTFTSDYSIYLEKΨPAAKEFVEWLLSAGPSSGAPPPS; (SEQ ID NO: 97)

Y-Aib-EGTFTSDYSI-Aib-LDKΨPAQRAFVEWLLAQGPSSGAPPPS; (SEQ ID NO: 98)

Y-Aib-EGTFTSDYSIYLDKΨPAQRAFVNWLLA-Aib-K; (SEQ ID NO: 99)

Y-Aib-EGTFTSDYSIYLDEΨPAAKEFIEWLESA; (SEQ ID NO: 71)

Y-Aib-EGTFTSDYSIALDKΨPAQRAFVNWLVA-Aib-KPSSGAPPPS; (SEQ ID NO: 100)

Y-Aib-EGTFTSDYSIALEKΨPAQRAFVEWLLAQK; (SEQ ID NO: 101)

Y-Aib-EGTFTSDLSIALEKΨPAQRAFVEWLLAQK; (SEQ ID NO: 102)

Y-Aib-EGTFTSDYSIYLEKΨPAQRAFVEWLLRA; (SEQ ID NO: 75)

Y-Aib-EGTFTSDYSIALDKΨPAQRAFVNWLVA-Aib-K; (SEQ ID NO: 103)

Y-Aib-EGTFTSDLSIALDKΨPAQRAFVNWLVA-Aib-K; (SEQ ID NO: 104)

Y-Aib-EGTFTSDYSIALDKΨPAQRAFVEWLVA-Aib-K; (SEQ ID NO: 105)

Y-Aib-EGTFTSDYSIALEKΨPAQRAFVEWLEAQGPSSGAPPPS; (SEQ ID NO: 106)

Y-Aib-EGTFTSDYSIALEKΨPAQRAFVEWLEAQK; (SEQ ID NO: 107)

Y-Aib-EGTFTSDYSIALEKΨPAQRAFVEWLLAQGPSSGAPPPS; (SEQ ID NO: 109)

Y-DAla-EGTFTSDYSIALEKΨPAQRAFVEWLLAQGPSSGAPPPS; (SEQ ID NO: 110)

Y-Aib-EGTFTSDLSIALEKΨPAQRAFVEWLLAQKPSSGAPPPS; (SEQ ID NO: 111)

Y-Aib-EGTFTSDYSIALDKΨPAQRAFVEWLLAQKPSSGAPPPS; (SEQ ID NO: 112)

Y-DAla-EGTFTSDYSIALDKΨPAQRAFVEWLLAQKPSSGAPPPS; (SEQ ID NO: 113)

Y-Aib-EGTFTSDYSIALDKΨPAQRAFVEWLLAAPSSGAPPPS; (SEQ ID NO: 114)

Y-Aib-EGTFTSDYSIALDKΨPAAKEFVEWLLSAGPSSGAPPPS; (SEQ ID NO: 115)

Y-Aib-EGTFTSDYSIALDKΨPAQRAFVEWLLAQGPSSGAPPPS; (SEQ ID NO: 116)

Y-Aib-EGTFTSDYSIALDEΨPAQRAFVEWLLAQGPSSGAPPPS; (SEQ ID NO: 117)

Y-Aib-EGTFTSDYSIALDEΨPAQRAFVEWLLAAGPSSGAPPPS; (SEQ ID NO: 118)

Y-Aib-EGTFTSDYSIALDKΨPAQKAFVEWLLAAGPSSGAPPPS; (SEQ ID NO: 119)

Y-Aib-EGTFTSDYSIYLDKΨPAQREFVEWLLAQGPSSGAPPPS; (SEQ ID NO: 120)

Y-Aib-EGTFTSDYSIALDKΨPAQREFVEWLLAQGPSSGAPPPS; (SEQ ID NO: 121)

Y-Aib-EGTFTSDYSIALDKΨPAQKEFVEWLLAQGPSSGAPPPS; (SEQ ID NO: 122)

Y-Aib-EGTFTSDYSIALDKΨPAQKEFVEWLLAAGPSSGAPPPS; (SEQ ID NO: 123)

Y-Aib-EGTFTSDYSIALDKΨPAQRAFIEWLLAQGPSSGAPPPS; (SEQ ID NO: 124)

Y-Aib-EGTFTSDYSIALDKΨPAQRAFVEWLLAQGPSSGAPPP; (SEQ ID NO: 125)

Y-Aib-EGTFTSDYSIALDKΨPAQRAFVEWLLAQGPSSGAPPPS; (SEQ ID NO: 116)

Y-Aib-EGTFTSDYSIALDKΨPAQKEFVEWLLAAGPSSGAPPPS; (SEQ ID NO: 123)

Y-Aib-EGTFTSDLSIALEKΨPAQRAFVEWLLAQGPSSGAPPPS; (SEQ ID NO: 126)

Y-Aib-EGTFTSDYSIYLDKΨPAQRAFVEWLLAEGPSSGAPPPS; (SEQ ID NO: 127)

Y-Aib-EGTFTSDYSIALDKΨPAQRAFVEWLLAEGPSSGAPPPS; (SEQ ID NO: 128)

or

Y-Aib-EGTFTSDYSIALDKΨAQRAFVEWLLAEPSSGAPPPS. (SEQ ID NO: 129)

The peptide backbone of Formula I may have the sequence:

Y-Aib-EGTFTSDYSIYLDK-K([17-carboxy-heptadecanoyl]-isoGlu-Peg3-Peg3)-AQRAFVEWLLAQGPSSGAPPPS; (SEQ ID NO: 1)

Y-Aib-EGTFTSDYSIYLDK-K([19-Carboxy-nonadecanoyl]-isoGlu-Peg3-Peg3)-AQRAFVEWLLAQGPSSGAPPPS; (SEQ ID NO: 2)

Y-Aib-EGTFTSDYSIYLDK-K([17-carboxy-heptadecanoyl]-isoGlu)-AQRAFVEWLLAQGPSSGAPPPS; (SEQ ID NO: 3)

HY-Aib-EGTFTSDYSIYLDK-K([17-carboxy-heptadecanoyl]-isoGlu-GSGSGG)-AQRAFVEWLLAQGPSSGAPPPS; (SEQ ID NO: 177)

Y-Aib-EGTFTSDYSIYLDK-K([17-carboxy-heptadecanoyl]-Peg3-Peg3)-AQRAFVEWLLAQGPSSGAPPPS; (SEQ ID NO: 5)

Y-Aib-EGTFTSDYSIYLDK-K([17-carboxy-heptadecanoyl]-isoGlu-Peg3-Peg3-Peg3)-AQRAFVEWLLAQGPSSGAPPPS; (SEQ ID NO: 6)

Y-Aib-EGTFTSDYSIYLDK-K([17-carboxy-heptadecanoyl]-Dapa-Peg3-Peg3)-AQRAFVEWLLAQGPSSGAPPPS; (SEQ ID NO: 7)

Y-Aib-EGTFTSDYSIYLDK-K([19-Carboxy-nonadecanoyl]-isoGlu-Peg3-Peg3-Peg3)-AQRAFVEWLLAQGPSSGAPPPS; (SEQ ID NO: 8)

-continued (SEQ ID NO: 9)
Y-DAla-EGTFTSDYSIYLDK-K([17-carboxy-hepta-
decanoyl]-isoGlu-Peg3-Peg3)-AQRAFVEWLLAQGPSSGAPPP
S;

(SEQ ID NO: 10)
Y-Aib-EGTFTSDYSIYLEK-K([17-carboxy-heptadecanoyl]-
isoGlu-Peg3-Peg3)-AAKEFVEWLLSAGPSSGAPPPS;

(SEQ ID NO: 11)
Y-Aib-EGTFTSDYSI-Aib-LDK-K([17-carboxy-hepta
decanoyl]-isoGlu-Peg3-Peg3)-AQRAFVEWLLAQGPSSGAPPP
S;

(SEQ ID NO: 12)
Y-Aib-EGTFTSDYSIYLDK-K([17-carboxy-heptadecanoyl]-
isoGlu-Peg3-Peg3)-AQRAFVNWLLA-Aib-K;

(SEQ ID NO: 13)
Y-Aib-EGTFTSDYSIYLDE-K([17-carboxy-heptadecanoyl]-
isoGlu-Peg3-Peg3)-AAKEFIEWLESA;

(SEQ ID NO: 14)
Y-Aib-EGTFTSDYSIALDK-K([17-carboxy-heptadecanoyl]-
isoGlu-Peg3-Peg3)-AQRAFVNWLVA-Aib-KPSSGAPPPS;

(SEQ ID NO: 15)
Y-Aib-EGTFTSDYSIALDK-K[19-carboxy-nonadecanoyl]-
isoGlu-Peg3-Peg3)-AQRAFVNWLVA-Aib-KPSSGAPPPS;

(SEQ ID NO: 16)
Y-Aib-EGTFTSDYSIALEK-K([17-carboxy-heptadecanoyl]-
isoGlu-Peg3-Peg3)-AQRAFVEWLLAQK;

(SEQ ID NO: 17)
Y-Aib-EGTFTSDLSIALEK-K([17-carboxy-heptadecanoyl]-
isoGlu-Peg3-Peg3)-AQRAFVEWLLAQK;

(SEQ ID NO: 18)
Y-Aib-EGTFTSDYSIYLEK-K([17-carboxy-heptadecanoyl]-
isoGlu-Peg3-Peg3)-AQRAFVEWLLRA;

(SEQ ID NO: 19)
Y-Aib-EGTFTSDYSIALDK-K([17-carboxy-heptadecanoyl]-
isoGlu-Peg3-Peg3)-AQRAFVNWLVA-Aib-K;

(SEQ ID NO: 20)
Y-Aib-EGTFTSDLSIALDK-K([17-carboxy-heptadecanoyl]-
isoGlu-Peg3-Peg3)-AQRAFVNWLVA-Aib-K;

(SEQ ID NO: 21)
Y-Aib-EGTFTSDYSIALDK-K([17-carboxy-heptadecanoyl]-
isoGlu-Peg3-Peg3)-AQRAFVEWLVA-Aib-K;

(SEQ ID NO: 22)
Y-Aib-EGTFTSDYSIALEK-K([17-carboxy-heptadecanoyl]-
isoGlu-Peg3-Peg3)-AQRAFVEWLEAQGPSSGAPPPS;

(SEQ ID NO: 23)
Y-Aib-EGTFTSDYSIALEK-K([17-carboxy-heptadecanoyl]-
isoGlu-Peg3-Peg3)-AQRAFVEWLEAQK;

(SEQ ID NO: 25)
Y-Aib-EGTFTSDYSIALEK-K[19-carboxy-nonadecanoyl]-
isoGlu-Peg3-Peg3)-AQRAFVEWLLAQK;

(SEQ ID NO: 26)
Y-Aib-EGTFTSDLSIALEK-K[19-carboxy-nonadecanoyl]-
isoGlu-Peg3-Peg3)-AQRAFVEWLEAQK;

(SEQ ID NO: 22)
Y-Aib-EGTFTSDYSIALEK-K([17-carboxy-heptadecanoyl]-
isoGlu-Peg3-Peg3)-AQRAFVEWLEAQGPSSGAPPPS;

(SEQ ID NO: 27)
Y-Aib-EGTFTSDLSIALEK-K([19-carboxy-nonadecanoyl]-
isoGlu-Peg3-Peg3)-AQRAFVEWLLAQK;

(SEQ ID NO: 28)
Y-Aib-EGTFTSDYSIYLEK-K([19-carboxy-nonadecanoyl]-
isoGlu-Peg3-Peg3)-AQRAFVEWLLRA;

(SEQ ID NO: 29)
Y-DAla-EGTFTSDYSIYLDK-K([19-carboxy-nonadecanoyl]-
isoGlu-Peg3-Peg3)-AQRAFVEWLLAQGPSSGAPPPS;

(SEQ ID NO: 30)
Y-Aib-EGTFTSDYSIALEK-K([19-carboxy-nonadecanoyl]-
isoGlu-Peg3-Peg3)-AQRAFVEWLLAQGPSSGAPPPS;

(SEQ ID NO: 31)
Y-DAla-EGTFTSDYSIALEK-K([19-carboxy-nonadecanoyl]-
isoGlu-Peg3-Peg3)-AQRAFVEWLLAQGPSSGAPPPS;

(SEQ ID NO: 33)
Y-Aib-EGTFTSDLSIALEK-K([19-carboxy-nonadecanoyl]-
isoGlu-Peg3-Peg3)-AQRAFVEWLLAQKPSSGAPPPS;

(SEQ ID NO: 34)
Y-Aib-EGTFTSDYSIYLDK-K([19-carboxy-nonadecanoyl]-
Peg3-Peg3)-AQRAFVEWLLAQGPSSGAPPPS;

(SEQ ID NO: 35)
Y-Aib-EGTFTSDYSIYLDK-K([19-carboxy-nonadecanoyl]-
isoGlu)-AQRAFVEWLLAQGPSSGAPPPS;

(SEQ ID NO: 36)
Y-Aib-EGTFTSDYSIYLDK-K([19-carboxy-nonadecanoyl]-
Dapa-Peg3-Peg3)-AQRAFVEWLLAQGPSSGAPPPS;

(SEQ ID NO: 24)
Y-Aib-EGTFTSDLSIALEK-K([17-carboxy-heptadecanoyl]-
isoGlu-Peg3-Peg3)-AQRAFVEWLEAQK;

(SEQ ID NO: 32)
Y-Aib-EGTFTSDLSIALEK-K([19-carboxy-nonadecanoyl]-
isoGlu-Peg3-Peg3)-AQRAFVEWLLAQGPSSGAPPPS;

(SEQ ID NO: 37)
Y-Aib-EGTFTSDYSIALDK-K([19-carboxy-nonadecanoyl]-
isoGlu-Peg3-Peg3)-AQRAFVEWLLAQKPSSGAPPPS;

(SEQ ID NO: 38)
Y-DAla-EGTFTSDYSIALDK-K([19-carboxy-nonadecanoyl]-
isoGlu-Peg3-Peg3)-AQRAFVEWLLAQKPSSGAPPPS;

(SEQ ID NO: 39)
Y-Aib-EGTFTSDYSIALDK-K([19-carboxy-nonadecanoyl]-isoGlu-Peg3-Peg3)-AQRAFVEWLLAAPSSGAPPPS;

(SEQ ID NO: 40)
Y-Aib-EGTFTSDYSIALDK-K([19-carboxy-nonadecanoyl]-isoGlu-Peg3-Peg3)-AAKEFVEWLLSAGPSSGAPPPS;

(SEQ ID NO: 41)
Y-Aib-EGTFTSDYSIALDK-K([19-carboxy-nonadecanoyl]-isoGlu-Peg3-Peg3)-AQRAFVEWLLAQGPSSGAPPPS;

(SEQ ID NO: 42)
Y-Aib-EGTFTSDYSIALDE-K([19-carboxy-nonadecanoyl]-isoGlu-Peg3-Peg3)-AQRAFVEWLLAQGPSSGAPPPS;

(SEQ ID NO: 43)
Y-Aib-EGTFTSDYSIALDE-K([19-carboxy-nonadecanoyl]-isoGlu-Peg3-Peg3)-AQRAFVEWLLAAGPSSGAPPPS;

(SEQ ID NO: 44)
Y-Aib-EGTFTSDYSIALDK-K([19-carboxy-nonadecanoyl]-isoGlu-Peg3-Peg3)-AQKAFVEWLLAAGPSSGAPPPS;

(SEQ ID NO: 45)
Y-Aib-EGTFTSDYSIYLDK-K([19-carboxy-nonadecanoyl]-isoGlu-Peg3-Peg3)-AQREFVEWLLAQGPSSGAPPPS;

(SEQ ID NO: 46)
Y-Aib-EGTFTSDYSIALDK-K([19-carboxy-nonadecanoyl]-isoGlu-Peg3-Peg3)-AQREFVEWLLAQGPSSGAPPPS;

(SEQ ID NO: 47)
Y-Aib-EGTFTSDYSIALDK-K([19-carboxy-nonadecanoyl]-isoGlu-Peg3-Peg3)-AQKEFVEWLLAQGPSSGAPPPS;

(SEQ ID NO: 48)
Y-Aib-EGTFTSDYSIALDK-K([19-carboxy-nonadecanoyl]-isoGlu-Peg3-Peg3)-AQKEFVEWLLAAGPSSGAPPPS;

(SEQ ID NO: 49)
Y-Aib-EGTFTSDYSIALDK-K([19-carboxy-nonadecanoyl]-isoGlu-Peg3-Peg3)-AQRAFIEWLLAQGPSSGAPPPS;

(SEQ ID NO: 50)
Y-Aib-EGTFTSDYSIALDK-K([17-carboxy-heptadecanoyl]-isoGlu-Peg3-Peg3)-AQRAFVEWLLAQGPSSGAPPPS;

(SEQ ID NO: 51)
Y-Aib-EGTFTSDYSIALDK-K((19-Carboxy-nonadecanoyl)-[(Piperazine-1-yl)-acetyl]-Peg3-Peg3)-AQRAFVEWLLAQGPSSGAPPPS;

(SEQ ID NO: 52)
Y-Aib-EGTFTSDYSIALDK-K((19-Carboxy-nonadecanoyl)-[(Piperazine-1-yl)-acetyl]-Peg3-Peg3)-AQKEFVEWLLAAGPSSGAPPPS;

(SEQ ID NO: 53)
Y-Aib-EGTFTSDYSIYLDK-K([19-Carboxy-nonadecanoyl]-isoGlu-Peg3-Peg3)-AQRAFVEWLLAEGPSSGAPPPS, (SEQ ID NO: 54)
Y-Aib-EGTFTSDYSIALDK-K([19-carboxy-nonadecanoyl]-isoGlu-Peg3-Peg3)-AQRAFVEWLLAEGPSSGAPPPS;
or (SEQ ID NO: 55)
Y-Aib-EGTFTSDYSIALDK-K([19-carboxy-nonadecanoyl]-isoGlu-Peg3-Peg3)-AQRAFVEWLLAEPSSGAPPPS.

The peptide backbone of Formula I may have the sequence:

(SEQ ID No: 180)
H-Y-Aib-EGTFTSDYSIYLDK-K([17-carboxy-heptadecanoyl]-isoGlu-Peg3-Peg3)-AQRAFVEWLLAQGPSSGAPPPS-NH$_2$, (SEQ ID No: 181)
H-Y-Aib-EGTFTSDYSIYLDK-K([19-Carboxy-nonadecanoyl]-isoGlu-Peg3-Peg3)-AQRAFVEWLLAQGPSSGAPPPS-NH$_2$, (SEQ ID No: 182)
H-Y-Aib-EGTFTSDYSIYLDK-K([17-carboxy-heptadecanoyl]-isoGlu)-AQRAFVEWLLAQGPSSGAPPPS-NH$_2$, (SEQ ID NO: 183)
H-H-Y-Aib-EGTFTSDYSIYLDK-K([17-carboxy-heptadecanoyl]-isoGlu-GSGSGG)-AQRAFVEWLLAQGPSSGAPPPS-NH$_2$;

(SEQ ID NO: 184)
H-Y-Aib-EGTFTSDYSIYLDK-K([17-carboxy-heptadecanoyl]-Peg3-Peg3)-AQRAFVEWLLAQGPSSGAPPPS-NH$_2$;

(SEQ ID NO: 185)
H-H-Y-Aib-EGTFTSDYSIYLDK-K([17-carboxy-heptadecanoyl]-isoGlu-Peg3-Peg3-Peg3)-AQRAFVEWLLAQGPSSGAPPPS-NH$_2$;

(SEQ ID NO: 186)
H-Y-Aib-EGTFTSDYSIYLDK-K([17-carboxy-heptadecanoyl]-Dapa-Peg3-Peg3)-AQRAFVEWLLAQGPSSGAPPPS-NH$_2$;

(SEQ ID NO: 187)
H-Y-Aib-EGTFTSDYSIYLDK-K([19-Carboxy-nonadecanoyl]-isoGlu-Peg3-Peg3)-AQRAFVEWLLAQGPSSGAPPPS-NH$_2$;

(SEQ ID NO: 188)
H-Y-DAla-EGTFTSDYSIYLDK-K([17-carboxy-heptadecanoyl]-isoGlu-Peg3-Peg3)-AQRAFVEWLLAQGPSSGAPPPS-NH$_2$;

(SEQ ID NO: 189)
H-Y-Aib-EGTFTSDYSIYLEK-K([17-carboxy-hepta-decanoyl]-isoGlu-Peg3-Peg3)-AAKEFVEWLLSAGPSSGAPPPS-NH$_2$;

(SEQ ID NO: 190)
H-Y-Aib-EGTFTSDYSI-Aib-LDK-K([17-carboxy-hepta-decanoyl]-isoGlu-Peg3-Peg3)-AQRAFVEWLLAQGPSSGAPPPS-NH$_2$;

(SEQ ID NO: 191)
H-Y-Aib-EGTFTSDYSIYLDK-K([17-carboxy-hepta-decanoyl]-isoGlu-Peg3-Peg3)-AQRAFVNWLLA-Aib-K-NH$_2$;

(SEQ ID NO: 192)
H-Y-Aib-EGTFTSDYSIYLDE-K([17-carboxy-hepta-decanoyl]-isoGlu-Peg3-Peg3)-AAKEFIEWLESA-NH$_2$;

(SEQ ID NO: 193)
H-Y-Aib-EGTFTSDYSIALDK-K([17-carboxy-hepta-decanoyl]-isoGlu-Peg3-Peg3)-AQRAFVNWLVA-Aib-KPSSGAPPPS-NH$_2$;

(SEQ ID NO: 194)
H-Y-Aib-EGTFTSDYSIALDK-K[19-carboxy-nonadecanoyl]-isoGlu-Peg3-Peg3)-AQRAFVNWLVA-Aib-KPSSGAPPPS-NH$_2$;

(SEQ ID NO: 195)
H-Y-Aib-EGTFTSDYSIALEK-K([17-carboxy-hepta-decanoyl]-isoGlu-Peg3-Peg3)-AQRAFVEWLLAQK-NH$_2$;

(SEQ ID NO: 196)
H-Y-Aib-EGTFTSDLSIALEK-K([17-carboxy-hepta-decanoyl]-isoGlu-Peg3-Peg3)-AQRAFVEWLLAQK-NH$_2$;

(SEQ ID NO: 197)
H-Y-Aib-EGTFTSDYSIYLEK-K([17-carboxy-hepta-decanoyl]-isoGlu-Peg3-Peg3)-AQRAFVEWLLRA-NH$_2$;

(SEQ ID NO: 198)
H-Y-Aib-EGTFTSDYSIALDK-K([17-carboxy-hepta-decanoyl]-isoGlu-Peg3-Peg3)-AQRAFVNWLVA-Aib-K-NH$_2$;

(SEQ ID NO: 199)
H-Y-Aib-EGTFTSDLSIALDK-K([17-carboxy-hepta-decanoyl]-isoGlu-Peg3-Peg3)-AQRAFVNWLVA-Aib-K-NH$_2$;

(SEQ ID NO: 200)
H-Y-Aib-EGTFTSDYSIALDK-K([17-carboxy-hepta-decanoyl]-isoGlu-Peg3-Peg3)-AQRAFVEWLVA-Aib-K-NH$_2$;

(SEQ ID NO: 201)
H-Y-Aib-EGTFTSDYSIALEK-K([17-carboxy-hepta-decanoyl]-isoGlu-Peg3-Peg3)-AQRAFVEWLEAQGPSSGAPPPS-NH$_2$;

(SEQ ID NO: 202)
H-Y-Aib-EGTFTSDYSIALEK-K([17-carboxy-hepta-decanoyl]-isoGlu-Peg3-Peg3)-AQRAFVEWLEAQK-NH$_2$;

(SEQ ID NO: 204)
H-Y-Aib-EGTFTSDYSIALEK-K[19-carboxy-nonadecanoyl]-isoGlu-Peg3-Peg3)-AQRAFVEWLLAQK-NH$_2$;

(SEQ ID NO: 205)
H-Y-Aib-EGTFTSDLSIALEK-K[19-carboxy-nonadecanoyl]-isoGlu-Peg3-Peg3)-AQRAFVEWLEAQK-NH$_2$;

(SEQ ID NO: 206)
H-Y-Aib-EGTFTSDLSIALEK-K([19-carboxy-nona-decanoyl]-isoGlu-Peg3-Peg3)-AQRAFVEWLLAQK-NH$_2$;

(SEQ ID NO: 207)
H-Y-Aib-EGTFTSDYSIYLEK-K([19-carboxy-nona-decanoyl]-isoGlu-Peg3-Peg3)-AQRAFVEWLLRA-NH$_2$;

(SEQ ID NO: 208)
H-Y-DAla-EGTFTSDYSIYLDK-K([19-carboxy-nona-decanoyl]-isoGlu-Peg3-Peg3)-AQRAFVEWLLAQGPSSGAPPPS-NH$_2$;

(SEQ ID NO: 209)
H-Y-Aib-EGTFTSDYSIALEK-K([19-carboxy-nona-decanoyl]-isoGlu-Peg3-Peg3)-AQRAFVEWLLAQGPSSGAPPPS-NH$_2$;

(SEQ ID NO: 210)
H-Y-DAla-EGTFTSDYSIALEK-K([19-carboxy-nona-decanoyl]-isoGlu-Peg3-Peg3)-AQRAFVEWLLAQGPSSGAPPPS-NH$_2$;

(SEQ ID NO: 212)
H-Y-Aib-EGTFTSDLSIALEK-K([19-carboxy-nona-decanoyl]-isoGlu-Peg3-Peg3)-AQRAFVEWLLAQKPSSGAPPPS-NH$_2$;

(SEQ ID NO: 213)
H-Y-Aib-EGTFTSDYSIYLDK-K([19-carboxy-nona-decanoyl]-Peg3-Peg3)-AQRAFVEWLLAQGPSSGAPPPS-NH$_2$;

(SEQ ID NO: 214)
H-Y-Aib-EGTFTSDYSIYLDK-K([19-carboxy-nona-decanoyl]-isoGlu)-AQRAFVEWLLAQGPSSGAPPPS-NH$_2$;

[[r]]

(SEQ ID NO: 215)
H-Y-Aib-EGTFTSDYSIYLDK-K([19-carboxy-nona-decanoyl]-Dapa-Peg3-Peg3)-AQRAFVEWLLAQGPSSGAPPPS-NH$_2$, (SEQ ID NO: 203)
H-Y-Aib-EGTFTSDLSIALEK-K([17-carboxy-hepta-decanoyl]-isoGlu-Peg3-Peg3)-AQRAFVEWLEAQK-NH$_2$, (SEQ ID NO: 211)
H-Y-Aib-EGTFTSDLSIALEK-K([19-carboxy-nona-decanoyl]-isoGlu-Peg3-Peg3)-AQRAFVEWLLAQGPSSGAPPPS-NH$_2$;

-continued (SEQ ID NO: 216)
H-Y-Aib-EGTFTSDYSIALDK-K([19-carboxy-nonadecanoyl]-isoGlu-Peg3-Peg3)-AQRAFVEWLLAQKPSSGAPPP

S-NH$_2$;

(SEQ ID NO: 217)
H-Y-DAla-EGTFTSDYSIALDK-K([19-carboxy-nonadecanoyl]-isoGlu-Peg3-Peg3)-AQRAFVEWLLAQKPSSGAPPP

S-NH$_2$;

(SEQ ID NO: 218)
H-Y-Aib-EGTFTSDYSIALDK-K([19-carboxy-nonadecanoyl]-isoGlu-Peg3-Peg3)-AQRAFVEWLLAAPSSGAPPP

S-NH$_2$;

(SEQ ID NO: 219)
H-Y-Aib-EGTFTSDYSIALDK-K([19-carboxy-nonadecanoyl]-isoGlu-Peg3-Peg3)-AAKEFVEWLLSAGPSSGAPPP

S-NH$_2$;

(SEQ ID NO: 220)
H-Y-Aib-EGTFTSDYSIALDK-K([19-carboxy-nonadecanoyl]-isoGlu-Peg3-Peg3)-AQRAFVEWLLAQGPSSGAPPP

S-NH$_2$;

(SEQ ID NO: 221)
H-Y-Aib-EGTFTSDYSIALDE-K([19-carboxy-nonadecanoyl]-isoGlu-Peg3-Peg3)-AQRAFVEWLLAQGPSSGAPPP

S-NH$_2$;

(SEQ ID NO: 222)
H-Y-Aib-EGTFTSDYSIALDE-K([19-carboxy-nonadecanoyl]-isoGlu-Peg3-Peg3)-AQRAFVEWLLAAGPSSGAPPP

S-NH$_2$;

(SEQ ID NO: 223)
H-Y-Aib-EGTFTSDYSIALDK-K([19-carboxy-nonadecanoyl]-isoGlu-Peg3-Peg3)-AQKAFVEWLLAAGPSSGAPPP

S-NH$_2$;

(SEQ ID NO: 224)
H-Y-Aib-EGTFTSDYSIYLDK-K([19-carboxy-nonadecanoyl]-isoGlu-Peg3-Peg3)-AQREFVEWLLAQGPSSGAPPP

S-NH$_2$;

(SEQ ID NO: 225)
H-Y-Aib-EGTFTSDYSIALDK-K([19-carboxy-nonadecanoyl]-isoGlu-Peg3-Peg3)-AQREFVEWLLAQGPSSGAPPP

S-NH$_2$;

(SEQ ID NO: 226)
H-Y-Aib-EGTFTSDYSIALDK-K([19-carboxy-nonadecanoyl]-isoGlu-Peg3-Peg3)-AQKEFVEWLLAQGPSSGAPPP

S-NH$_2$;

(SEQ ID NO: 227)
H-Y-Aib-EGTFTSDYSIALDK-K([19-carboxy-nonadecanoyl]-isoGlu-Peg3-Peg3)-AQKEFVEWLLAAGPSSGAPPP

S-NH$_2$;

(SEQ ID NO: 228)
H-Y-Aib-EGTFTSDYSIALDK-K([19-carboxy-nonadecanoyl]-isoGlu-Peg3-Peg3)-AQRAFIEWLLAQGPSSGAPPP

S-NH$_2$;

(SEQ ID NO: 229)
H-Y-Aib-EGTFTSDYSIALDK-K([17-carboxy-heptadecanoyl]-isoGlu-Peg3-Peg3)-AQRAFVEWLLAQGPSSGAPPP

S-NH$_2$;

(SEQ ID NO: 230)
H-Y-Aib-EGTFTSDYSIALDK-K((19-Carboxy-nonadecanoyl)-[(Piperazine-1-yl)-acetyl]-Peg3-

Peg3)-AQRAFVEWLLAQGPSSGAPPPS-NH$_2$;

(SEQ ID NO: 231)
H-Y-Aib-EGTFTSDYSIALDK-K((19-Carboxy-nonadecanoyl)-[(Piperazine-1-yl)-acetyl]-Peg3-

Peg3)-AQKEFVEWLLAAGPSSGAPPPS-NH$_2$;

(SEQ ID NO: 232)
H-Y-Aib-EGTFTSDYSIYLDK-K([19-Carboxy-nonadecanoyl]-isoGlu-Peg3-Peg3)-AQRAFVEWLLAEGPSSGAPPP

S-NH$_2$;

(SEQ ID NO: 233)
H-Y-Aib-EGTFTSDYSIALDK-K([19-carboxy-nonadecanoyl]-isoGlu-Peg3-Peg3)-AQRAFVEWLLAEGPSSGAPPP S-NH$_2$;
or (SEQ ID NO: 234)
H-Y-Aib-EGTFTSDYSIALDK-K([19-carboxy-nonadecanoyl]-isoGlu-Peg3-Peg3)-AQRAFVEWLLAEPSSGAPPP

S-NH$_2$.

Certain of the Y1 groups, when present, may provide increased stability in vivo, e.g. in serum, and so may contribute to the half life of the GIP analogue. Without wishing to be bound by theory, it is believed that these groups may help to stabilize the three dimensional conformation of the molecule and/or provide resistance to proteolytic degradation.

For example, the Y1 sequences Gly-Pro-Ser-Ser-Gly-Ala-Pro-Pro-Pro-Ser (SEQ ID NO: 57), Gly-Pro-Ser-Ser-Gly-Ala-Pro-Pro-Ser (SEQ ID NO: 59), Pro-Ser-Ser-Gly-Ala-Pro-Pro-Pro-Ser (SEQ ID NO: 60) and Pro-Ser-Ser-Gly-Ala-Pro-Pro-Ser (SEQ ID NO: 61) have homology with a C-terminal portion of the Exendin-4 molecule and appear to contribute to the stability of the molecule without concomitantly providing significant levels of GLP-1 agonist activity.

The invention further provides a pharmaceutical composition comprising a GIP analogue as described herein, or a pharmaceutically acceptable salt or solvate thereof, in admixture with a carrier, preferably a pharmaceutically acceptable carrier. The GIP analogue may, for example, be a pharmaceutically acceptable acid addition salt.

The pharmaceutical composition may be formulated as a liquid suitable for administration by injection or infusion, or which is formulated to cause slow release of said GIP analogue.

The invention further provides a therapeutic kit comprising a GIP analogue as described herein, and a device comprising a GIP analogue as described herein.

The invention further provides a GIP analogue as described herein, or a pharmaceutically acceptable salt or solvate thereof, for use in a method of medical treatment, e.g. for use in the treatment and/or prevention of a metabolic disorder.

The invention further provides the use of a GIP analogue as described herein, or a pharmaceutically acceptable salt or solvate thereof, in the preparation of a medicament for the treatment and/or prevention of a metabolic disorder.

The invention further provides a method of prevention and or/treatment of a metabolic disorder in a subject, comprising administering a GIP analogue as described herein, or a pharmaceutically acceptable salt or solvate thereof, to the subject.

The metabolic disorder may be diabetes or a diabetes related disorder, or obesity or an obesity related disorder. The link between obesity and diabetes is well known, so these conditions are not necessarily separate or mutually exclusive.

Diabetes related disorders include insulin resistance, glucose intolerance, increased fasting glucose, pre-diabetes, type 1 diabetes, type 2 diabetes, gestational diabetes hypertension, dyslipidemia, and combinations thereof.

Diabetes related disorders also include atherosclerosis, arteriosclerosis, coronary heart disease, peripheral artery disease and stroke; or conditions associated with atherogenic dyslipidemia, blood fat disorders, elevated blood pressure, hypertension, a prothrombotic state, bone related disorders and a proinflammatory state.

Bone related disorders include, but are not limited to, osteoporosis and increased risk of bone fracture.

The blood fat disorder may be selected from high triglycerides, low HDL cholesterol, high LDL cholesterol, and plaque buildup in artery walls, or a combination thereof.

The prothrombotic state may be selected from high fibrinogen levels in the blood and high plasminogen activator inhibitor-1 levels in the blood.

The proinflammatory state may be an elevated C-reactive protein level in the blood.

Obesity related disorders include obesity linked inflammation, obesity linked gallbladder disease and obesity induced sleep apnea, or may be associated with a condition selected from atherogenic dyslipidemia, blood fat disorders, elevated blood pressure, hypertension, a prothrombotic state, and a proinflammatory state, or a combination thereof.

DETAILED DESCRIPTION OF THE INVENTION

Figure 1A:
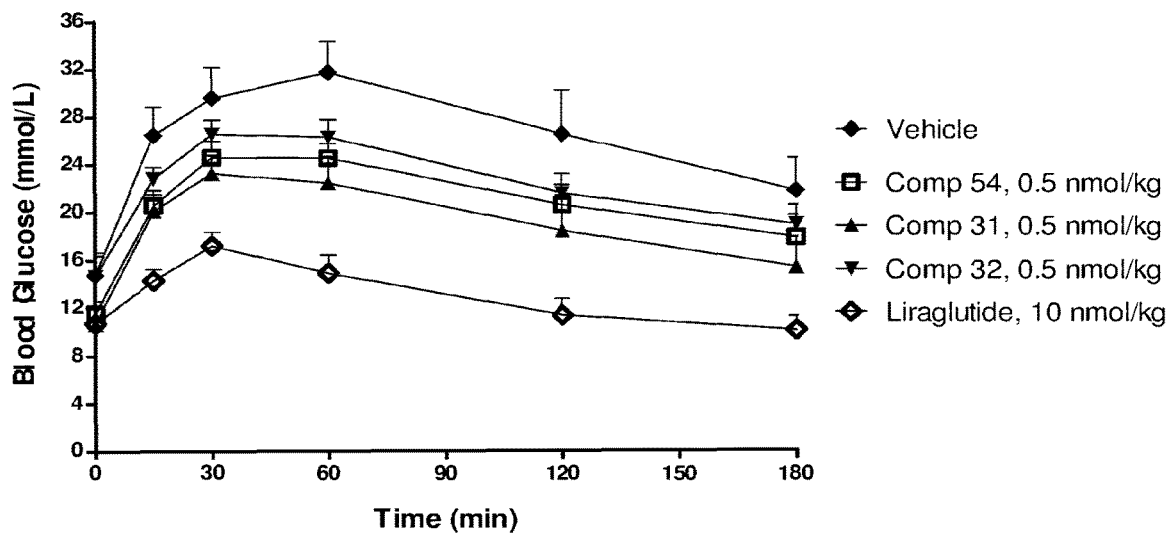
FIGS. 1A-1C: Blood glucose levels (FIG. 1A, FIG. 1B) and area under the blood glucose curves (AUC) (FIG. 1C) in an IPGTT in 5-hour fasted diabetic db/db mice. The mice were injected s.c. with vehicle or GIP-GLP-1 dual acting receptor agonists (0.5 and 5 nmol/kg) 22 hours prior to the i.p. injection of glucose (t=0). The GLP-1 analogue liraglutide (10 nmol/kg) was administered s.c. 4 hours before the i.p. injection of glucose. Data are means±SEM; n=8.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

Definitions

Unless specified otherwise, the following definitions are provided for specific terms, which are used in the above written description.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "solvate" in the context of the present invention refers to a complex of defined stoichiometry formed between a solute (in casu, a peptide conjugate or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that activates the receptor type in question.

The term "GIP-GLP 1 dual receptor agonist" as employed in the context of the invention refers to a substance (ligand) that activates both the GIP receptor and the GLP-1 receptor.

Throughout the description and claims the conventional one-letter and three-letter codes for natural (or "proteinogenic") amino acids are used, as well as generally accepted three letter codes for other (non-natural or "non-proteinogenic") α-amino acids, such as Aib (α-aminoisobutyric acid), Orn (ornithine) and D-Ala (D-alanine). All amino acid residues in peptides of the invention are preferably of the L-configuration except where explicitly stated.

Among sequences disclosed herein are sequences incorporating an "H—" moiety at the amino terminus (N-terminus) of the sequence, and either an "—OH" moiety or an "—NH$_2$" moiety at the carboxy terminus (C-terminus) of the sequence. In such cases, and unless otherwise indicated, an "H—" moiety at the N-terminus of the sequence in question indicates a hydrogen atom (i.e. $R^1$=H), corresponding to the presence of a free primary or secondary amino group at the N-terminus, while an "—OH" or an "—NH$_2$" moiety at the C-terminus of the sequence (i.e. $R^2$=OH or NH$_2$) indicates a carboxy (COOH) group or an amido (CONH$_2$) group at the C-terminus, respectively.

Other $R^1$ groups are possible at the N-terminus, including pyroglutamic acid (pGlu; (S)-(−)-2-pyrrolidone-5-carboxylic acid), $C_{1-4}$ alkyl, acetyl, formyl, benzoyl and trifluoroacetyl.

Receptor Agonist Activity

As mentioned above, the compounds described herein are GIP-GLP 1 dual receptor agonists. That is to say, they have agonist activity at both the GIP receptor and the GLP-1 receptor.

The term "agonist" as employed in the context of the invention refers to a substance (ligand) that is capable of binding to a particular receptor and activating signaling by that receptor. Thus a GIP receptor agonist is capable of binding to the GIP receptor (designated GIP-R) and activating signaling by that receptor, e.g. by generation of cAMP or inducing Ca$^{2+}$ release. Agonist activity at the GIP receptor may therefore be measured by assessing GIP receptor signalling, which may, for example, be measured via cAMP production or Ca$^{2+}$ release.

The cDNA sequence encoding the human GIP receptor has GenBank accession no. BC101673.1 (GI:75516688). The encoded amino acid sequence (including signal peptide) is:

```
  1 MTTSPILQLL LRLSLCGLLL QRAETGSKGQ TAGELYQRWE

RYRRECQETL AAAEPPSGLA

61 CNGSFDMYVC WDYAAPNATA RASCPWYLPW HHHVAAGFVL

RQCGSDGQWG LWRDHTQCEN

121 PEKNEAFLDQ RLILERLQVM YTVGYSLSLA TLLLALLILS

LFRRLHCTRN YIHINLFTSF

181 MLRAAAILSR DRLLPRPGPY LGDQALALWN QALAACRTAQ

IVTQYCVGAN YTWLLVEGVY

241 LHSLLVLVGG SEEGHFRYYL LLGWGAPALF VIPWVIVRYL

YENTQCWERN EVKAIWWIIR

301 TPILMTILIN FLIFIRILGI LLSKLRTRQM RCRDYRLRLA

RSTLTLVPLL GVHEVVFAPV

361 TEEQARGALR FAKLGFEIFL SSFQGFLVSV LYCFINKEVQ

SEIRRGWHHC RLRRSLGEEQ

421 RQLPERAFRA LPSGSGPGEV PTSRGLSSGT LPGPGNEASR

ELESYC
```

(GenBank AA101674.1 GI:75516689). This may be employed in any assays to determine GIP signalling.

Similarly the compounds have agonist activity at the GLP-1 receptor (GLP-1-R), i.e. they are capable of binding to the GLP-1 receptor and activating signaling by that receptor, e.g. by generation of cAMP or inducing Ca$^{2+}$ release. Agonist activity at the GLP-1 receptor may therefore be measured by assessing GLP-1 receptor signalling, which may, for example, be measured via cAMP production or Ca$^{2+}$ release.

The GLP-1 receptor may have the sequence of the human glucagon-like peptide 1 receptor (GLP-1R) having primary accession number P43220. The precursor protein (including signal peptide) has primary accession number NP_002053.3; GI:166795283 and has sequence:

```
  1 MAGAPGPLRL ALLLLGMVGR AGPRPQGATV SLWETVQKWR

EYRRQCQRSL TEDPPPATDL

61 FCNRTFDEYA CWPDGEPGSF VNVSCPWYLP WASSVPQGHV

YRFCTAEGLW LQKDNSSLPW

121 RDLSECEESK RGERSSPEEQ LLFLYIIYTV GYALSFSALV

IASAILLGFR HLHCTRNYIH

181 LNLFASFILR ALSVFIKDAA LKWMYSTAAQ QHQWDGLLSY

QDSLSCRLVF LLMQYCVAAN

241 YYWLLVEGVY LYTLLAFSVL SEQWIFRLYV SIGWGVPLLF

VVPWGIVKYL YEDEGCWTRN

301 SNMNYWLIIR LPILFAIGVN FLIFVRVICI VVSKLKANLM

CKTDIKCRLA KSTLTLIPLL

361 GTHEVIFAFV MDEHARGTLR FIKLFTELSF TSFQGLMVAI

LYCFVNNEVQ LEFRKSWERW

421 RLEHLHIQRD SSMKPLKCPT SSLSSGATAG SSMYTATCQA

SCS.
```

This may be employed in any assays to determine GIP signalling.

The compounds of the present invention have at least one GIP and one GLP-1 biological activity, in particular in treatment of metabolic diseases such as diabetes and obesity. This can be assessed, e.g., in in vivo assays, for example as described in the examples, in which the blood glucose level or another biological activity is determined after a test animal has been treated or exposed to a GIP analogue. In particular, compounds of the invention may be capable of improving glycaemic control when adminstered to a diabetic subject. Additionally or alternatively, they may be capable of reducing body weight when administered to an overweight or obese subject. In either case, the effect may be superior to that obtained with an equivalent quantity (by mass, or molar ratio) of wild type human GIP or GLP-1 in comparable subjects when given according to a comparable dosing regime.

Activity in in vitro assays may also be used as a measure of the compounds' activity. Typically the compounds have activity at both the GLP-1 and GIP receptors (designated GLP-1-R and GIP-R respectively). $EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$ [GLP-1R] lower than the $EC_{50}$ [GLP-1R] of native GIP in a particular assay may be considered to have higher potency at the GLP-1R than GIP. In some embodiments of the present invention, the $EC_{50}$ GLP-1-R and/or $EC_{50}$ GIP-R is below 1.0 nM, below 0.9 nM, below 0.8 nM, below 0.7 nM, below 0.6 nM, below 0.5 nM, below 0.4 nM, below 0.3 nM, below 0.2 nM, below 0.1 nM, below 0.09 nM, below 0.08 nM, below 0.07 nM, below 0.06 nM, below 0.05 nM, below 0.04 nM, below 0.03 nM, below 0.02 nM, below 0.01 nM, below 0.009 nM, below 0.008 nM, below 0.007 nM, below 0.006 nM, below 0.005 nM, or below 0.004 nM, e.g. when assessed using the assay described in Example 2. In any given assay, the $EC_{50}$ value of a compound in a given assay may be assessed relative to the $EC_{50}$ of human GIP. Thus, the ratio of the $EC_{50}$ value of the test compound to the $EC_{50}$ value of wild type human GIP ($EC_{50}$[test compound]/$EC_{50}$[GIP]) at the human GIP receptor may be less than 10, less than 5, less than 1, less than 0.1, less than 0.05 or less than 0.01. The ratio of the $EC_{50}$ value of the test compound to the $EC_{50}$ value of wild type human GIP ($EC_{50}$[test compound]/$EC_{50}$[GIP]) at the GLP-1 receptor may be less than 10, less than 5, less than 1, less than 0.1, less than 0.05 or less than 0.01. It may also be desirable to compare the ratio of $EC_{50}$ values at the two receptors for the test compound and for human GIP. Preferably the test compound has an $EC_{50}$[GIP]/$EC_{50}$[GLP-1] which is greater than the equivalent ratio for GIP in the same assays.

Lipophilic Group

In all aspects, the compound of the invention comprises a residue ψ, i.e. a residue selected from Lys, Arg, Orn and Cys in which the side chain is conjugated to a substituent —$Z^2$—$Z^1$— as described in more detail below.

Without wishing to be bound by any particular theory, it is thought that the substituent binds plasma proteins (e.g. albumin) in the blood stream, thus shielding the compounds of the invention from enzymatic degradation and renal clearance and thereby enhancing the half-life of the compounds. It may also modulate the potency of the compound, e.g. with respect to the GIP receptor and/or the GLP-1 receptor.

The substituent is conjugated to the functional group at the distal end of the side chain from the alpha-carbon. The normal ability of the Lys, Arg, Orn or Cys side chain to participate in interactions mediated by that functional group (e.g. intra- and inter-molecular interactions) may therefore be reduced or completely eliminated by the presence of the substituent. Thus, the overall properties of the compound may be relatively insensitive to changes in the actual amino acid present as residue ψ. Consequently, it is believed that any of the residues Lys, Arg, Orn and Cys may be present at any position where ψ is permitted. However, in certain embodiments, it may be advantageous that the amino acid component of ψ is Lys.

ψ is a residue of Lys, Arg, Orn or Cys in which the side chain is conjugated to a substituent having the formula —$Z^1$ or —$Z^2$—$Z^1$;

—$Z^1$ is a fatty chain having a polar group at one end of the chain and a connection to ψ or $Z^2$, —X—, at the end of the chain distal from the polar group, wherein the polar group comprises a carboxylic acid or a carboxylic acid bioisostere, a phosphonic acid, or a sulfonic acid group;

and —X— is a bond, —CO—, —SO—, or —$SO_2$—;

—$Z^2$—, if present, is a spacer of formula:

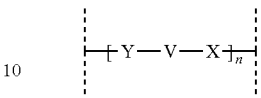

connecting $Z^1$ to ψ;

wherein:

each Y is independently —NH, —NR, —S or —O, where R is alkyl, a protecting group or forms a linkage to another part of the spacer $Z^2$;

each X is independently a bond, CO—, SO—, or $SO_2$—; with the proviso that when Y is —S, the X to which it is bound is a bond;

each V is independently a bivalent organic moiety linking Y and X;

and n is 1-10;

The Group $Z^1$ $Z^1$ is a fatty chain having a connection to ψ or to $Z^2$, referred to herein as —X— and, at the end of the chain distal from the connection to $Z^2$, a polar group. —X— may be, for example, a bond, acyl (—CO—), sulfinyl (—SO—), or sulfonyl (—$SO_2$—), the connection being located at the ω-position with respect to the polar group, that is, at the end of the chain distal from the polar group. When $Z^1$ is bound directly to ψ, that is, when $Z^2$ is not present, preferably —X— is acyl (—CO—), sulfinyl (—SO—), or sulfonyl (—$SO_2$—). Most preferably, —X— is acyl (—CO—).

Preferably, the polar group is an acidic or weakly acid group, for example a carboxylic acid or a carboxylic acid bioisostere, a phosphonate, or a sulfonate. The polar group may have a $pK_a$ of between −2 and 12 in water, more preferably between 1 and 7, more preferably between 3 and 6. Certain preferred polar groups have a $pK_a$ of between 4 and 5.

The polar group preferably comprises a carboxylic acid or carboxylic acid bioisostere. Suitable carboxylic acid bioisosteres are known in the art. Preferably the bioisostere has a proton having a $pK_a$ similar to the corresponding carboxylic acid. Examples of suitable bioisoteres may include, not by way of limitation, tetrazole, acylsulfomides, acylhydroxylamine, and squaric acid derivatives, as shown below (--- indicates the point of attachment):

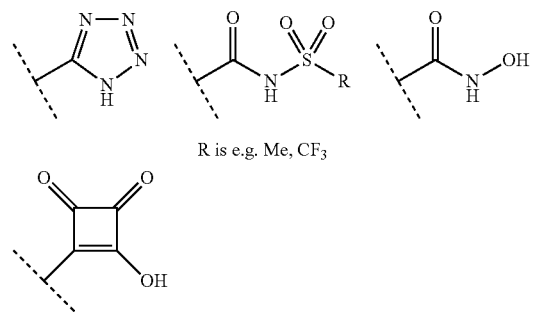

The polar group may be a group of formula A-B—, wherein A is a carboxylic acid (—COOH) or a carboxylic acid bioisostere, a phosphonic acid (—P(O)(OH)$_2$), or a sulfonic acid (—SO$_2$OH) group, and B is a bond or linker between A and the fatty chain. In some embodiments, the polar group is —COOH, that is, A is —COOH and B is a bond.

When B is a linker, it may be a cycloalkylene, heterocycloalkylene, C$_6$arylene, or C$_{5-6}$heteroarylene, or C$_6$arylene-O— or C$_{5-6}$heteroarylene-O—.

When B is phenylene it may, for example, be selected from 1,2-phenylene, 1,3-phenylene, 1,4-phenylene, preferably 1,4-phenylene (so that A-B— is a 4-benzoic acid substituent or 4-benzoic acid bioisostere). When B is phenylene-O—, it may, for example, be selected from 1,2-phenylene-O—, 1,3-phenylene-O—, 1,4-phenylene-O—, preferably 1,4-phenylene-O. Each phenylene of B may be optionally substituted with one or more substituents selected from fluoro, methyl, trifluoromethyl, amino, hydroxyl, and C$_{1-4}$alkoxy, preferably methoxy. It will be appreciated that substituent identity and position may be selected to subtly alter the pK$_a$ of the polar group. Suitable inductively or mesomerically electron-withdrawing or donating groups and their positional effects are known in the art. In some embodiments, B may be C$_{5-6}$heteroarylene, for example, pyridinylene or thiofuranylene, and may be optionally substituted as described.

For example, in some embodiments, A-B— may be selected from:

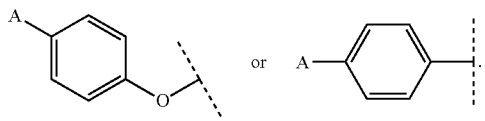

Preferably, A is —COOH. In some preferred polar groups, A is a carboxylic acid and B is C$_6$arylene-O—.

Fatty chain as used herein refers to a moiety comprising a chain of carbon atoms, the carbon atoms being predominantly substituted with hydrogen or hydrogen-like atoms, for example, a hydrocarbon chain. Such fatty chains are often referred to as lipophilic, although it will be appreciated that substitution may alter the lipophilic properties of the overall molecule.

The fatty chain may by aliphatic. It may be entirely saturated or may include one or more double or triple bonds. Each double bond, if present, may be in the E or Z configuration. The fatty chain may also have one or more cycloalkylene or heterocycloalkylene moieties in its length, and additionally or alternatively may have one or more arylene or heteroarylene moieties in its length. For example, the fatty chain may incorporate a phenylene or piperazinylene moiety in its length as, for example, shown below (wherein --- represents the points of attachment within the chain).

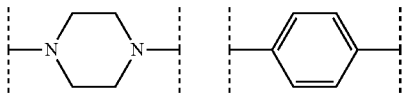

The fatty chain may be derived from a fatty acid, for example, it may be derived from a medium-chain fatty acid (MCFA) with an aliphatic tail of 6-12 carbon atoms, a long-chain fatty acid (LCFA) with an aliphatic tail of 13-21 carbon atoms, or a very long-chain fatty acid (LCFA) with an aliphatic tail of 22 carbon atoms or more. Examples of linear saturated fatty acids from which suitable fatty chains may be derived include tridecylic (tridecanoic) acid, myristic (tetradecanoic) acid, pentadecylic (pentadecanoic) acid, palmitic (hexadecanoic) acid, margaric (heptadecanoic) acid, and arachidic (eicosanoic) acid. Examples of linear unsaturated fatty acids from which suitable fatty chains may be derived include myristoleic acid, palmitoleic acid, sapienic acid and oleic acid.

The fatty chain may be connected to ψ or to Z$^2$ by an amide linkage, a sulfinamide linkage, a sulfonamide linkage, or by an ester linkage, or by an ether, thioether or amine linkage. Accordingly, the fatty chain may have at the w position, that is, the position distal to the polar group, a bond to Z$^2$ or an acyl (—CO—), sulfinyl (—SO—), or sulfonyl (—SO$_2$—) group. Preferably, the fatty chain has an acyl (—CO—) group at the position distal to the polar group and is connected to Z$^2$ by an amide or ester linkage.

In some embodiments, Z$^1$ is a group of formula:

where A-B— is the polar group defined above, X is a bond, acyl (—CO—), sulfinyl (—SO—), or sulfonyl (—SO$_2$—), and Alk is a fatty chain that may be optionally substituted with one or more substituents. The fatty chain is preferably 16 to 28 carbon atoms in length (e.g. a C$_{16-28}$alkylene), more preferably, 16 to 26 carbons in length (e.g. a C$_{16-26}$alkylene), more preferably, 16 to 22 carbons in length (e.g. C$_{16}$-alkylene), and may be saturated or unsaturated. Preferably, Alk is saturated, that is, preferably Alk is alkylene.

In some embodiments, Z$^1$ is an acyl group of formula:

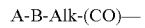

or a sulfonyl group of formula:

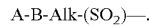

Optional substituents on the fatty chain may be independently selected from fluoro, C$_{1-4}$alkyl, preferably methyl; trifluoromethyl, hydroxymethyl, amino, hydroxyl, C$_{1-4}$alkoxy, preferably methoxy; oxo, and carboxyl, and may be independently located at any point along the chain. In some embodiments, each optional substituent is selected from fluoro, methyl, and hydroxyl. Where more than one substituent is present, substituents may be the same or different. Preferably, the number of substituents is 0 to 3; more preferably the fatty chain is unsubstituted.

Preferably, Z$^1$ is an acyl group of formula:

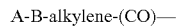

where A and B are as defined above.

In some embodiments, Z$^1$ is:
4-carboxyphenoxynonanoyl HOOC—C$_6$H$_4$—O—(CH$_2$)$_8$—(CO)—.

Certain preferred Z$^1$ are derived from long-chain saturated α,ω-dicarboxylic acids of formula HOOC—(CH$_2$)$_{12-22}$—COOH, preferably, long-chain saturated α,ω-dicarboxylic acids having an even number of carbon atoms in the aliphatic chain. For example, and not by way of limitation, Z$^1$ may be:
17-carboxyheptadecanoyl HOOC—(CH$_2$)$_{16}$—(CO)—;
19-carboxynonadecanoyl HOOC—(CH$_2$)$_{18}$—(CO)—; or
21-carboxyhenicosanoyl HOOC—(CH$_2$)$_{20}$—(CO)—.

The carboxylic acid group may be replaced by a bioisotere as detailed herein.

The Group Z$^2$

Z$^2$ is an optional spacer that connects Z$^1$ to the side chain of the amino acid component of ψ. At its most general, Z$^2$, if present, is a spacer bound at one terminus by Y, which may be a nitrogen, oxygen or sulfur atom, and at the other terminus by X, which may be a bond or an acyl (—CO—), sulfinyl (—SO—), sulfonyl (—SO$_2$—) or absent. Accordingly, $Z^2$ may be a spacer of formula (--- indicate points of attachment):

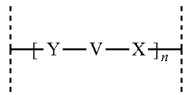

wherein:
Y may be —NH, —NR, —S or —O, where R may be alkyl, a protecting group or may form a linkage to another part of the spacer, with the remaining valency forming a linkage to Z;
X may be a bond, CO—, SO—, or SO$_2$—, with the remaining valency forming a linkage to the side chain of the amino acid component of ψ;
V is a bivalent organic moiety linking Y and X;
and n may be 1, 2, 3, 4, 5, 6, 7, 8, 9 or 10. Where n is 2 or more, each Y, V, and X is independent of every other Y, V, and X.

Accordingly, $Z^2$ may be bound at each side by amide, sulfinamide, sulfonamide, or ester linkages or by amino, ether, or thioether linkages depending upon the nature of Y and X and the corresponding linking groups on $Z^1$ and the side chain. Where n is 2 or greater, each V may also be bound to each adjacent V by linkages as described. Preferably, linkages are amides, esters or sulfonamides, most preferably amides. Accordingly, in some embodiments, each Y is —NH or —NR and each X is CO— or SO$_2$—.

In some embodiments, $Z^2$ is a spacer of formula —$S_A$—, —$S_B$—, —$S_A$—$S_B$— or —$S_B$—$S_A$—, wherein $S_A$ and $S_B$ are as defined below.

In some embodiments, $Z^2$ is selected from —$S_A$—, —$S_B$—, or —$S_B$—$S_A$—, that is, [side chain]-$Z^2Z^1$ is [side chain]-$S_A$—$Z^1$, [side chain]-$S_B$—$Z^1$ or [side chain]-$S_B$-$S_A$—$Z^1$.

The Group $S_A$ $S_A$ may be a single amino acid residue or a residue of an amino acid derivative, especially an amino acid derivative residue having a sulfinyl or sulfonyl in place of the carboxy moiety at the C terminus. Additionally or alternatively, the single amino acid residue may have an oxygen or sulfur atom in place of the nitrogen atom at the N terminus.

$S_A$ may comprise a nitrogen-containing heterocycle, said nitrogen-containing heterocycle being bound within the lipophilic group at one end via a bond, a carboxy, a sulfinyl, or a sulfonyl group, and at the other via a ring nitrogen atom. For example, $S_A$ may comprise a piperazine ring.

Suitably, $S_A$ is a 5-8-membered heterocycle having 1 or 2 nitrogen atoms and substituted with an —X or an -L-X group, where X is a bond, CO—, SO—, or SO$_2$—, and where L, if present, is C$_{1-4}$alkylene (- denotes a point of attachment within the lipophilic group).

Preferably, $S_A$ is a 6-membered heterocycle having 1 or 2 nitrogen atoms, preferably 2, and substituted with a —CH$_2$CO—, —CH$_2$SO—, or —CH$_2$SO$_2$— group. For example, $S_A$ may be:

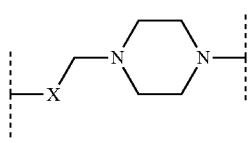

For example, $S_A$ may be:

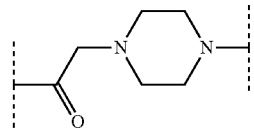

(referred to herein a piperazine-1-yl-acetyl).

Preferably, $S_A$ is a single amino acid residue or piperazine-1-yl-acetyl. More preferably $S_A$ is a single amino acid residue In some embodiments, the amino acid may be selected from γ-Glu, α-Glu, α-Asp, β-Asp, Ala, Dapa (2,3-diaminopropionic acid), or Dab (2,4-diaminobutanoic). It will be understood that where more than one carboxylic acid or amino moiety is present, connection may be at any moiety as appropriate. Any carboxylic acid or amino resides not bound within the residue may be free, that is, present as a free carboxylic acid or primary amine, or may be derivatised. Suitable derivatisation is known in the art. For example, carboxylic acid moieties may be present in $S_A$ amino acid residues as esters, for example, as methyl esters. Amino moieties may be present as alkylated amines, for example, methylated, or may be protected as amide or carbamate moieties. Other suitable amino acids include β-Ala (3-aminopropanoic acid) and Gaba (4-aminobutanoic acid) and similar w amino acids.

It will be understood that amino acids may be D or L, or a racemic or enantioenriched mixture. In some embodiments, the amino acid is an L-amino acid. In some embodiments, the amino acid is a D-amino acid.

In some preferred embodiments, $S_A$ has a carboxylic acid substituent, with γ-Glu, α-Glu, α-Asp, and β-Asp, and sulfinyl and sulfonyl derivatives thereof, being preferred. Accordingly, in some embodiments, the amino acid residue is:

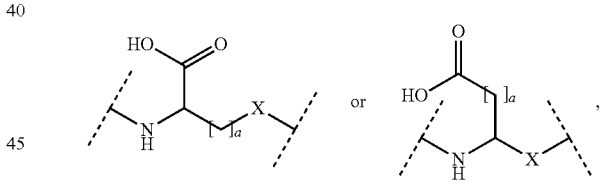

where —X— is —CO—, —SO—, —SO$_2$—, preferably —CO—, and a is 1 or 2, preferably 2. In some embodiments, the carboxylic acid is an ester, and the amino acid residue is:

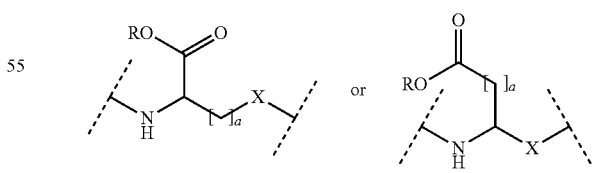

where —X— is —CO—, —SO—, —SO$_2$—, preferably —CO—, and a is 1 or 2, preferably 2, and R is C$_{1-4}$alkyl or C$_6$aryl. Preferably R is C$_{1-4}$alkyl, preferably methyl or ethyl, more preferably ethyl.

A preferred $S_A$ group bearing a carboxylic acid is γ-Glu. Preferably, $S_A$ is selected from Dapa or γ-Glu. Most preferably, $S_A$ is γ-Glu.

The group $S_B$ $S_B$ may be a linker of general formula:

wherein $P_U$ is a polymeric unit and n is 1, 2, 3, 4, 5, 6, 7, 8, 9 or 10. One terminus of the linker $S_B$ is an —NH, —NR, —S or —O, wherein R may be alkyl, a protecting group or may form a linkage to another part of the polymeric unit; while the other is a bond or CO—, SO— or SO$_2$—. Accordingly, each polymeric unit $P_U$ may be bound at each side by amide, sulfinamide, sulfonamide, or ester linkages or by amino, ether, or thioether linkages depending upon the nature of Y and X and the corresponding linking groups on $Z^1$, $S_A$, and Lys.

In some embodiments, each $P_U$ may be independently a unit of formula:

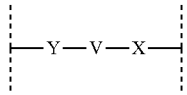

wherein:
Y may be —NH, —NR, —S or —O, wherein R may be alkyl, a protecting group or may form a linkage to another part of the spacer, with the remaining valency forming a linkage to Z;
X may be a bond, CO—, SO—, or SO$_2$—, with the remaining valency forming a linkage to Lys;
and V is a bivalent organic moiety linking Y and X.

In some embodiments, V is the α-carbon of a natural or unnatural amino acid, that is V is —CHR$^{AA}$—, wherein R$^A$ is an amino acid side chain; or V is an optionally substituted C$_{1-6}$alkylene, or V is a chain comprising one or more units of ethylene glycol in series, also known as PEG chain, for example, —CH$_2$CH$_2$—(OCH$_2$CH$_2$)$_m$—O—(CH$_2$)$_p$—, where m is 0, 1, 2, 3, 4, or 5, and p is 1, 2, 3, 4, or 5; when X is CO—, p is preferably 1, 3, 4, or 5. Optional alkylene substituents include fluoro, methyl, hydroxy, hydroxymethy, and amino.

Preferred $P_U$ units include:
(i). Single amino acid residues: $P_U^i$;
(ii). Dipeptide residues: $P_U^{ii}$; and
(iii). Amino-(PEG)$_m$-carboxylic acid residues: $P_U^{iii}$,
and may be present in any combination or order. For example, $S_B$ may comprise one or more of each of $P_U^i$, $P_U^{ii}$, and $P_U^{iii}$ in any order, or may comprise one or more units of $P_U^i$, $P_U^{ii}$, and $P_U^{iii}$ only, or one of more units selected from $P_U^i$ and $P_U^{ii}$, $P_U^i$ and $P_U^{iii}$, or $P_U^{ii}$ and $P_U^{iii}$.

(i). $P_U^i$ Single Amino Acid Residues

Each $P_U^i$ may be independently selected from any natural or unnatural amino acid residue and, for example, may be selected from Gly, Pro, Ala, Val, Leu, Ile, Met, Cys, Phe, Tyr, Trp, His, Lys, Arg, Gin, Asn, α-Glu, γ-Glu, Asp, Ser Thr, Dapa, Gaba, Aib, β-Ala, 5-aminopentanoyl, 6-aminohexanoyl, 7-aminoheptanoyl, 8-aminooctanoyl, 9-aminononanoyl, and 10-aminodecanoyl. Preferably, $P_U^i$ amino acid residues are selected from Gly, Ser, Ala, Thr, and Cys, more preferably from Gly and Ser.

In some embodiments, $S_B$ is —(P$_U^i$)$_n$—, wherein n is 1 to 8, more preferably 5 to 7, most preferably 6. In some preferred embodiments, $S_B$ is —(P$_U^i$)$_n$—, n is 6 and each P$_U^i$ is independently selected from Gly or Ser, with a preferred sequence being -Gly-Ser-Gly-Ser-Gly-Gly-.

(ii). $P_U^{ii}$ Dipeptide Residues

Each $P_U^{ii}$ may be independently selected from any dipeptide residue comprising two natural or unnatural amino acid residues bound by an amide linkage. Preferred $P_U^{ii}$ dipeptide residues include Gly-Gly, Gly-Ser, Ser-Gly, Gly-Ala, Ala-Gly, and Ala-Ala, more preferably Gly-Ser and Gly-Gly.

In some embodiments, $S_B$ is —(P$_U^{ii}$)$_n$—, wherein n is 2 to 4, more preferably 3, and each P$_U^{ii}$ is independently selected from Gly-Ser and Gly-Gly. In some preferred embodiments $S_B$ is —(P$_U$)$_n$—, n is 3 and each Pull is independently selected from Gly-Ser and Gly-Gly, with a preferred sequence being -(Gly-Ser)-(Gly-Ser)-(Gly-Gly).

Amino acids having stereogenic centres within $P_U^i$ and $P_U^{ii}$ may be racemic, enantioenriched, or enantiopure. In some embodiments, the or each amino acid is independently an L-amino acid. In some embodiments, the or each amino acid is independently a D-amino acid.

(iii). $P_U^{iii}$ Amino-(PEG)$_m$-Carboxylic Acid Residues

Each $P_U^{iii}$ may be independently a residue of general formula:

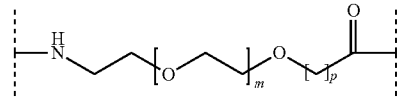

wherein m is 0, 1, 2, 3, 4, or 5, preferably 1, 2, 3, or 4, more preferably 1 or 2, and p is 1, 2, 3, 4 or 5, e.g. 1, 3, 4, or 5, preferably 1.

In some embodiments, m is 1 and p is 1, that is, $P_U^{iii}$ is a residue of 8-amino-3,6-dioxaoctanoic acid (also known as {2-[2-aminoethoxy]ethoxy}acetic acid and H$_2$N-PEG$_3$-COOH). This residue is referred to herein as -PEG$_3$-.

In some embodiments, m is 5 and p is 2, that is, $P_U^{iii}$ is a residue of 2-[2-[2-[2-[2-[2-(2-aminoethoxy)ethoxy]ethoxy]ethoxy]ethoxy]propanoic acid (also known as H$_2$N-PEG$_6$-COOH). This residue is referred to herein as -PEG$_6$-.

In some embodiments, m is 2 and p is 1, that is, $P_U^{iii}$ is a residue of 11-amino-3,6,9-trioxaundecanoic acid (also known as H$_2$N-PEG$_4$-COOH). This residue is referred to herein as -PEG$_4$-

In some embodiments, $S_B$ is —(P$_U^{ii}$)$_n$—, wherein n is 1 to 3, more preferably 2.

In some preferred embodiments, $S_B$ is selected from -PEG$_3$-PEG$_3$- and -PEG$_3$-PEG$_3$-PEG$_3$-.

Most preferably, $S_B$ is -PEG$_3$-PEG$_3$-.

Preferred —Z$^2$—Z$^1$

It will be understood that the above preferences may be independently combined to give preferred —Z$^1$ and —Z$^2$—Z$^1$ combinations.

Some preferred —Z$^2$—Z$^1$ combinations are shown below (in each case, --- indicates the point of attachment to the side chain of the amino acid component of ψ:

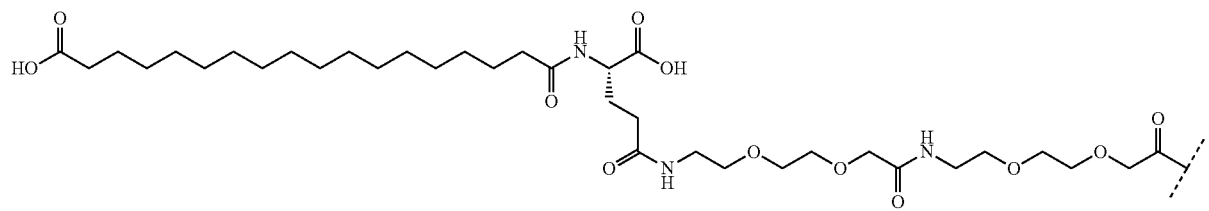
[17-Carboxy-heptadecanoyl]-isoGlu-Peg3-Peg3
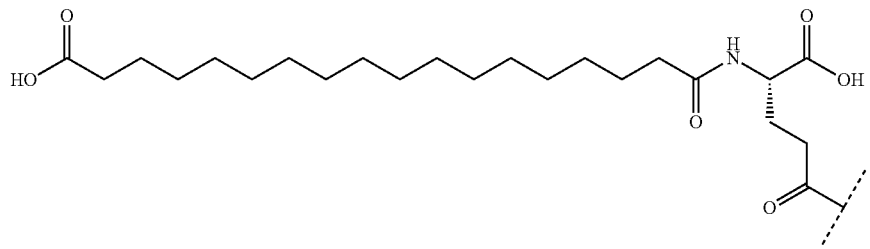
[17-Carboxy-heptadecanoyl]-isoGlu
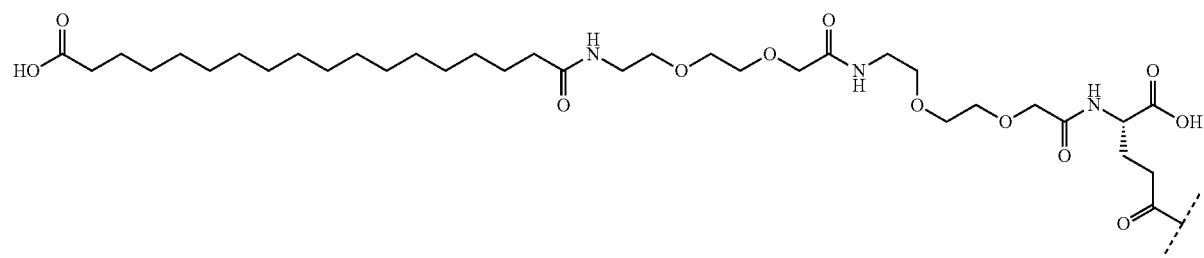
[17-Carboxy-heptadecanoyl]-Peg3-Peg3-isoGlu
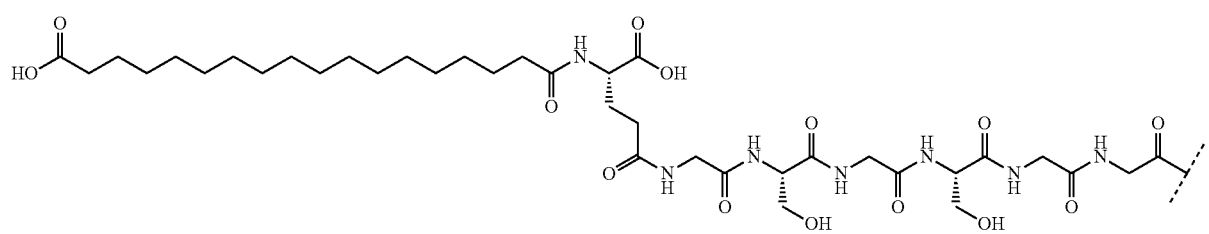
[17-Carboxy-heptadecanoyl]-isoGlu-GSGSGG
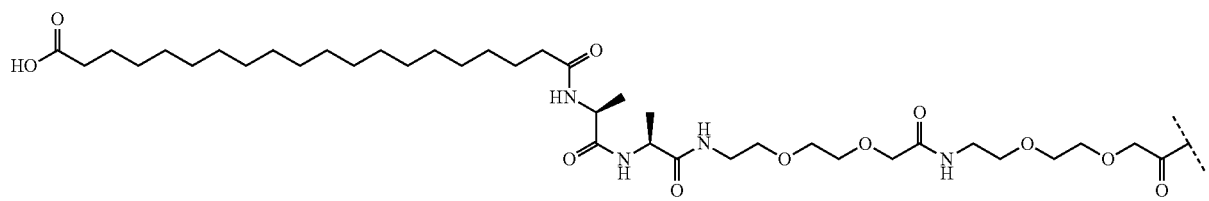
[17-Carboxy-heptadecanoyl]-AA-Peg3-Peg3

(vi)
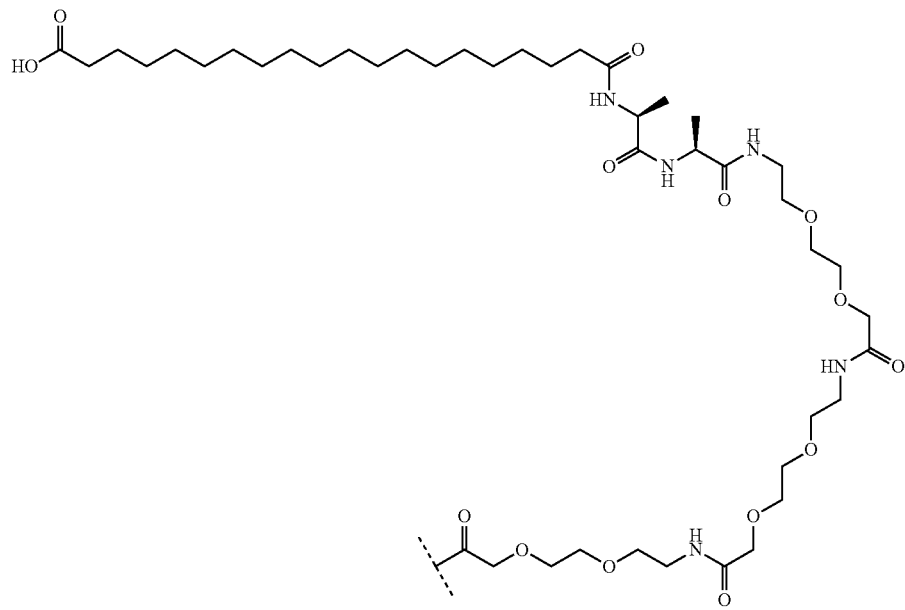
([19-Carboxy-nonadecanoyl]-AA-Peg3-Peg3-Peg3)
(vii)
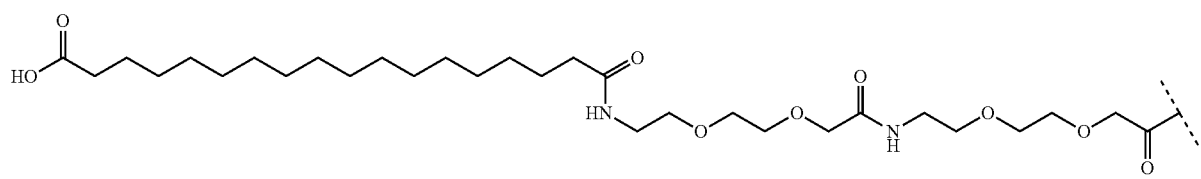
[17-Carboxy-heptadecanoyl]-Peg3-Peg3
(viii)
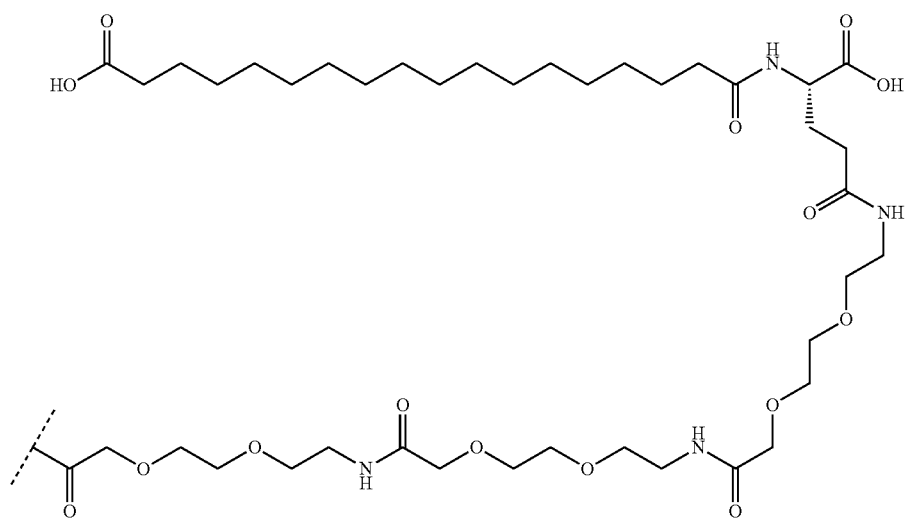
[17-Carboxy-heptadecanoyl]-isoGlu-Peg3-Peg3-Peg3

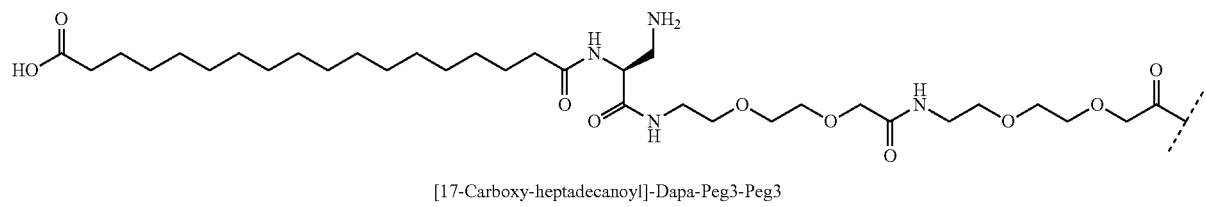
[17-Carboxy-heptadecanoyl]-Dapa-Peg3-Peg3
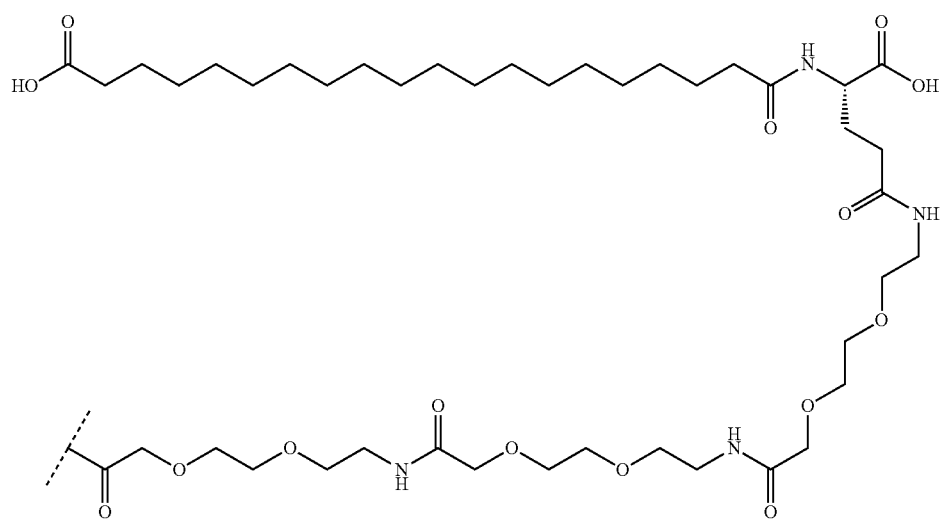
[19-Carboxy-heptadecanoyl]-isoGlu-Peg3-Peg3-Peg3
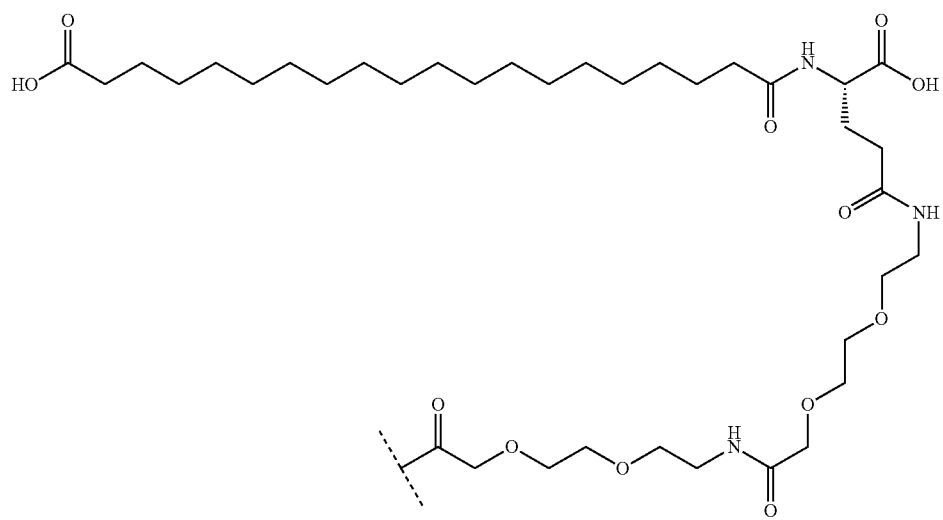
[19-Carboxy-nonadecanoyl]-isoGlu-Peg3-Peg3

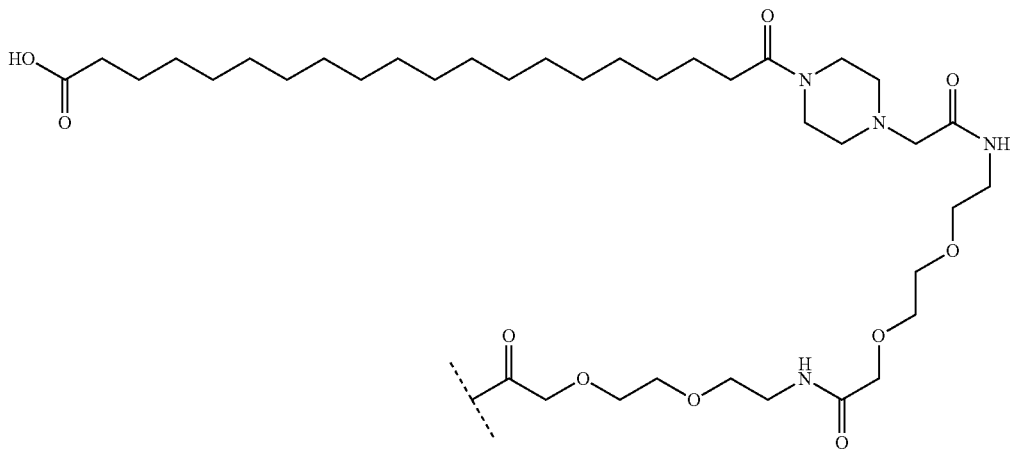

(19-Carboxy-nonadecanoyl)-[(Piperazine-1-yl)-acetyl]-Peg3-Peg3

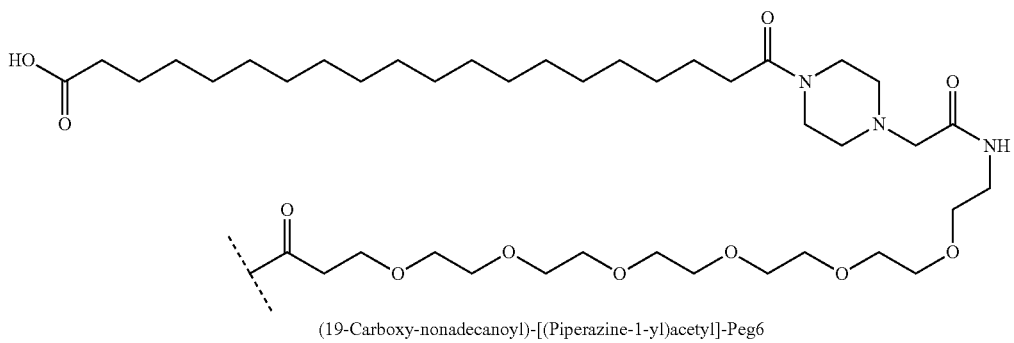

(19-Carboxy-nonadecanoyl)-[(Piperazine-1-yl)acetyl]-Peg6

The skilled person will be well aware of suitable techniques for preparing the compounds employed in the context of the invention. For examples of suitable chemistry, see, e.g., WO98/08871, WO00/55184, WO00/55119, Madsen et al. (J. Med. Chem. 2007, 50, 6126-32), and Knudsen et al. 2000 (J. Med Chem. 43, 1664-1669).

Clinical Utility

The GIP analogue compounds employed in the context of the invention may provide an attractive treatment option for metabolic diseases including obesity, diabetes mellitus (diabetes), obesity-related disorders, and diabetes-related disorders. Diabetes comprises a group of metabolic diseases characterized by hyperglycemia resulting from defects in insulin secretion, insulin action, or both. Diabetes is classified into type 1 diabetes, type 2 diabetes and gestational diabetes on the basis on pathogenic characteristics. Type 1 diabetes accounts for 5-10% of all diabetes cases and is caused by auto-immune destruction of insulin-secreting pancreatic β-cells. Acute signs of diabetes include excessive urine production, resulting compensatory thirst and increased fluid intake, blurred vision, unexplained weight loss, lethargy, and changes in energy metabolism. However, in type 2 diabetes symptoms are often not severe or may be absent. The chronic hyperglycemia of diabetes is associated with long-term damage, dysfunction, and failure of various organs, notably the eyes, kidneys, nerves, heart and blood vessels.

Type 2 diabetes accounts for 90-95% of diabetes cases and is a result of a complex set of metabolic disorders. However, symptoms are often not severe or may be absent.

Type 2 diabetes is the consequence of endogenous insulin production becoming insufficient to maintain plasma glucose levels below diagnostic thresholds.

Gestational diabetes refers to any degree of glucose intolerance identified during pregnancy.

Pre-diabetes includes impaired fasting glucose and impaired glucose tolerance and refers to those states that occur when blood glucose levels are elevated but below the levels that are established for the clinical diagnosis for diabetes.

A large proportion of people with type 2 diabetes and pre-diabetes are at increased risk of morbidity and mortality due to the high prevalence of additional metabolic risk factors, including abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension) a prothrombotic state (e.g. high fibrinogen or plasminogen activator inhibitor-1 in the blood), and/or a proinflammatory state (e.g., elevated C-reactive protein in the blood).

Conversely, obesity confers an increased risk of developing pre-diabetes, type 2 diabetes as well as, e.g., certain types of cancer, obstructive sleep apnea and gall-bladder disease. Dyslipidemia is associated with increased risk of cardiovascular disease. High Density Lipoprotein (HDL) is of clinical importance since an inverse correlation exists between plasma HDL concentrations and risk of atherosclerotic disease. The majority of cholesterol stored in atherosclerotic plaques originates from LDL and hence an elevated concentration of Low Density Lipoproteins (LDL) is closely associated with atherosclerosis. The HDL/LDL ratio is a clinical risk indictor for atherosclerosis and coronary atherosclerosis in particular.

Compounds employed in the context of the invention act as GIP-GLP1 dual agonists. The dual agonist may combine the effect of GIP, e.g., on fat metabolism and weight loss, and blood glucose, with the effect of GLP-1, e.g., on blood glucose levels and food intake. They may therefore act to accelerate elimination of excessive adipose tissue, induce sustainable weight loss, and improve glycemic control. Dual GIP-GLP1 agonists may also act to reduce cardiovascular risk factors such as high cholesterol, such as high LDL-cholesterol.

The GIP-GLP1 dual agonist compounds of the present invention may therefore be used (alone or in combination) as pharmaceutical agents for preventing weight gain, promoting weight loss, reducing excess body weight or treating obesity (e.g., by control of appetite, feeding, food intake, calorie intake, and/or energy expenditure and lipolysis), including morbid obesity, as well as associated diseases and health conditions including but not limited to obesity linked inflammation, obesity linked gallbladder disease and obesity induced sleep apnea. The GIP-GLP1 dual agonist compounds employed in the context of the invention may also be used for treatment of insulin resistance, glucose intolerance, pre-diabetes, increased fasting glucose, type 2 diabetes, hypertension, dyslipidemia (or a combination of these metabolic risk factors), atherosclerosis, arteriosclerosis, coronary heart disease, peripheral artery disease and stroke. These are all conditions which may be associated with obesity. However, the effects of the compounds employed in the context of the invention on these conditions may be mediated in whole or in part via an effect on body weight, or may be independent thereof.

The GIP-GLP1 dual agonist compounds may thus be used (alone or in combination) for the treatment and/or prevention of any of the diseases, disorders, or conditions described herein, including insulin resistance, glucose intolerance, increased fasting glucose, pre-diabetes, type 1 diabetes, type 2 diabetes, gestational diabetes hypertension, dyslipidemia, or a combination thereof. In certain embodiments, the diabetes related disorder is selected from atherosclerosis, arteriosclerosis, coronary heart disease, peripheral artery disease and stroke; or associated with a condition selected from atherogenic dyslipidemia, blood fat disorders, elevated blood pressure, hypertension, a prothrombotic state, and proinflammatory state, or a combination thereof. In certain embodiments, the blood fat disorder is selected from high triglycerides, low HDL cholesterol, high LDL cholesterol, plaque buildup in artery walls, or a combination thereof. In certain embodiments, the prothrombotic state is selected from high fibrinogen levels in the blood and high plasminogen activator inhibitor-1 levels in the blood. In certain embodiments, the proinflammatory state is an elevated C-reactive protein level in the blood. In certain embodiments, the obesity related disorder is selected from obesity linked inflammation, obesity linked gallbladder disease and obesity induced sleep apnea.

The GIP-GLP1 dual agonist compounds may also be used for the treatment and/or prevention of any of the diseases, disorders, or conditions associated with diabetes related osteoporosis including increased risk of bone fractures. The observed increase in fracture risk is likely to be related to impaired bone quality rather than to bone mineral density. The related mechanisms, due at least in part to hyperglycemia, neuropathy, and higher incidence of hypovitaminosis D, are not yet fully understood.

The invention provides the use of a GIP-GLP1 dual agonist compound as described, in the manufacture of a medicament for any of the clinical applications described in this specification. Reference to a compound for use in any such method should be construed accordingly.

In some embodiments, the invention also provides a therapeutic kit comprising a GIP analogue of the invention, optionally in combination with a pharmaceutically acceptable carrier. In some embodiments, the invention provides a device comprising a GIP analogue of the invention for delivery of the GIP analogue to a subject.

Pharmaceutical Compositions

The GIP-GLP1 dual agonist compounds of the present invention, or salts or solvates thereof, may be formulated as pharmaceutical compositions prepared for storage or administration, which typically comprise a therapeutically effective amount of a compound employed in the context of the invention, or a salt or solvate thereof, in a pharmaceutically acceptable carrier. In some embodiments, the pharmaceutical composition is formulated as a liquid suitable for administration by injection or infusion, or which is formulated to cause slow release of the GIP-GLP1 dual agonist compound.

The therapeutically effective amount of a compound of the present invention will depend, e.g., on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Suitable pH buffering agents may be, e.g., phosphate, citrate, acetate, lactate, maleate, tris/hydroxymethyl)aminomethane (TRIS), N-Tris(hydroxymethyl)methyl-3-aminopropanesulphonic acid (TAPS), ammonium bicarbonate, diethanolamine, histidine, which in certain embodiments is a preferred buffer, arginine, lysine, or acetate or mixtures thereof. The term further encompasses any agents listed in the US Pharmacopeia for use in animals, including humans.

The term "pharmaceutically acceptable salt" refers to a salt of the compound. Salts include pharmaceutically acceptable salts, such as, e.g., acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" may also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms (e.g. weight gain, hyperglycemia) when compared to the absence of treatment, and is not necessarily meant to imply complete cessation of the relevant condition.

The pharmaceutical compositions of the invention may be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of an injection pen. Compositions may be formulated for any suitable route and means of administration. Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for certain of the compounds described herein.

Combination Therapy

In certain embodiments, a GIP-GLP-1 dual agonist compound employed in the context of the invention may be administered as part of a combination therapy with at least one other agent for treatment of diabetes, obesity, dyslipidemia, or hypertension.

In such cases, the at least two active agents may be given together or separately, and as part of the same pharmaceutical formulation or as separate formulations. Thus, the GIP-GLP-1 dual agonist compound employed in the context of the invention (or the salt or solvate thereof) may be used in combination with an antidiabetic agent including but not limited to metformin, a sulfonylurea, a glinide, a DPP-IV inhibitor, a glitazone, or insulin. In certain embodiments, the compound or salt or solvate thereof is used in combination with insulin, DPP-IV inhibitor, sulfonylurea or metformin, particularly sulfonylurea or metformin, for achieving adequate glycemic control. In certain preferred embodiments, the compound or salt or solvate thereof is used in combination with insulin or an insulin analogue for achieving adequate glycemic control. Examples of insulin analogues include but are not limited to Lantus®, NovoRapid®, Humalog®, NovoMix®, Actraphane HM®, Levemir® and Apidra®.

In certain embodiments, the GIP-GLP-1 dual agonist compound or salt or solvate thereof may further be used in combination with one or more of an anti-obesity agent, including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

In certain embodiments, the GIP-GLP-1 dual agonist compound or salt or solvate thereof may be used in combination with an anti-hypertension agent, including but not limited to an angiotensin-converting enzyme inhibitor, angiotensin II receptor blocker, diuretics, beta-blocker, or calcium channel blocker.

In certain embodiments, the GIP-GLP-1 dual agonist compound or salt thereof may be used in combination with an anti-dyslipidemia agent, including but not limited to a statin, a fibrate, a niacin and/or a cholesterol absorption inhibitor.

Synthesis of Compounds of the Invention

A nucleic acid molecule may encode the amino acid sequence of Formula I or a precursor thereof. The amino acid sequence encoded can be regarded as a precursor of a compound of the invention.

Typically, such nucleic acid sequences will be provided as expression constructs wherein the encoding nucleic acid is in functional linkage with appropriate control sequences to direct its expression. The expression construct may be provided in the context of a host cell capable of expressing (and optionally also secreting) the amino acid precursor, or in a cell-free expression system.

The invention provides a method of producing a GIP analogue of the invention, the method comprising expressing an amino acid precursor of the GIP analogue and modifying the precursor to provide the GIP analogue. The modification may comprise chemical modification of a Lys, Arg or Cys residue present at position 17 to introduce the lipophilic moiety, modification of the N- or C-terminus, and/or modification of any other amino acid side chains in the molecule (e.g. to introduce a non-naturally occurring amino acid residue).

The compounds of the invention may also be manufactured by standard peptide synthetic methods, e.g. by standard solid-phase or liquid-phase methodology, either stepwise or by fragment assembly, and isolating and purifying the final peptide compound product, or by any combinations of recombinant and synthetic methods.

It may be preferable to synthesize the peptide compounds of the invention by means of solid-phase or liquid-phase peptide synthesis. In this context, reference may be made to WO 98/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

EXAMPLES

The following examples demonstrate certain embodiments of the present invention. However, it is to be understood that these examples neither purport nor are they intended to be wholly definitive as to conditions and scope of this invention. The examples were carried out using standard techniques, which are well known and routine to those of skill in the art, except where otherwise described in detail. The following examples are presented for illustrative purposes only, and should not be construed in any way as limiting the scope of this invention.

Disclosed are GIP-GLP1 dual agonist compounds that exhibit signaling selectivity, and methods for screening these compounds. Signaling selectivity may be, for example, preferential pathway activation or preferential pathway inhibition, or both. The GIP-GLP1 dual agonist compounds may be useful for the treatment and/or prevention of diseases or conditions caused or characterized by excess body weight, including, but not limited to, obesity, morbid obesity, obesity linked inflammation, obesity linked gallbladder disease, obesity induced sleep apnea, metabolic syndrome, pre-diabetes, insulin resistance, glucose intolerance, type 2 diabetes, type I diabetes, hypertension, atherogenic dyslipidaemia, atherosclerosis, arteriosclerosis, coronary heart disease, peripheral artery disease, and stroke or microvascular disease.

While some embodiments of the invention have been described by way of illustration, it will be apparent that the invention can be put into practice with many different modifications, variations and adaptations, and with the use of numerous equivalents or alternative solutions that are within the scope of persons skilled in the art, without departing from the spirit of the invention or exceeding the scope of the claims.

All publications, patents, and patent applications referred to herein are herein incorporated by reference in their entirety to the same extent as if each individual publication, patent or patent application was specifically and individually indicated to be incorporated by reference in its entirety.

The methods used in the instant invention are described below, except where expressly indicated otherwise Example 1

General Synthesis of Acylated GIP Analogues

Solid phase peptide synthesis was performed on a CEM Liberty Peptide Synthesizer using standard Fmoc chemistry. TentaGel S Ram resin (1 g; 0.25 mmol/g) was swelled in NMP (10 ml) prior to use and transferred between tube and reaction vessel using DCM and NMP.
Coupling An Fmoc-amino acid in DMF/DCM (2:1; 0.2 M; 5 ml) was added to the resin in a CEM Discover microwave unit together with HATU/DMF or COMU/DMF (0.5 M; 2 ml) and DIPEA-DMF/DCM (2:1) (2.0 M; 1 ml). The coupling mixture was heated to 75° C. for 5 min while nitrogen was bubbled through the mixture. The resin was then washed with DMF (4×10 ml).
Deprotection Piperidine/DMF (20%; 10 ml) was added to the resin for initial deprotection and the mixture was heated by microwaves (30 sec; 40° C.). The reaction vessel was drained and a second portion of piperidine/NMP (20%; 10 ml) was added and heated (75° C.; 3 min.) again. The resin was then washed with DMF (6×10 ml).
Side Chain Acylation Fmoc-Lys(ivDde)-OH or alternatively another amino acid with an orthogonal side chain protective group was introduced at the position of the acylation. The N-terminal of the peptide backbone was then Boc-protected using Boc2O or alternatively by using a Boc-protected amino acid in the last coupling. While the peptide was still attached to the resin, the orthogonal side chain protective group was selectively cleaved using freshly prepared hydrazine hydrate (2-4%) in NMP for 2×15 min. The unprotected lysine side chain was first coupled with Fmoc-Glu-OtBu or another spacer amino acid, which was deprotected with piperidine and acylated with a lipophilic moiety using the peptide coupling methodology as described above.

Abbreviations employed are as follows:
COMU: 1-[(1-(cyano-2-ethoxy-2-oxoethylideneaminooxy)-dimethylamino-morpholinomethylene)]methanaminium hexaflourophosphate
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EtOH: ethanol
Et$_2$O: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane
Cleavage The resin was washed with EtOH (3×10 ml) and Et$_2$O (3×10 ml) and dried to constant weight at room temperature (r.t.). The crude peptide was cleaved from the resin by treatment with TFA/TIS/water (95/2.5/2.5; 40 ml, 2 h; r.t.). Most of the TFA was removed at reduced pressure and the crude peptide was precipitated and washed three times with diethylether and dried to constant weight at room temperature.
HPLC Purification of the Crude Peptide The crude peptide was purified to greater than 90% by preparative reverse phase HPLC using a PerSeptive Biosystems VISION Workstation equipped with a C-18 column (5 cm; 10 µm) and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The final product was characterized by HPLC and MS.

The synthesized compounds are shown in Table 1.

TABLE 1

| Compound No. | |
|---|---|
| 1 | H-Y-Aib-EGTFTSDYSIYLDK-K([17-carboxy-heptadecanoyl]-isoGlu-Peg3-Peg3)-AQRAFVEWLLAQGPSSGAPPPS-NH$_2$ (SEQ ID nO: 180) |

TABLE 1-continued

| Compound No. | |
|---|---|
| 2 | H-Y-Aib-EGTFTSDYSIYLDK-K([19-Carboxy-nonadecanoyl]-isoGlu-Peg3-Peg3)-AQRAFVEWLLAQGPSSGAPPPS-NH$_2$ (SEQ ID NO: 181) |
| 3 | H-Y-Aib-EGTFTSDYSIYLDK-K([17-carboxy-heptadecanoyl]-isoGlu)-AQRAFVEWLLAQGPSSGAPPPS-NH$_2$ (SEQ ID NO: 182) |
| 4 | H-Y-Aib-EGTFTSDYSIYLDK-K([17-carboxy-heptadecanoyl]-isoGlu-GSGSGG)-AQRAFVEWLLAQGPSSGAPPPS-NH$_2$ (SEQ ID NO: 177) |
| 5 | H-Y-Aib-EGTFTSDYSIYLDK-K([17-carboxy-heptadecanoyl]-Peg3-Peg3)-AQRAFVEWLLAQGPSSGAPPPS-NH$_2$ (SEQ ID NO: 184) |
| 6 | H-Y-Aib-EGTFTSDYSIYLDK-K([17-carboxy-heptadecanoyl]-isoGlu-Peg3-Peg3)-AQRAFVEWLLAQGPSSGAPPPS-NH$_2$ (SEQ ID NO: 178) |
| 7 | H-Y-Aib-EGTFTSDYSIYLDK-K([17-carboxy-heptadecanoyl]-Dapa-Peg3-Peg3)-AQRAFVEWLLAQGPSSGAPPPS-NH$_2$ (SEQ ID NO: 186) |
| 8 | H-Y-Aib-EGTFTSDYSIYLDK-K([19-Carboxy-nonadecanoyl]-isoGlu-Peg3-Peg3)-AQRAFVEWLLAQGPSSGAPPPS-NH$_2$ (SEQ ID NO: 187) |
| 9 | H-Y-DAla-EGTFTSDYSIYLDK-K([17-carboxy-heptadecanoyl]-isoGlu-Peg3-Peg3)-AQRAFVEWLLAQGPSSGAPPPS-NH$_2$ (SEQ ID NO: 188) |
| 10 | H-Y-Aib-EGTFTSDYSIYLEK-K([17-carboxy-heptadecanoyl]-isoGlu-Peg3-Peg3)-AAKEFVEWLLSAGPSSGAPPPS-NH$_2$ (SEQ ID NO: 189) |
| 11 | H-Y-Aib-EGTFTSDYSI-Aib-LDK-K([17-carboxy-heptadecanoyl]-isoGlu-Peg3-Peg3)-AQRAFVEWLLAQGPSSGAPPPS-NH$_2$ (SEQ ID NO: 190) |
| 12 | H-Y-Aib-EGTFTSDYSIYLDK-K([17-carboxy-heptadecanoyl]-isoGlu-Peg3-Peg3)-AQRAFVNWLLA-Aib-K-NH$_2$ (SEQ ID NO: 191) |
| 13 | H-Y-Aib-EGTFTSDYSIYLDE-K([17-carboxy-heptadecanoyl]-isoGlu-Peg3-Peg3)-AAKEFIEWLESA-NH$_2$ (SEQ ID NO: 192) |
| 14 | H-Y-Aib-EGTFTSDYSIALDK-K([17-carboxy-heptadecanoyl]-isoGlu-Peg3-Peg3)-AQRAFVNWLVA-Aib-KPSSGAPPPS-NH$_2$ (SEQ ID NO: 193) |
| 15 | H-Y-Aib-EGTFTSDYSIALDK-K[19-carboxy-nonadecanoyl]-isoGlu-Peg3-Peg3)-AQRAFVNWLVA-Aib-KPSSGAPPPS-NH$_2$ (SEQ ID NO: 194) |
| 16 | H-Y-Aib-EGTFTSDYSIALEK-K([17-carboxy-heptadecanoyl]-isoGlu-Peg3-Peg3)-AQRAFVEWLLAQK-NH$_2$ (SEQ ID NO: 195) |
| 17 | H-Y-Aib-EGTFTSDLSIALEK-K([17-carboxy-heptadecanoyl]-isoGlu-Peg3-Peg3)-AQRAFVEWLLAQK-NH$_2$ (SEQ ID NO: 196) |
| 18 | H-Y-Aib-EGTFTSDYSIYLEK-K([17-carboxy-heptadecanoyl]-isoGlu-Peg3-Peg3)-AQRAFVEWLLRA-NH$_2$ (SEQ ID NO: 197) |
| 19 | H-Y-Aib-EGTFTSDYSIALDK-K([17-carboxy-heptadecanoyl]-isoGlu-Peg3-Peg3)-AQRAFVNWLVA-Aib-K-NH$_2$ (SEQ ID NO: 198) |
| 20 | H-Y-Aib-EGTFTSDLSIALDK-K([17-carboxy-heptadecanoyl]-isoGlu-Peg3-Peg3)-AQRAFVNWLVA-Aib-K-NH$_2$ (SEQ ID NO: 199) |
| 21 | H-Y-Aib-EGTFTSDYSIALDK-K([17-carboxy-heptadecanoyl]-isoGlu-Peg3-Peg3)-AQRAFVEWLVA-Aib-K-NH$_2$ (SEQ ID NO: 200) |
| 22 | H-Y-Aib-EGTFTSDYSIALEK-K([17-carboxy-heptadecanoyl]-isoGlu-Peg3-Peg3)-AQRAFVEWLEAQGPSSGAPPPS-NH$_2$ (SEQ ID NO: 201) |
| 23 | H-Y-Aib-EGTFTSDYSIALEK-K([17-carboxy-heptadecanoyl]-isoGlu-Peg3-Peg3)-AQRAFVEWLEAQK-NH$_2$ (SEQ ID NO: 202) |
| 24 | H-Y-Aib-EGTFTSDLSIALEK-K([17-carboxy-heptadecanoyl]-isoGlu-Peg3-Peg3)-AQRAFVEWLEAQK-NH$_2$ (SEQ ID NO: 203) |
| 25 | H-Y-Aib-EGTFTSDYSIALEK-K[19-carboxy-nonadecanoyl]-isoGlu-Peg3-Peg3)-AQRAFVEWLLAQK-NH$_2$ (SEQ ID NO: 204) |
| 26 | H-Y-Aib-EGTFTSDLSIALEK-K[19-carboxy-nonadecanoyl]-isoGlu-Peg3-Peg3)-AQRAFVEWLEAQK-NH$_2$ (SEQ ID NO: 205) |
| 28 | H-Y-Aib-EGTFTSDLSIALEK-K([19-carboxy-nonadecanoyl]-isoGlu-Peg3-Peg3)-AQRAFVEWLLAQK-NH$_2$ (SEQ ID NO: 206) |

TABLE 1-continued

| Compound No. | |
|---|---|
| 29 | H-Y-Aib-EGTFTSDYSIYLEK-K([19-carboxy-nonadecanoyl]-isoGlu-Peg3-Peg3)-AQRAFVEWLLRA-NH$_2$ (SEQ ID NO: 207) |
| 30 | H-Y-DAla-EGTFTSDYSIYLDK-K([19-carboxy-nonadecanoyl]-isoGlu-Peg3-Peg3)-AQRAFVEWLLAQGPSSGAPPPS-NH$_2$ (SEQ ID NO: 208) |
| 31 | H-Y-Aib-EGTFTSDYSIALEK-K([19-carboxy-nonadecanoyl]-isoGlu-Peg3-Peg3)-AQRAFVEWLLAQGPSSGAPPPS-NH$_2$ (SEQ ID NO: 209) |
| 32 | H-Y-DAla-EGTFTSDYSIALEK-K([19-carboxy-nonadecanoyl]-isoGlu-Peg3-Peg3)-AQRAFVEWLLAQGPSSGAPPPS-NH$_2$ (SEQ ID NO: 210) |
| 33 | H-Y-Aib-EGTFTSDLSIALEK-K([19-carboxy-nonadecanoyl]-isoGlu-Peg3-Peg3)-AQRAFVEWLLAQGPSSGAPPPS-NH$_2$ (SEQ ID NO: 211) |
| 34 | H-Y-Aib-EGTFTSDLSIALEK-K([19-carboxy-nonadecanoyl]-isoGlu-Peg3-Peg3)-AQRAFVEWLLAQKPSSGAPPPS-NH$_2$ (SEQ ID NO: 212) |
| 35 | H-Y-Aib-EGTFTSDYSIYLDK-K([19-carboxy-nonadecanoyl]-Peg3-Peg3)-AQRAFVEWLLAQGPSSGAPPPS-NH$_2$ (SEQ ID NO: 213) |
| 36 | H-Y-Aib-EGTFTSDYSIYLDK-K([19-carboxy-nonadecanoyl]-IsoGlu)-AQRAFVEWLLAQGPSSGAPPPS-NH$_2$ (SEQ ID NO: 214) |
| 37 | H-Y-Aib-EGTFTSDYSIYLDK-K([19-carboxy-nonadecanoyl]-Dapa-Peg3-Peg3)-AQRAFVEWLLAQGPSSGAPPPS-NH$_2$ (SEQ ID NO: 215) |
| 38 | H-Y-Aib-EGTFTSDYSIALDK-K([19-carboxy-nonadecanoyl]-isoGlu-Peg3-Peg3)-AQRAFVEWLLAQKPSSGAPPPS-NH$_2$ (SEQ ID NO: 216) |
| 39 | H-Y-DAla-EGTFTSDYSIALDK-K([19-carboxy-nonadecanoyl]-isoGlu-Peg3-Peg3)-AQRAFVEWLLAQKPSSGAPPPS-NH$_2$ (SEQ ID NO: 217) |
| 40 | H-Y-Aib-EGTFTSDYSIALDK-K([19-carboxy-nonadecanoyl]-isoGlu-Peg3-Peg3)-AQRAFVEWLLAAPSSGAPPPS-NH$_2$ (SEQ ID NO: 218) |
| 41 | H-Y-Aib-EGTFTSDYSIALDK-K([19-carboxy-nonadecanoyl]-isoGlu-Peg3-Peg3)-AAKEFVEWLLSAGPSSGAPPPS-NH$_2$ (SEQ ID NO: 219) |
| 42 | H-Y-Aib-EGTFTSDYSIALDK-K([19-carboxy-nonadecanoyl]-isoGlu-Peg3-Peg3)-AQRAFVEWLLAQGPSSGAPPPS-NH$_2$ (SEQ ID NO: 220) |
| 43 | H-Y-Aib-EGTFTSDYSIALDE-K([19-carboxy-nonadecanoyl]-isoGlu-Peg3-Peg3)-AQRAFVEWLLAQGPSSGAPPPS-NH$_2$ (SEQ ID NO: 221) |
| 44 | H-Y-Aib-EGTFTSDYSIALDE-K([19-carboxy-nonadecanoyl]-isoGlu-Peg3-Peg3)-AQRAFVEWLLAAGPSSGAPPPS-NH$_2$ (SEQ ID NO: 222) |
| 45 | H-Y-Aib-EGTFTSDYSIALDK-K([19-carboxy-nonadecanoyl]-isoGlu-Peg3-Peg3)-AQKAFVEWLLAAGPSSGAPPPS-NH$_2$ (SEQ ID NO: 223) |
| 46 | H-Y-Aib-EGTFTSDYSIYLDK-K([19-carboxy-nonadecanoyl]-isoGlu-Peg3-Peg3)-AQREFVEWLLAQGPSSGAPPPS-NH$_2$ (SEQ ID NO: 224) |
| 47 | H-Y-Aib-EGTFTSDYSIALDK-K([19-carboxy-nonadecanoyl]-isoGlu-Peg3-Peg3)-AQREFVEWLLAQGPSSGAPPPS-NH$_2$ (SEQ ID NO: 225) |
| 48 | H-Y-Aib-EGTFTSDYSIALDK-K([19-carboxy-nonadecanoyl]-isoGlu-Peg3-Peg3)-AQKEFVEWLLAQGPSSGAPPPS-NH$_2$ (SEQ ID NO: 226) |
| 49 | H-Y-Aib-EGTFTSDYSIALDK-K([19-carboxy-nonadecanoyl]-isoGlu-Peg3-Peg3)-AQKEFVEWLLAAGPSSGAPPPS-NH$_2$ (SEQ ID NO: 227) |
| 50 | H-Y-Aib-EGTFTSDYSIALDK-K([19-carboxy-nonadecanoyl]-isoGlu-Peg3-Peg3)-AQRAFIEWLLAQGPSSGAPPPS-NH$_2$ (SEQ ID NO: 228) |
| 51 | H-Y-Aib-EGTFTSDYSIALDK-K([17-carboxy-heptadecanoyl]-isoGlu-Peg3-Peg3)-AQRAFVEWLLAQGPSSGAPPPS-NH$_2$ (SEQ ID NO: 229) |
| 52 | H-Y-Aib-EGTFTSDYSIALDK-K((19-Carboxy-nonadecanoyl)-[(Piperazine-1-yl)-acetyl]-Peg3-Peg3)-AQRAFVEWLLAQGPSSGAPPPS-NH$_2$ (SEQ ID NO: 230) |
| 53 | H-Y-Aib-EGTFTSDYSIALDK-K((19-Carboxy-nonadecanoyl)-[(Piperazine-1-yl)-acetyl]-Peg3-Peg3)-AQKEFVEWLLAAGPSSGAPPPS-NH$_2$ (SEQ ID NO: 231) |

TABLE 1-continued

| Compound No. | |
|---|---|
| 54 | H-Y-Aib-EGTFTSDYSIYLDK-K([19-Carboxy-nonadecanoyl]-isoGlu-Peg3-Peg3)-AQRAFVEWLLAEGPSSGAPPPS-NH$_2$ (SEQ ID NO: 232) |
| 55 | H-Y-Aib-EGTFTSDYSIALDK-K([19-carboxy-nonadecanoyl]-isoGlu-Peg3-Peg3)-AQRAFVEWLLAEGPSSGAPPPS-NH$_2$ (SEQ ID NO: 233) |
| 56 | H-Y-Aib-EGTFTSDYSIALDK-K([19-carboxy-nonadecanoyl]-isoGlu-Peg3-Peg3)-AQRAFVEWLLAEPSSGAPPPS-NH$_2$ (SEQ ID NO: 234) |

Synthesis of Compound No. 10

Solid phase peptide synthesis was performed on a CEM Liberty Peptide Synthesizer using standard Fmoc chemistry. TentaGel S Ram S resin (1.05 g; 0.25 mmol/g) was swelled in DMF (10 ml) prior to use and transferred between tube and reaction vessel using DCM and DMF.

Coupling

An Fmoc-amino acid in DMF/DCM (2:1; 0.2 M; 5 ml) was added to the resin in a CEM Discover microwave unit together with COMU/DMF (0.5 M; 2 ml) and DIPEA-DMF/DCM (2:1) (2.0 M; 1 ml). The coupling mixture was heated to 75° C. for 5 min while nitrogen was bubbled through the mixture. The resin was then washed with DMF (4×10 ml). Fmoc-Tyr(OtBu)-Ser(Psi Me,Me)-OH pseudoproline was used for amino acid number 29 and 30 counting from the C-terminal. Lys17 was incorporated as Fmoc-Lys(Dde)-OH for orthogonal coupling. The first 9 amino acids and amino acid number 24 (counting from the C-terminal) was double couple meaning the building block was coupled twice before deprotection. Boc-Tyr(tBu)-OH was incorporated as the final building block in the N-terminal.

Deprotection

Piperidine/DMF (20%; 10 ml) was added to the resin for initial deprotection and the mixture was heated by microwaves (30 sec; 40° C.). The reaction vessel was drained and a second portion of piperidine/DMF (20%; 10 ml) was added and heated (75° C.; 3 min.) again. The resin was then washed with DMF (6×10 ml).

Side Chain Acylation

While the peptide was still attached to the resin, the orthogonal side chain protective group was selectively cleaved using freshly prepared hydrazine hydrate (2-4%) in NMP for 2×15 min. The unprotected lysine side chain was first coupled with Fmoc-Glu-OtBu and the two Peg3 buildingblocks using standard coupling and deprotection conditions as explained aboved. Lastly the lipophilic moiety was incorporated as a 17-carboxy-heptadecanoic acid mono tert butyl ester again using standard coupling conditions.

Cleavage

The resin was washed with EtOH (3×10 ml) and Et2O (3×10 ml) and dried to constant weight at room temperature (r.t.). The crude peptide was cleaved from the resin by treatment with TFA/TIS/H$_2$O (95/2.5/2.5; 60 ml, 2 h; r.t.). Most of the TFA was removed at reduced pressure and the crude peptide was precipitated and washed three times with diethylether and dried to constant weight at room temperature.

HPLC Purification of the Crude Peptide

The crude peptide was first purified from 45% by preparative reverse phase HPLC using a PerSeptive Biosystems VISION Workstation equipped with a Gemini NX 5µ C-18 110A, 10×250 mm column and a fraction collector and run at 35 ml/min with a gradient of buffer A (0.1% TFA, aq.) and buffer B (0.1% TFA, 90% MeCN, aq.). Fractions were analyzed by analytical HPLC and MS and relevant fractions were pooled and lyophilized. The product (96 mg) was analysed to give a purity of 91% as characterized by HPLC and MS. Calculated monoisotopic mass=4921.51, found 4921.45.

Example 2

Human GIP Receptor (GIP R) and GLP-1 Receptor (GLP-1R) Activity Assay

In vitro effects of peptide conjugates of the invention were assessed by measuring the induction of cAMP following stimulation of the respective receptor by GIP, GLP1 or analogues of these, as outlined in the invention, using the AlphaSceen® cAMP kit from Perkin-Elmer according to instructions. Briefly, HEK293 cells expressing the human GIP R or GLP-1R (stable cell lines generated through transfection of the cDNA for human GIP R or GLP-1 and selection of stable clones) were seeded at 30,000 cells/well in 96-well microtiter plates coated with 0.01% poly-L-lysine, and grown for 1 day in culture in 200 µl growth medium (DMEM, 10% FCS, Penicillin (100 IU/ml), Streptomycin (100 µg/ml)). On the day of analysis, growth medium was removed and the cells were washed once with 150 ml Tyrode's buffer (Tyrode's Salts (9.6 g/l), 10 mM HEPES, pH 7.4). Cells were then incubated in 100 ml Assay buffer (0.1% W/V Alkali-treated Casein and 100 µM IBMX in Tyrode's Buffer) containing increasing concentrations of control and test compounds for 15 min at 37° C. The Assay buffer was removed and cells are lysed in 80 µl Lysis buffer (0.1% w/v BSA, 5 mM HEPES, 0.3% v/v Tween-20) per well. From each well 10 µl lysed cells was transferred to a 384-well plate and mixed with 15 µl bead-mix (1 Unit/15 µl anti-cAMP Acceptor Beads, 1 Unit/15 µl Donor Beads, and 1 Unit/15 µl Biotinylated cAMP in Assay Buffer). The plates were mixed and incubated in the dark for an hour at room temperature before measuring using an Envision™ plate reader (Perkin-Elmer).

Results were converted into cAMP concentrations using a cAMP standard curve prepared in KRBH buffer containing 0.1% (v/v) DMSO. The resulting cAMP curves were plotted as absolute cAMP concentrations (nM) over log (test compound concentration) and analyzed using the curve fitting program XLfit.

Parameters calculated to describe both the potency as well as the agonistic activity of each test compound on the receptors were:

EC50, a concentration resulting in a half-maximal elevation of cAMP levels, reflecting the potency of the test compound. The results are summarized in Table 2, 2a and 3. The most comprehensive data are summarized in Table 3.

TABLE 2

EC$_{50}$ average values of the compounds on the GIP-R and GLP1-R compared to control peptides.

| Compound | hGIP-R cAMP (nM) | hGLP1-R cAMP (nM) |
| --- | --- | --- |
| hGIP | 0.003 | NA |
| hGLP-1 | >10 | >10 |
| 1 | 0.0055 | 0.012 |
| 2 | 0.0049 | 0.0083 |
| 3 | 0.0086 | 0.011 |
| 4 | 0.0087 | 0.010 |
| 5 | 0.012 | 0.014 |
| 6 | 0.0049 | 0.016 |
| 7 | 0.011 | 0.012 |
| 8 | 0.0053 | 0.012 |
| 9 | 0.0088 | 0.038 |
| 10 | 0.016 | 0.028 |
| 11 | 0.0047 | 0.013 |
| 12 | 0.011 | 0.016 |
| 14 | 0.0064* | 0.0080* |
| 15 | 0.0080 | 0.0088 |
| 16 | 0.0081 | 0.015 |
| 17 | 0.011 | 0.0062 |
| 18 | 0.014 | 0.022 |
| 19 | 0.0073 | 0.014 |
| 20 | 0.0097 | 0.011 |
| 21 | 0.0068 | 0.011 |
| 22 | 0.06 | 0.061 |
| 23 | 0.2 | 0.044 |
| 24 | 0.26 | 0.011 |
| 25 | 0.009 | 0.011 |
| 26 | NT | 0.014 |
| 27 | 0.06 | 0.061 |
| 28 | 0.024 | 0.017 |
| 29 | 0.025 | 0.033 |
| 30 | 0.015 | 0.028 |
| 31 | 0.007 | 0.016 |
| 32 | 0.016 | 0.040 |
| 33 | 0.009 | 0.014 |
| 34 | 0.012 | 0.015 |

NT: Not Tested
*These EC50 values (hGIP-R and GLP1-R) for compound 14 are believed to be in error.

TABLE 2a

A secondary assay study with EC$_{50}$ average values of the compounds 1 to 21 on the GIP-R and GLP1-R.

| Compound | hGIP-R cAMP (nM) | hGLP1-R cAMP (nM) |
| --- | --- | --- |
| 1 | 0.006 | 0.015 |
| 2 | 0.008 | 0.011 |
| 3 | 0.009 | 0.011 |
| 4 | 0.009 | 0.010 |
| 5 | 0.011 | 0.014 |
| 6 | 0.005 | 0.016 |
| 7 | 0.011 | 0.012 |
| 8 | 0.005 | 0.012 |
| 9 | 0.009 | 0.039 |
| 10 | 0.016 | 0.029 |
| 11 | 0.005 | 0.013 |
| 12 | 0.012 | 0.017 |
| 14 | 0.147 | 0.056 |
| 15 | 0.006 | 0.008 |
| 16 | 0.008 | 0.009 |
| 17 | 0.008 | 0.015 |
| 18 | 0.011 | 0.006 |
| 19 | 0.014 | 0.022 |
| 20 | 0.007 | 0.014 |
| 21 | 0.010 | 0.010 |

TABLE 3

EC$_{50}$ average values of all the compounds on the GIP-R and GLP1-R.

| Compound | hGIP-R cAMP (nM) | hGLP-1-R cAMP (nM) |
| --- | --- | --- |
| 1 | 0.006 | 0.015 |
| 2 | 0.008 | 0.011 |
| 3 | 0.009 | 0.011 |
| 4 | 0.009 | 0.010 |
| 5 | 0.012 | 0.014 |
| 6 | 0.005 | 0.016 |
| 7 | 0.011 | 0.012 |
| 8 | 0.005 | 0.012 |
| 9 | 0.009 | 0.038 |
| 10 | 0.016 | 0.028 |
| 11 | 0.005 | 0.013 |
| 12 | 0.011 | 0.016 |
| 13 | 0.150 | 0.057 |
| 14 | 0.006 | 0.008 |
| 15 | 0.008 | 0.009 |
| 16 | 0.008 | 0.015 |
| 17 | 0.011 | 0.006 |
| 18 | 0.014 | 0.022 |
| 19 | 0.007 | 0.014 |
| 20 | 0.010 | 0.011 |
| 21 | 0.007 | 0.011 |
| 22 | 0.060 | 0.061 |
| 23 | 0.200 | 0.044 |
| 24 | 0.260 | 0.011 |
| 25 | 0.009 | 0.011 |
| 26 | 0.580 | 0.014 |
| 27 | 0.060 | 0.061 |
| 28 | 0.024 | 0.015 |
| 29 | 0.025 | 0.033 |
| 30 | 0.017 | 0.035 |
| 31 | 0.008 | 0.017 |
| 32 | 0.018 | 0.056 |
| 33 | 0.009 | 0.014 |
| 34 | 0.012 | 0.015 |
| 35 | 0.016 | 0.012 |
| 36 | 0.010 | 0.015 |
| 37 | 0.017 | 0.014 |
| 38 | 0.005 | 0.012 |
| 39 | 0.011 | 0.006 |
| 40 | 0.023 | 0.021 |
| 41 | 0.015 | 0.038 |
| 42 | 0.009 | 0.017 |
| 43 | 0.005 | 0.016 |
| 44 | 0.007 | 0.015 |
| 45 | 0.005 | 0.024 |
| 46 | 0.006 | 0.010 |
| 47 | 0.005 | 0.016 |
| 48 | 0.006 | 0.052 |
| 49 | 0.009 | 0.053 |
| 50 | 0.007 | 0.015 |
| 51 | 0.005 | 0.017 |
| 52 | 0.010 | 0.012 |
| 53 | 0.006 | 0.014 |
| 54 | 0.016 | 0.012 |
| 55 | 0.016 | 0.013 |
| 56 | 0.025 | 0.033 |

Example 3

Pharmacokinetics of Selected Compounds in Mice
Method

C57BL/6J mice (males with a body weight of approximately 25 g) were given either a single subcutaneous (s.c.) bolus or a single intravenous (i.v.) bolus of each peptide to be tested.

Following s.c. administration of the selected compounds (50, 100 or 200 nmol/kg), blood samples were drawn at 8 (eight) timepoints up to 72 hours post-dose. Following i.v. administration of the selected compounds (50, 100 or 200 nmol/kg), blood samples were drawn at 8 (eight) timepoints up to 48 hours post-dose. Blood samples were drawn by sublingual bleeding. The dosing vehicle was a phosphate buffer containing mannitol (pH 7.5).

At each sampling time point, samples from two mice were drawn, i.e. 16 mice were included for each compound and each administration route. The mice were euthanized immediately after blood sampling by cervical dislocation. Plasma samples were analyzed after solid phase extraction (SPE) or protein precipitation followed by liquid chromatography mass spectrometry (LC-MS/MS). Mean plasma concentrations were used for calculation of the pharmacokinetic parameters using the non-compartmental approach in Phoenix WinNonlin 6.3. Plasma terminal elimination half-life (T½) was determined as $\ln(2)/\lambda z$ where $\lambda z$ is the magnitude of the slope of the log linear regression of the log concentration versus time profile during the terminal phase. Bioavailability was determined as $AUC_{inf}$ (s.c.)/$AUC_{inf}$ (i.v.)× 100, where $AUC_{inf}$ is the area under the plasma concentration–time curve extrapolated to infinity ($AUC_{inf}=AUC_{last}+C_{last}/\lambda z$, where $C_{last}$ is the last observed plasma concentration). $T_{max}$ is the post-dose time where the maximal plasma concentration was observed. The results are summarized in Table 4.

TABLE 4

Terminal elimination half-life (h) and bioavailability in mice following s.c. and i.v. administration of selected compounds.

| Compound | T½ (h.) | | Tmax (h.) | Bioavailability |
|---|---|---|---|---|
| | i.v | s.c. | s.c. | s.c. |
| Semaglutide | 7.8 | 7.5 | 4 | 100% |
| 1 | 10.8 | 9.1 | 6 | 90% |
| 2 | 16.6 | 16.5 | 6 | 83% |
| 3 | 9.1 | — | 8 | 89% |
| 4 | 8.7 | 10.8 | 6 | 100%* |
| 15 | 17.3 | — | 8 | 95% |
| 16 | 7.4 | — | 6 | 50% |
| 8 | 17.2 | — | 8 | 54% |
| 28 | 13.6 | 14.1 | 2 | 93% |
| 30 | 17.1 | 15.9 | 8 | 83% |
| 31 | 11.7 | 15.1 | 8 | 88% |
| 32 | 17.4 | 11.8 | 8 | 100%* |
| 34 | 14.9 | 17.1 | 8 | 79% |

—: Parameter not calculated
*The bioavailability was capped to 100%

Example 4

IPGTT (Intraperitoneal Glucose Tolerance Test) in diabetic db/db mice.

Figure 1B:
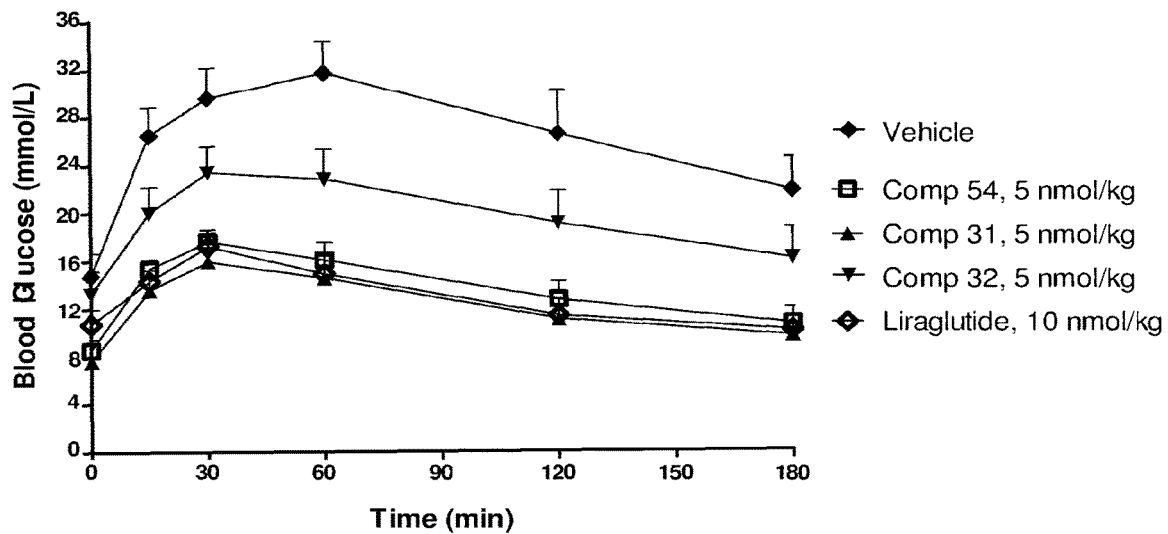
Figure 1C:
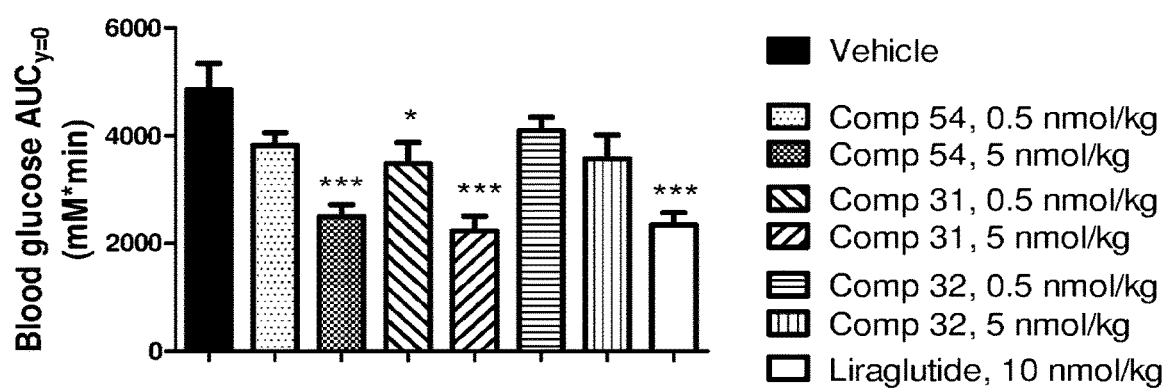
Figure 2A:
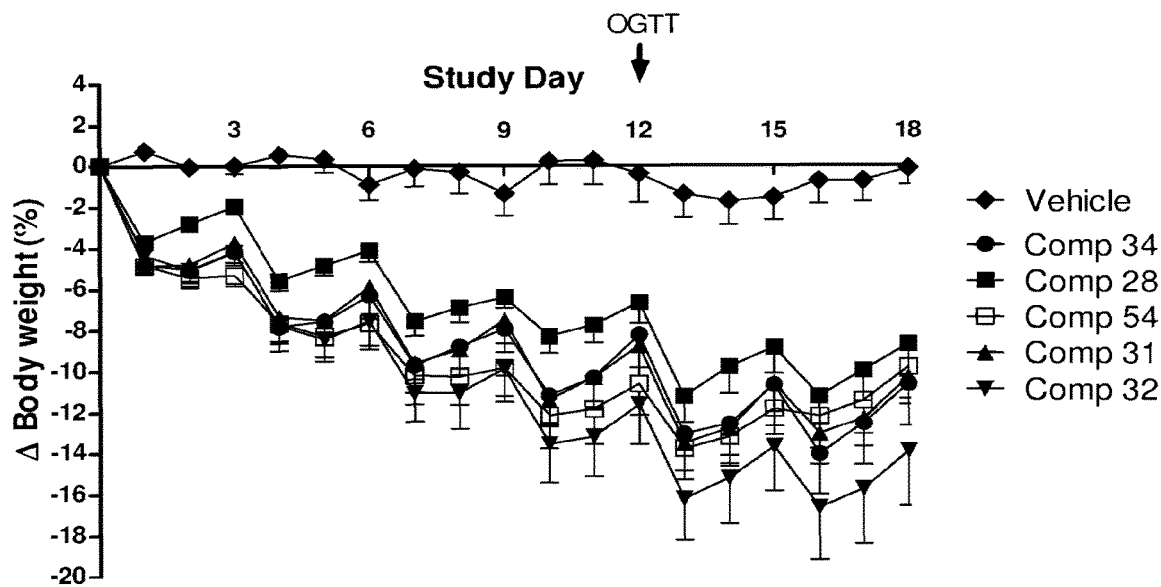
FIGS. 2A-2B: Relative body weight changes (delta Δ=body weight at each study day–body weight at day 0) in DIO mice during the 18-days study period (FIG. 2A) and absolute body weight changes (delta Δ=body weight at day 18–body weight at day 0) (FIG. 2B). Animals were treated once every third day with s.c. injections of vehicle or GIP-GLP-1 dual acting receptor agonists (3 nmol/kg). Data are means±SEM; n=7-9.
Figure 2B:
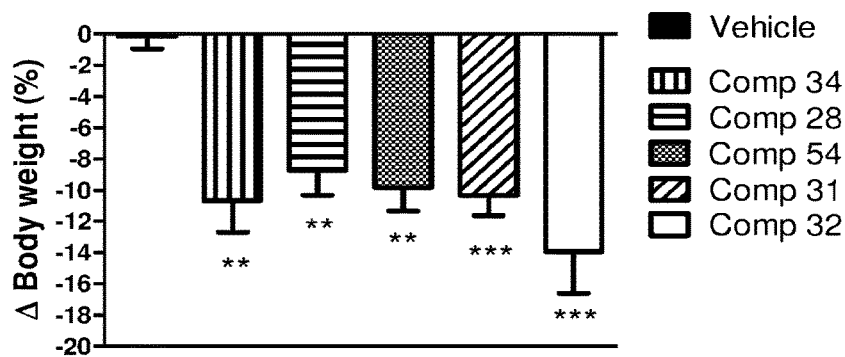
Figure 3:
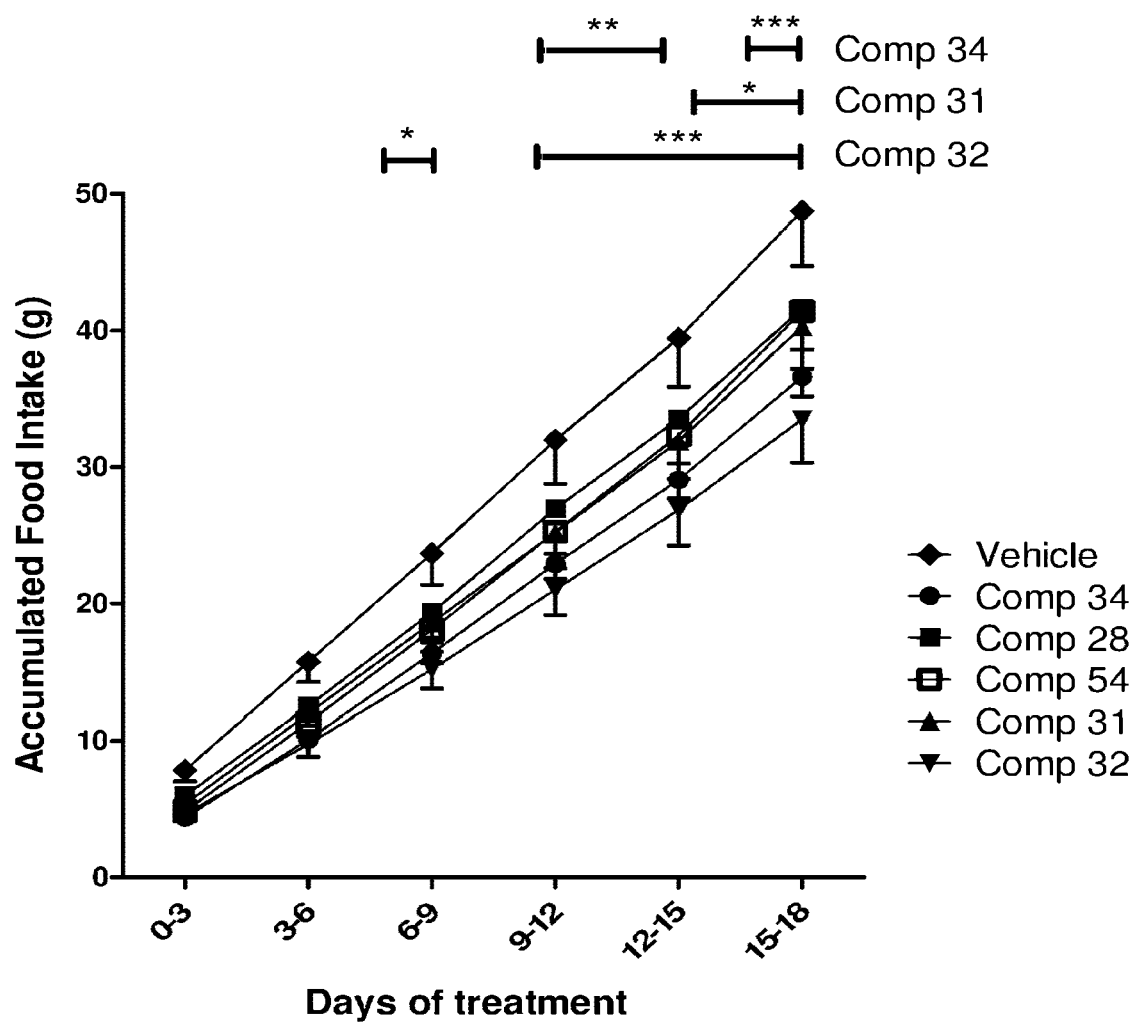
FIG. 3: Accumulated food intake in DIO mice. Animals were treated once every third day with s.c. injections of vehicle or GIP-GLP-1 dual acting receptor agonists (3 nmol/kg). Data are means±SEM; n=4-5.
Figure 4A:
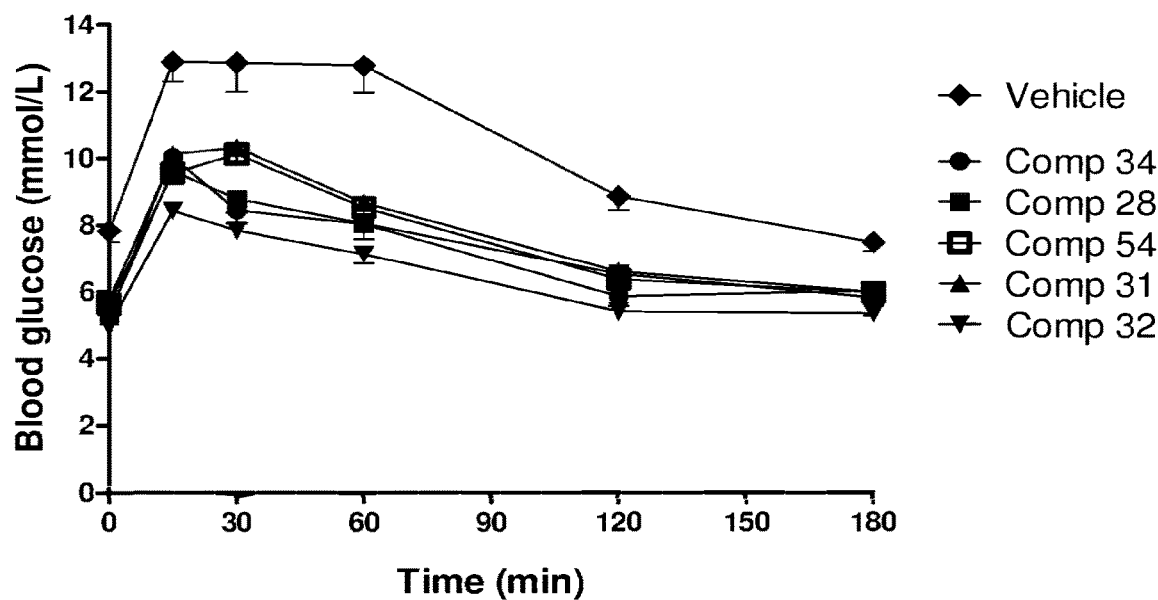
FIGS. 4A-4B: Blood glucose levels during the OGTT (FIG. 4A) and area under the blood glucose curves (AUC) (FIG. 4B) on day 12 in 5-hour fasted DIO mice. The mice were injected with vehicle or test substances (3 nmol/kg) 5 hours prior to the oral gavage of glucose (t=0). Data are means±SEM; n=7-9.
Figure 4B:
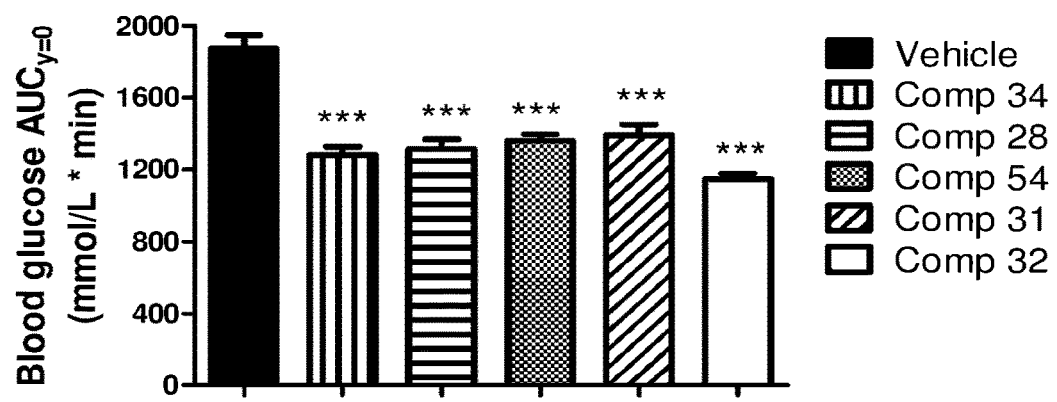
Figure 5:
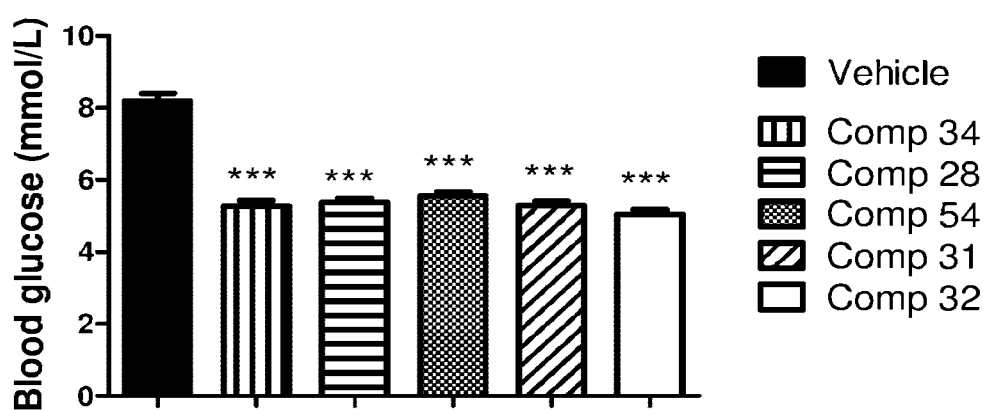
FIG. 5: Blood glucose on day 18 in 5-hour fasted DIO mice. The mice were injected with vehicle or GIP-GLP-1 dual acting receptor agonists (3 nmol/kg) 5 hours prior to the blood sampling. Data are means±SEM; n=7-9.

Male diabetic db/db (BKS.Cg-Dock7$^m$+/+Lepr$^{ob}$J) mice (Charles River, France), were maintained on normal chow (Altromin 1324, Brogaarden A/S, Gentofte, Denmark) and domestic quality water with added citric acid to pH~3.6. The animals were housed in groups of n=4 in a light-, temperature-, and humidity-controlled room (12:12 h light-dark cycle, with lights on at 06.00-18.00 hr; 23±0.5° C.; 50-80% relative humidity). Mice, 11-12 weeks old, were fasted for 5 hr before the IPGTT. GIP-GLP-1 dual acting receptor agonists (0.5 and 5 nmol/kg) and vehicle were administered subcutaneously (s.c.) 22 hours before the intraperitoneal (i.p.) injection of glucose (t=0 min; 1 g/kg; 5 ml/kg). The GLP-1 analogue liraglutide (10 nmol/kg) was administered subcutaneously 4 hours before the i.p. injection of glucose. Tail vein blood was sampled at time t=0 (before glucose administration), 15, 30, 60, 120, and 180 min for measurements of blood glucose. Results are shown in FIGS. 1A-1C.

Example 5

Sub-Chronic Effects of GIP-GLP-1 Receptor Dual Acting Agonists on Body Weight, Food Intake, Glucose Tolerance and Fasted Blood Glucose in Diet-Induced Obese (DIO) $C_{57}BL/6J$ Mice Male C57BL/6J mice (Taconic A/S, Denmark) fed highfat diet (60% of total energy from fat, D12492, Research Diet Inc.) for approximately 6 months were used. The animals were housed in groups of n=3-4 in a light-, temperature-, and humidity-controlled room (12:12 h light-dark cycle, with lights on at 06.00-18.00 hr; 20-22° C.; 50-80% relative humidity). Mice from cages of 4 were split into two cages (2 mice per cage) two weeks prior to start of the mock phase. All mice were mock-treated (once daily s.c. injection of vehicle) for a week to acclimatize the animals to handling and injections. Subsequently, the mice were stratified according to body weight into 6 groups (n=7-9). The average starting body weight was 45-46 grams. Animals were thereafter treated once every third day with s.c. injections (5 ml/kg) of vehicle (25 mM phosphate, 125 mM sodium chloride buffer, pH 7.4), or GIP-GLP-1 dual acting receptor agonists (3 nmol/kg). First day of dosing was on day 0 and last day of dosing on day 18. The daily injections were given in the morning (at 8.00-9.00). Body weight was determined daily throughout the study. Food and water intake per cage were measured every third day of the study (in conjunction with dosing). On day 12, animals were fasted for 5 hours and an oral glucose tolerance test (OGTT) was performed. The animals were dosed in the morning 5 hour before the oral gavage of glucose (t=0 min; 2 g/kg; 5 ml/kg). Tail vein blood was sampled at time t=0 (before glucose administration), 15, 30, 60, 120, and 180 min for measurements of blood glucose. On day 18, animals were fasted for 5 hours, and blood samples were taken for measurements of blood glucose. The animals were dosed in the morning 5 hour before the blood sampling. After the final blood sampling, the mice were euthanized. Results are shown in FIGS. 2-5.

Statistical analyses were performed using Graph Pad Prism version 5. The measured parameters were compared using one-way or two-way ANOVAs followed by Dunnett's Multiple Comparison Tests vs. vehicle group or by Bonferroni post tests vs. vehicle group, respectively. Differences were considered statistically significant at p<0.05. Statistical differences vs vehicle: *p<0.05, p<0.01, *p<0.001.

SEQUENCE LISTING

<160> NUMBER OF SEQ ID NOS: 236

<210> SEQ ID NO 1
<211> LENGTH: 39
<212> TYPE: PRT
<213> ORGANISM: Artificial sequence

```
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 1

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 2

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu)

<400> SEQUENCE: 3

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 4
```

<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-GSGSGG)

<400> SEQUENCE: 4

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-Peg3-Peg3)

<400> SEQUENCE: 5

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 6
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
    Peg3-Peg3)

<400> SEQUENCE: 6

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 7
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-Dapa-Peg3-Peg3)

<400> SEQUENCE: 7

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3-
      Peg3)

<400> SEQUENCE: 8

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: SITE
<222> LOCATION: (2)..(2)
<223> OTHER INFORMATION: Xaa is DAla
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 9

Tyr Xaa Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser

```
                    20                  25                  30

Ser Gly Ala Pro Pro Ser
        35

<210> SEQ ID NO 10
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 10

Tyr Ala Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala Gly Pro Ser
                20                  25                  30

Ser Gly Ala Pro Pro Ser
        35

<210> SEQ ID NO 11
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(13)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 11

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Gly Pro Ser
                20                  25                  30

Ser Gly Ala Pro Pro Ser
        35

<210> SEQ ID NO 12
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 12
```

```
Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala Lys
            20                  25                  30

<210> SEQ ID NO 13
<211> LENGTH: 29
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 13

Tyr Ala Glu Gly Thr Phe Thr Ser Asp Tyr Ser Ile Tyr Leu Asp Glu
1               5                   10                  15

Lys Ala Ala Lys Glu Phe Ile Glu Trp Leu Glu Ser Ala
            20                  25

<210> SEQ ID NO 14
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 14

Tyr Ala Glu Gly Thr Phe Thr Ser Asp Tyr Ser Ile Ala Leu Asp Lys
1               5                   10                  15

Lys Ala Gln Arg Ala Phe Val Asn Trp Leu Val Ala Ala Lys Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 15

Tyr Ala Glu Gly Thr Phe Thr Ser Asp Tyr Ser Ile Ala Leu Asp Lys
```

Lys Ala Gln Arg Ala Phe Val Asn Trp Leu Val Ala Ala Lys Pro Ser
            20                  25                  30

Ser Gly Ala Pro Pro Ser
            35

<210> SEQ ID NO 16
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 16

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln Lys
            20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 17

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Leu Ala Gln Lys
            20                  25                  30

<210> SEQ ID NO 18
<211> LENGTH: 29
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 18

Tyr Ala Glu Gly Thr Phe Thr Ser Asp Tyr Ser Ile Tyr Leu Glu Lys
1               5                   10                  15

Lys Ala Gln Arg Ala Phe Val Glu Trp Leu Leu Arg Ala
            20                  25

<210> SEQ ID NO 19
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 19

Tyr Ala Glu Gly Thr Phe Thr Ser Asp Tyr Ser Ile Ala Leu Asp Lys
1               5                   10                  15

Lys Ala Gln Arg Ala Phe Val Asn Trp Leu Val Ala Ala Lys
            20                  25                  30

<210> SEQ ID NO 20
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 20

Tyr Ala Glu Gly Thr Phe Thr Ser Asp Leu Ser Ile Ala Leu Asp Lys
1               5                   10                  15

Lys Ala Gln Arg Ala Phe Val Asn Trp Leu Val Ala Ala Lys
            20                  25                  30

<210> SEQ ID NO 21
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 21

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Val Ala Ala Lys
            20                  25                  30

<210> SEQ ID NO 22
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
    Peg3)

<400> SEQUENCE: 22

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Glu Ala Gln Gly Pro Ser
            20                  25                  30

Ser Gly Ala Pro Pro Pro Ser
        35

<210> SEQ ID NO 23
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
    Peg3)

<400> SEQUENCE: 23

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Glu Ala Gln Lys
            20                  25                  30

<210> SEQ ID NO 24
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
    Peg3)

<400> SEQUENCE: 24

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Glu Ala Gln Lys
            20                  25                  30

```
<210> SEQ ID NO 25
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 25

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln Lys
            20                  25                  30

<210> SEQ ID NO 26
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 26

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Glu Ala Gln Lys
            20                  25                  30

<210> SEQ ID NO 27
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 27

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Leu Ala Gln Lys
            20                  25                  30

<210> SEQ ID NO 28
<211> LENGTH: 29
<212> TYPE: PRT
<213> ORGANISM: Artificial sequence
<220> FEATURE:
<223> OTHER INFORMATION: Synthetic construct
<220> FEATURE:
```

```
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 28

Tyr Ala Glu Gly Thr Phe Thr Ser Asp Tyr Ser Ile Tyr Leu Glu Lys
1               5                   10                  15

Lys Ala Gln Arg Ala Phe Val Glu Trp Leu Leu Arg Ala
            20                  25

<210> SEQ ID NO 29
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: SITE
<222> LOCATION: (2)..(2)
<223> OTHER INFORMATION: DAla
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 29

Tyr Xaa Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 30

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 31
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: SITE
```

```
<222> LOCATION: (2)..(2)
<223> OTHER INFORMATION: DAla
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 31

Tyr Xaa Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 32
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 32

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 33
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 33

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Leu Ala Gln Lys Pro Ser
            20                  25                  30

Ser Gly Ala Pro Pro Pro Ser
        35

<210> SEQ ID NO 34
<211> LENGTH: 39
<212> TYPE: PRT
<213> ORGANISM: Artificial sequence
<220> FEATURE:
<223> OTHER INFORMATION: Synthetic construct
```

-continued

```
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-carboxy-nonadecanoyl]-Peg3-Peg3)
<220> FEATURE:
<221> NAME/KEY: SITE
<222> LOCATION: (39)..(39)
<223> OTHER INFORMATION: Linked to R2, wherein R2 is -NH2 or -OH

<400> SEQUENCE: 34

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-carboxy-nonadecanoyl]-IsoGlu)
<220> FEATURE:
<221> NAME/KEY: SITE
<222> LOCATION: (39)..(39)
<223> OTHER INFORMATION: Linked to R2, wherein R2 is -NH2 or -OH

<400> SEQUENCE: 35

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: MOD_RES
```

```
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-carboxy-nonadecanoyl]-Dapa-Peg3-Peg3)
<220> FEATURE:
<221> NAME/KEY: SITE
<222> LOCATION: (39)..(39)
<223> OTHER INFORMATION: Linked to R2, wherein R2 is -NH2 or -OH

<400> SEQUENCE: 36

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 37

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Lys Pro Ser
            20                  25                  30

Ser Gly Ala Pro Pro Pro Ser
        35

<210> SEQ ID NO 38
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: SITE
<222> LOCATION: (2)..(2)
<223> OTHER INFORMATION: DAla
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 38

Tyr Xaa Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Lys Pro Ser
            20                  25                  30

Ser Gly Ala Pro Pro Pro Ser
        35

<210> SEQ ID NO 39
<211> LENGTH: 38
```

```
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 39

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Ala Pro Ser Ser
            20                  25                  30

Gly Ala Pro Pro Ser
        35

<210> SEQ ID NO 40
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 40

Tyr Ala Glu Gly Thr Phe Thr Ser Asp Tyr Ser Ile Ala Leu Asp Lys
1               5                   10                  15

Lys Ala Ala Lys Glu Phe Val Glu Trp Leu Leu Ser Ala Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 41

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Ser
        35
```

<210> SEQ ID NO 42
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 42

Tyr Ala Glu Gly Thr Phe Thr Ser Asp Tyr Ser Ile Ala Leu Asp Glu
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 43
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 43

Tyr Ala Glu Gly Thr Phe Thr Ser Asp Tyr Ser Ile Ala Leu Asp Glu
1               5                   10                  15

Lys Ala Gln Arg Ala Phe Val Glu Trp Leu Leu Ala Ala Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 44

Tyr Ala Glu Gly Thr Phe Thr Ser Asp Tyr Ser Ile Ala Leu Asp Lys
1               5                   10                  15

Lys Ala Gln Lys Ala Phe Val Glu Trp Leu Leu Ala Ala Gly Pro Ser
            20                  25                  30

Ser Gly Ala Pro Pro Pro Ser
        35

```
<210> SEQ ID NO 45
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 45

Tyr Ala Glu Gly Thr Phe Thr Ser Asp Tyr Ser Ile Tyr Leu Asp Lys
1               5                   10                  15

Lys Ala Gln Arg Glu Phe Val Glu Trp Leu Leu Ala Gln Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 46

Tyr Ala Glu Gly Thr Phe Thr Ser Asp Tyr Ser Ile Ala Leu Asp Lys
1               5                   10                  15

Lys Ala Gln Arg Glu Phe Val Glu Trp Leu Leu Ala Gln Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 47

Tyr Ala Glu Gly Thr Phe Thr Ser Asp Tyr Ser Ile Ala Leu Asp Lys
1               5                   10                  15

Lys Ala Gln Lys Glu Phe Val Glu Trp Leu Leu Ala Gln Gly Pro Ser
            20                  25                  30
```

Ser Gly Ala Pro Pro Pro Ser
        35

<210> SEQ ID NO 48
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 48

Tyr Ala Glu Gly Thr Phe Thr Ser Asp Tyr Ser Ile Ala Leu Asp Lys
1               5                   10                  15

Lys Ala Gln Lys Glu Phe Val Glu Trp Leu Leu Ala Ala Gly Pro Ser
            20                  25                  30

Ser Gly Ala Pro Pro Pro Ser
        35

<210> SEQ ID NO 49
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 49

Tyr Ala Glu Gly Thr Phe Thr Ser Asp Tyr Ser Ile Ala Leu Asp Lys
1               5                   10                  15

Lys Ala Gln Arg Ala Phe Ile Glu Trp Leu Leu Ala Gln Gly Pro Ser
            20                  25                  30

Ser Gly Ala Pro Pro Pro Ser
        35

<210> SEQ ID NO 50
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 50

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-[(Piperazine-1-
      yl)-acetyl]-Peg3-Peg3)

<400> SEQUENCE: 51

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 52
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-[(Piperazine-1-
      yl)-acetyl]-Peg3-Peg3)

<400> SEQUENCE: 52

Tyr Ala Glu Gly Thr Phe Thr Ser Asp Tyr Ser Ile Ala Leu Asp Lys
1               5                   10                  15

Lys Ala Gln Lys Glu Phe Val Glu Trp Leu Leu Ala Ala Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 53

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Glu Gly Pro Ser
            20                  25                  30

Ser Gly Ala Pro Pro Ser
        35

<210> SEQ ID NO 54
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 54

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Glu Gly Pro Ser
            20                  25                  30

Ser Gly Ala Pro Pro Pro Ser
        35

<210> SEQ ID NO 55
<211> LENGTH: 38
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 55

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Glu Pro Ser Ser
            20                  25                  30

Gly Ala Pro Pro Pro Ser
        35

<210> SEQ ID NO 56
<211> LENGTH: 30
<212> TYPE: PRT
<213> ORGANISM: Artificial sequence
<220> FEATURE:
<223> OTHER INFORMATION: Synthetic construct: GIP analogue - General
      Formula I of PCT/EP2014/073970
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: VARIANT

```
<222> LOCATION: (2)..(2)
<223> OTHER INFORMATION: Xaa is selected from Aib and D-Ala
<220> FEATURE:
<221> NAME/KEY: VARIANT
<222> LOCATION: (10)..(10)
<223> OTHER INFORMATION: Xaa is selected from Tyr and Leu
<220> FEATURE:
<221> NAME/KEY: VARIANT
<222> LOCATION: (13)..(13)
<223> OTHER INFORMATION: Xaa is selected from Ala, Tyr and Aib
<220> FEATURE:
<221> NAME/KEY: VARIANT
<222> LOCATION: (15)..(15)
<223> OTHER INFORMATION: Xaa is selected from Asp and Glu
<220> FEATURE:
<221> NAME/KEY: VARIANT
<222> LOCATION: (16)..(16)
<223> OTHER INFORMATION: Xaa is selected from Glu and Lys
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: VARIANT
<222> LOCATION: (19)..(19)
<223> OTHER INFORMATION: Xaa is selected from Gln and Ala
<220> FEATURE:
<221> NAME/KEY: VARIANT
<222> LOCATION: (20)..(20)
<223> OTHER INFORMATION: Xaa is selected from Lys and Arg
<220> FEATURE:
<221> NAME/KEY: VARIANT
<222> LOCATION: (21)..(21)
<223> OTHER INFORMATION: Xaa is selected from Ala and Glu
<220> FEATURE:
<221> NAME/KEY: VARIANT
<222> LOCATION: (23)..(23)
<223> OTHER INFORMATION: Xaa is selected from Val and Ile
<220> FEATURE:
<221> NAME/KEY: VARIANT
<222> LOCATION: (24)..(24)
<223> OTHER INFORMATION: Xaa is selected from Asn and Glu
<220> FEATURE:
<221> NAME/KEY: VARIANT
<222> LOCATION: (27)..(27)
<223> OTHER INFORMATION: Xaa is selected from Leu, Glu and Val
<220> FEATURE:
<221> NAME/KEY: VARIANT
<222> LOCATION: (28)..(28)
<223> OTHER INFORMATION: Xaa is selected from Ala, Ser and Arg
<220> FEATURE:
<221> NAME/KEY: SITE
<222> LOCATION: (29)..(29)
<223> OTHER INFORMATION: If Xaa 30 is absent, Xaa 29 is linked to R2,
      wherein R2 is -NH2 or -OH
<220> FEATURE:
<221> NAME/KEY: VARIANT
<222> LOCATION: (29)..(29)
<223> OTHER INFORMATION: In Claim 1 of PCT/EP2014/073970, Xaa is
      selected from Aib, Ala, and Gln
<220> FEATURE:
<221> NAME/KEY: VARIANT
<222> LOCATION: (29)..(29)
<223> OTHER INFORMATION: In Claim 2 of PCT/EP2014/073970, Xaa is
      selected from Aib, Ala, Glu and Gln
<220> FEATURE:
<221> NAME/KEY: SITE
<222> LOCATION: (30)..(30)
<223> OTHER INFORMATION: If present, linked to R2, wherein R2 is -NH2 or
      -OH
<220> FEATURE:
<221> NAME/KEY: VARIANT
<222> LOCATION: (30)..(30)
<223> OTHER INFORMATION: Xaa may be present or absent. If present, Xaa
      is selected from Lys, Gly and Y1, wherein Y1 is selected from SEQ
      ID NO: 57, SEQ ID NO: 58, SEQ ID NO: 59, SEQ ID NO: 60, and SEQ ID
```

NO: 61

<400> SEQUENCE: 56

Tyr Xaa Glu Gly Thr Phe Thr Ser Asp Xaa Ser Ile Xaa Leu Xaa Xaa
1               5                   10                  15

Xaa Ala Xaa Xaa Xaa Phe Xaa Xaa Trp Leu Xaa Xaa Xaa Xaa
            20                  25                  30

<210> SEQ ID NO 57
<211> LENGTH: 10
<212> TYPE: PRT
<213> ORGANISM: Artificial sequence
<220> FEATURE:
<223> OTHER INFORMATION: Synthetic construct: Y1 of SEQ ID NO: 56 and
      SEQ ID NO: 62

<400> SEQUENCE: 57

Gly Pro Ser Ser Gly Ala Pro Pro Pro Ser
1               5                   10

<210> SEQ ID NO 58
<211> LENGTH: 10
<212> TYPE: PRT
<213> ORGANISM: Artificial sequence
<220> FEATURE:
<223> OTHER INFORMATION: Synthetic construct: Y1 of SEQ ID NO: 56 and
      SEQ ID NO: 62

<400> SEQUENCE: 58

Lys Pro Ser Ser Gly Ala Pro Pro Pro Ser
1               5                   10

<210> SEQ ID NO 59
<211> LENGTH: 9
<212> TYPE: PRT
<213> ORGANISM: Artificial sequence
<220> FEATURE:
<223> OTHER INFORMATION: Synthetic construct: Y1 of SEQ ID NO: 56 and
      SEQ ID NO: 62

<400> SEQUENCE: 59

Gly Pro Ser Ser Gly Ala Pro Pro Ser
1               5

<210> SEQ ID NO 60
<211> LENGTH: 9
<212> TYPE: PRT
<213> ORGANISM: Artificial sequence
<220> FEATURE:
<223> OTHER INFORMATION: Synthetic construct: Y1 of SEQ ID NO: 56 and
      SEQ ID NO: 62

<400> SEQUENCE: 60

Pro Ser Ser Gly Ala Pro Pro Pro Ser
1               5

<210> SEQ ID NO 61
<211> LENGTH: 8
<212> TYPE: PRT
<213> ORGANISM: Artificial sequence
<220> FEATURE:
<223> OTHER INFORMATION: Synthetic construct: Y1 of SEQ ID NO: 56 and
      SEQ ID NO: 62

<400> SEQUENCE: 61

Pro Ser Ser Gly Ala Pro Pro Ser
1               5

```
<210> SEQ ID NO 62
<211> LENGTH: 30
<212> TYPE: PRT
<213> ORGANISM: Artificial sequence
<220> FEATURE:
<223> OTHER INFORMATION: Synthetic construct: GIP analogue - General
      Formula II of PCT/EP2014/073970
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: VARIANT
<222> LOCATION: (2)..(2)
<223> OTHER INFORMATION: Xaa is selected from Aib and D-Ala
<220> FEATURE:
<221> NAME/KEY: VARIANT
<222> LOCATION: (13)..(13)
<223> OTHER INFORMATION: Xaa is selected from Ala, Tyr
<220> FEATURE:
<221> NAME/KEY: VARIANT
<222> LOCATION: (15)..(15)
<223> OTHER INFORMATION: Xaa is selected from Asp and Glu
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: VARIANT
<222> LOCATION: (21)..(21)
<223> OTHER INFORMATION: Xaa is selected from Ala and Glu
<220> FEATURE:
<221> NAME/KEY: VARIANT
<222> LOCATION: (23)..(23)
<223> OTHER INFORMATION: Xaa is selected from Val and Ile
<220> FEATURE:
<221> NAME/KEY: VARIANT
<222> LOCATION: (24)..(24)
<223> OTHER INFORMATION: Xaa is selected from Asn and Glu
<220> FEATURE:
<221> NAME/KEY: VARIANT
<222> LOCATION: (28)..(28)
<223> OTHER INFORMATION: Xaa is selected from Ala, Ser
<220> FEATURE:
<221> NAME/KEY: SITE
<222> LOCATION: (29)..(29)
<223> OTHER INFORMATION: If Xaa 30 is absent, Xaa 29 is linked to R2,
      wherein R2 is -NH2 or -OH
<220> FEATURE:
<221> NAME/KEY: VARIANT
<222> LOCATION: (29)..(29)
<223> OTHER INFORMATION: Xaa is selected from Ala, Glu and Gln
<220> FEATURE:
<221> NAME/KEY: SITE
<222> LOCATION: (30)..(30)
<223> OTHER INFORMATION: If present, linked to R2, wherein R2 is -NH2 or
      -OH
<220> FEATURE:
<221> NAME/KEY: VARIANT
<222> LOCATION: (30)..(30)
<223> OTHER INFORMATION: Xaa may be present or absent. If present, Xaa
      is selected from Lys, Gly and Y1, wherein Y1 is selected from SEQ
      ID NO: 57, SEQ ID NO: 58, SEQ ID NO: 59, SEQ ID NO: 60, and SEQ ID
      NO: 61

<400> SEQUENCE: 62

Tyr Xaa Glu Gly Thr Phe Thr Ser Asp Tyr Ser Ile Xaa Leu Xaa Glu
1               5                   10                  15

Xaa Ala Ala Arg Xaa Phe Xaa Xaa Trp Leu Leu Xaa Xaa Xaa
            20                  25                  30
```

<210> SEQ ID NO 63
<211> LENGTH: 29
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib

<400> SEQUENCE: 63

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 64
<211> LENGTH: 29
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib

<400> SEQUENCE: 64

Tyr Ala Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala
            20                  25

<210> SEQ ID NO 65
<211> LENGTH: 29
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Aib

<400> SEQUENCE: 65

Tyr Ala Glu Gly Thr Phe Thr Ser Asp Tyr Ser Ile Tyr Leu Asp Glu
1               5                   10                  15

Lys Ala Ala Lys Glu Phe Ile Glu Trp Leu Glu Ser Ala
            20                  25

<210> SEQ ID NO 66
<211> LENGTH: 29
<212> TYPE: PRT
<213> ORGANISM: Artificial sequence
<220> FEATURE:
<223> OTHER INFORMATION: Synthetic construct: Residues 1-29 of GIP
    analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
    Arg, Orn or Cys in which the side chain is conjugated to a
    substituent having the formula -Z1 or -Z2-Z1, where Z1 and Z2 are
    as defined in PCT/EP2014/073970

```
<400> SEQUENCE: 66

Tyr Ala Glu Gly Thr Phe Thr Ser Asp Tyr Ser Ile Tyr Leu Asp Lys
1               5                   10                  15

Xaa Ala Gln Arg Ala Phe Val Glu Trp Leu Leu Ala Gln
            20                  25

<210> SEQ ID NO 67
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (2)..(2)
<223> OTHER INFORMATION: Xaa is DAla
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 67

Tyr Xaa Glu Gly Thr Phe Thr Ser Asp Tyr Ser Ile Tyr Leu Asp Lys
1               5                   10                  15

Xaa Ala Gln Arg Ala Phe Val Glu Trp Leu Leu Ala Gln
            20                  25

<210> SEQ ID NO 68
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 68

Tyr Ala Glu Gly Thr Phe Thr Ser Asp Tyr Ser Ile Tyr Leu Glu Lys
1               5                   10                  15

Xaa Ala Ala Lys Glu Phe Val Glu Trp Leu Leu Ser Ala
            20                  25

<210> SEQ ID NO 69
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (13)..(13)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 69

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Gln
            20                  25

<210> SEQ ID NO 70
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 70

Tyr Ala Glu Gly Thr Phe Thr Ser Asp Tyr Ser Ile Tyr Leu Asp Lys
1               5                   10                  15

Xaa Ala Gln Arg Ala Phe Val Asn Trp Leu Leu Ala Ala
            20                  25

<210> SEQ ID NO 71
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 71

Tyr Ala Glu Gly Thr Phe Thr Ser Asp Tyr Ser Ile Tyr Leu Asp Glu
1               5                   10                  15

Xaa Ala Ala Lys Glu Phe Ile Glu Trp Leu Glu Ser Ala
            20                  25
```

```
<210> SEQ ID NO 72
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 72

Tyr Ala Glu Gly Thr Phe Thr Ser Asp Tyr Ser Ile Ala Leu Asp Lys
1               5                   10                  15

Xaa Ala Gln Arg Ala Phe Val Asn Trp Leu Val Ala Ala
            20                  25

<210> SEQ ID NO 73
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 73

Tyr Ala Glu Gly Thr Phe Thr Ser Asp Tyr Ser Ile Ala Leu Glu Lys
1               5                   10                  15

Xaa Ala Gln Arg Ala Phe Val Glu Trp Leu Leu Ala Gln
            20                  25

<210> SEQ ID NO 74
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
```

<400> SEQUENCE: 74

Tyr Ala Glu Gly Thr Phe Thr Ser Asp Leu Ser Ile Ala Leu Glu Lys
1               5                   10                  15

Xaa Ala Gln Arg Ala Phe Val Glu Trp Leu Leu Ala Gln
            20                  25

<210> SEQ ID NO 75
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 75

Tyr Ala Glu Gly Thr Phe Thr Ser Asp Tyr Ser Ile Tyr Leu Glu Lys
1               5                   10                  15

Xaa Ala Gln Arg Ala Phe Val Glu Trp Leu Leu Arg Ala
            20                  25

<210> SEQ ID NO 76
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 76

Tyr Ala Glu Gly Thr Phe Thr Ser Asp Leu Ser Ile Ala Leu Asp Lys
1               5                   10                  15

Xaa Ala Gln Arg Ala Phe Val Asn Trp Leu Val Ala Ala
            20                  25

<210> SEQ ID NO 77
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)

```
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 77

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Val Ala Ala
            20                  25

<210> SEQ ID NO 78
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 78

Tyr Ala Glu Gly Thr Phe Thr Ser Asp Tyr Ser Ile Ala Leu Glu Lys
1               5                   10                  15

Xaa Ala Gln Arg Ala Phe Val Glu Trp Leu Glu Ala Gln
            20                  25

<210> SEQ ID NO 79
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 79

Tyr Ala Glu Gly Thr Phe Thr Ser Asp Leu Ser Ile Ala Leu Glu Lys
1               5                   10                  15

Xaa Ala Gln Arg Ala Phe Val Glu Trp Leu Glu Ala Gln
            20                  25

<210> SEQ ID NO 80
```

```
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (2)..(2)
<223> OTHER INFORMATION: Xaa is DAla
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 80

Tyr Xaa Glu Gly Thr Phe Thr Ser Asp Tyr Ser Ile Ala Leu Glu Lys
1               5                   10                  15

Xaa Ala Gln Arg Ala Phe Val Glu Trp Leu Leu Ala Gln
            20                  25

<210> SEQ ID NO 81
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 81

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Gln
            20                  25

<210> SEQ ID NO 82
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (2)..(2)
<223> OTHER INFORMATION: Xaa is DAla
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 82

Tyr Xaa Glu Gly Thr Phe Thr Ser Asp Tyr Ser Ile Ala Leu Asp Lys
1               5                   10                  15
```

Xaa Ala Gln Arg Ala Phe Val Glu Trp Leu Leu Ala Gln
            20                  25

<210> SEQ ID NO 83
<211> LENGTH: 30
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 83

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Ala Pro
            20                  25                  30

<210> SEQ ID NO 84
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 84

Tyr Ala Glu Gly Thr Phe Thr Ser Asp Tyr Ser Ile Ala Leu Asp Lys
1               5                   10                  15

Xaa Ala Ala Lys Glu Phe Val Glu Trp Leu Leu Ser Ala
            20                  25

<210> SEQ ID NO 85
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

```
<400> SEQUENCE: 85

Tyr Ala Glu Gly Thr Phe Thr Ser Asp Tyr Ser Ile Ala Leu Asp Glu
1               5                   10                  15

Xaa Ala Gln Arg Ala Phe Val Glu Trp Leu Leu Ala Gln
            20                  25

<210> SEQ ID NO 86
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 86

Tyr Ala Glu Gly Thr Phe Thr Ser Asp Tyr Ser Ile Ala Leu Asp Lys
1               5                   10                  15

Xaa Ala Gln Lys Ala Phe Val Glu Trp Leu Leu Ala Ala
            20                  25

<210> SEQ ID NO 87
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 87

Tyr Ala Glu Gly Thr Phe Thr Ser Asp Tyr Ser Ile Ala Leu Asp Glu
1               5                   10                  15

Xaa Ala Gln Arg Ala Phe Val Glu Trp Leu Leu Ala Ala
            20                  25

<210> SEQ ID NO 88
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
```

```
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 88

Tyr Ala Glu Gly Thr Phe Thr Ser Asp Tyr Ser Ile Tyr Leu Asp Lys
1               5                   10                  15

Xaa Ala Gln Arg Glu Phe Val Glu Trp Leu Leu Ala Gln
            20                  25

<210> SEQ ID NO 89
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 89

Tyr Ala Glu Gly Thr Phe Thr Ser Asp Tyr Ser Ile Ala Leu Asp Lys
1               5                   10                  15

Xaa Ala Gln Arg Glu Phe Val Glu Trp Leu Leu Ala Gln
            20                  25

<210> SEQ ID NO 90
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 90

Tyr Ala Glu Gly Thr Phe Thr Ser Asp Tyr Ser Ile Ala Leu Asp Lys
1               5                   10                  15

Xaa Ala Gln Lys Glu Phe Val Glu Trp Leu Leu Ala Gln
            20                  25

<210> SEQ ID NO 91
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
```

```
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 91

Tyr Ala Glu Gly Thr Phe Thr Ser Asp Tyr Ser Ile Ala Leu Asp Lys
1               5                   10                  15

Xaa Ala Gln Lys Glu Phe Val Glu Trp Leu Leu Ala Ala
            20                  25

<210> SEQ ID NO 92
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 92

Tyr Ala Glu Gly Thr Phe Thr Ser Asp Tyr Ser Ile Ala Leu Asp Lys
1               5                   10                  15

Xaa Ala Gln Arg Ala Phe Ile Glu Trp Leu Leu Ala Gln
            20                  25

<210> SEQ ID NO 93
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 93

Tyr Ala Glu Gly Thr Phe Thr Ser Asp Tyr Ser Ile Tyr Leu Asp Lys
1               5                   10                  15

Xaa Ala Gln Arg Ala Phe Val Glu Trp Leu Leu Ala Glu
            20                  25

<210> SEQ ID NO 94
<211> LENGTH: 29
<212> TYPE: PRT
<213> ORGANISM: Artificial sequence
```

```
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 94

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Glu
            20                  25

<210> SEQ ID NO 95
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 95

Tyr Ala Glu Gly Thr Phe Thr Ser Asp Tyr Ser Ile Tyr Leu Asp Lys
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 96
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: SITE
<222> LOCATION: (2)..(2)
<223> OTHER INFORMATION: Xaa is DAla
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 96

Tyr Xaa Glu Gly Thr Phe Thr Ser Asp Tyr Ser Ile Tyr Leu Asp Lys
1               5                   10                  15
```

```
Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 97
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 97

Tyr Ala Glu Gly Thr Phe Thr Ser Asp Tyr Ser Ile Tyr Leu Glu Lys
1               5                   10                  15

Xaa Ala Ala Lys Glu Phe Val Glu Trp Leu Leu Ser Ala Gly Pro Ser
            20                  25                  30

Ser Gly Ala Pro Pro Pro Ser
        35

<210> SEQ ID NO 98
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (13)..(13)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 98

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 99
<211> LENGTH: 30
<212> TYPE: PRT
<213> ORGANISM: Artificial sequence
<220> FEATURE:
<223> OTHER INFORMATION: Synthetic construct: Peptide backbone of GIP
```

```
         analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 99

Tyr Ala Glu Gly Thr Phe Thr Ser Asp Tyr Ser Ile Tyr Leu Asp Lys
1               5                   10                  15

Xaa Ala Gln Arg Ala Phe Val Asn Trp Leu Leu Ala Ala Lys
            20                  25                  30

<210> SEQ ID NO 100
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 100

Tyr Ala Glu Gly Thr Phe Thr Ser Asp Tyr Ser Ile Ala Leu Asp Lys
1               5                   10                  15

Xaa Ala Gln Arg Ala Phe Val Asn Trp Leu Val Ala Ala Lys Pro Ser
            20                  25                  30

Ser Gly Ala Pro Pro Pro Ser
        35

<210> SEQ ID NO 101
<211> LENGTH: 30
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
```

```
<400> SEQUENCE: 101

Tyr Ala Glu Gly Thr Phe Thr Ser Asp Tyr Ser Ile Ala Leu Glu Lys
1               5                   10                  15

Xaa Ala Gln Arg Ala Phe Val Glu Trp Leu Leu Ala Gln Lys
            20                  25                  30

<210> SEQ ID NO 102
<211> LENGTH: 30
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 102

Tyr Ala Glu Gly Thr Phe Thr Ser Asp Leu Ser Ile Ala Leu Glu Lys
1               5                   10                  15

Xaa Ala Gln Arg Ala Phe Val Glu Trp Leu Leu Ala Gln Lys
            20                  25                  30

<210> SEQ ID NO 103
<211> LENGTH: 30
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 103

Tyr Ala Glu Gly Thr Phe Thr Ser Asp Tyr Ser Ile Ala Leu Asp Lys
1               5                   10                  15

Xaa Ala Gln Arg Ala Phe Val Asn Trp Leu Val Ala Ala Lys
            20                  25                  30

<210> SEQ ID NO 104
<211> LENGTH: 30
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
```

```
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 104

Tyr Ala Glu Gly Thr Phe Thr Ser Asp Leu Ser Ile Ala Leu Asp Lys
1               5                   10                  15

Xaa Ala Gln Arg Ala Phe Val Asn Trp Leu Val Ala Ala Lys
            20                  25                  30

<210> SEQ ID NO 105
<211> LENGTH: 30
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
<220> FEATURE:
<221> NAME/KEY: MOD_RES
<222> LOCATION: (29)..(29)
<223> OTHER INFORMATION: Aib

<400> SEQUENCE: 105

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Val Ala Ala Lys
            20                  25                  30

<210> SEQ ID NO 106
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 106

Tyr Ala Glu Gly Thr Phe Thr Ser Asp Tyr Ser Ile Ala Leu Glu Lys
1               5                   10                  15
```

```
Xaa Ala Gln Arg Ala Phe Val Glu Trp Leu Glu Ala Gln Gly Pro Ser
            20                  25                  30

Ser Gly Ala Pro Pro Pro Ser
        35

<210> SEQ ID NO 107
<211> LENGTH: 30
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 107

Tyr Ala Glu Gly Thr Phe Thr Ser Asp Tyr Ser Ile Ala Leu Glu Lys
1               5                   10                  15

Xaa Ala Gln Arg Ala Phe Val Glu Trp Leu Glu Ala Gln Lys
            20                  25                  30

<210> SEQ ID NO 108
<211> LENGTH: 30
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 108

Tyr Ala Glu Gly Thr Phe Thr Ser Asp Leu Ser Ile Ala Leu Glu Lys
1               5                   10                  15

Xaa Ala Gln Arg Ala Phe Val Glu Trp Leu Glu Ala Gln Lys
            20                  25                  30

<210> SEQ ID NO 109
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
```

-continued substituent having the formula -Z1 or -Z2-Z1, where Z1 and Z2 are
as defined in PCT/EP2014/073970

<400> SEQUENCE: 109

Tyr Ala Glu Gly Thr Phe Thr Ser Asp Tyr Ser Ile Ala Leu Glu Lys
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 110
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: SITE
<222> LOCATION: (2)..(2)
<223> OTHER INFORMATION: Xaa is DAla
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 110

Tyr Xaa Glu Gly Thr Phe Thr Ser Asp Tyr Ser Ile Ala Leu Glu Lys
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 111
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 111

Tyr Ala Glu Gly Thr Phe Thr Ser Asp Leu Ser Ile Ala Leu Glu Lys
1               5                   10                  15

Xaa Ala Gln Arg Ala Phe Val Glu Trp Leu Leu Ala Gln Lys Pro Ser
            20                  25                  30

Ser Gly Ala Pro Pro Pro Ser
        35

<210> SEQ ID NO 112
<211> LENGTH: 39

```
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 112

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Gln Lys Pro Ser
            20                  25                  30

Ser Gly Ala Pro Pro Pro Ser
        35

<210> SEQ ID NO 113
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: SITE
<222> LOCATION: (2)..(2)
<223> OTHER INFORMATION: Xaa is DAla
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 113

Tyr Xaa Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Gln Lys Pro Ser
            20                  25                  30

Ser Gly Ala Pro Pro Pro Ser
        35

<210> SEQ ID NO 114
<211> LENGTH: 38
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970
```

<400> SEQUENCE: 114

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Ala Pro Ser Ser
            20                  25                  30

Gly Ala Pro Pro Ser
        35

<210> SEQ ID NO 115
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 115

Tyr Ala Glu Gly Thr Phe Thr Ser Asp Tyr Ser Ile Ala Leu Asp Lys
1               5                   10                  15

Xaa Ala Ala Lys Glu Phe Val Glu Trp Leu Leu Ser Ala Gly Pro Ser
            20                  25                  30

Ser Gly Ala Pro Pro Pro Ser
        35

<210> SEQ ID NO 116
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 116

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 117
<211> LENGTH: 39
<212> TYPE: PRT
<213> ORGANISM: Artificial sequence
<220> FEATURE:

```
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 117

Tyr Ala Glu Gly Thr Phe Thr Ser Asp Tyr Ser Ile Ala Leu Asp Glu
1               5                   10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 118
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 118

Tyr Ala Glu Gly Thr Phe Thr Ser Asp Tyr Ser Ile Ala Leu Asp Glu
1               5                   10                  15

Xaa Ala Gln Arg Ala Phe Val Glu Trp Leu Leu Ala Ala Gly Pro Ser
            20                  25                  30

Ser Gly Ala Pro Pro Pro Ser
        35

<210> SEQ ID NO 119
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 119

Tyr Ala Glu Gly Thr Phe Thr Ser Asp Tyr Ser Ile Ala Leu Asp Lys
```

```
                1               5                  10                  15
Xaa Ala Gln Lys Ala Phe Val Glu Trp Leu Leu Ala Ala Gly Pro Ser
            20                  25                  30

Ser Gly Ala Pro Pro Ser
            35

<210> SEQ ID NO 120
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 120

Tyr Ala Glu Gly Thr Phe Thr Ser Asp Tyr Ser Ile Tyr Leu Asp Lys
1               5                  10                  15

Xaa Ala Gln Arg Glu Phe Val Glu Trp Leu Leu Ala Gln Gly Pro Ser
            20                  25                  30

Ser Gly Ala Pro Pro Ser
            35

<210> SEQ ID NO 121
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 121

Tyr Ala Glu Gly Thr Phe Thr Ser Asp Tyr Ser Ile Ala Leu Asp Lys
1               5                  10                  15

Xaa Ala Gln Arg Glu Phe Val Glu Trp Leu Leu Ala Gln Gly Pro Ser
            20                  25                  30

Ser Gly Ala Pro Pro Ser
            35

<210> SEQ ID NO 122
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
```

-continued

```
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 122

Tyr Ala Glu Gly Thr Phe Thr Ser Asp Tyr Ser Ile Ala Leu Asp Lys
1               5                   10                  15

Xaa Ala Gln Lys Glu Phe Val Glu Trp Leu Leu Ala Gln Gly Pro Ser
            20                  25                  30

Ser Gly Ala Pro Pro Pro Ser
                35

<210> SEQ ID NO 123
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 123

Tyr Ala Glu Gly Thr Phe Thr Ser Asp Tyr Ser Ile Ala Leu Asp Lys
1               5                   10                  15

Xaa Ala Gln Lys Glu Phe Val Glu Trp Leu Leu Ala Ala Gly Pro Ser
            20                  25                  30

Ser Gly Ala Pro Pro Pro Ser
                35

<210> SEQ ID NO 124
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 124

Tyr Ala Glu Gly Thr Phe Thr Ser Asp Tyr Ser Ile Ala Leu Asp Lys
1               5                   10                  15

Xaa Ala Gln Arg Ala Phe Ile Glu Trp Leu Leu Ala Gln Gly Pro Ser
```

```
                    20                  25                  30

Ser Gly Ala Pro Pro Pro Ser
        35

<210> SEQ ID NO 125
<211> LENGTH: 38
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 125

Tyr Ala Glu Gly Thr Phe Thr Ser Asp Tyr Ser Ile Ala Leu Asp Lys
1               5                  10                  15

Xaa Ala Gln Arg Ala Phe Val Glu Trp Leu Leu Ala Gln Gly Pro Ser
            20                  25                  30

Ser Gly Ala Pro Pro Pro
        35

<210> SEQ ID NO 126
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 126

Tyr Ala Glu Gly Thr Phe Thr Ser Asp Leu Ser Ile Ala Leu Glu Lys
1               5                  10                  15

Xaa Ala Gln Arg Ala Phe Val Glu Trp Leu Leu Ala Gln Gly Pro Ser
            20                  25                  30

Ser Gly Ala Pro Pro Pro Ser
        35

<210> SEQ ID NO 127
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
```

-continued

```
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 127

Tyr Ala Glu Gly Thr Phe Thr Ser Asp Tyr Ser Ile Tyr Leu Asp Lys
1               5                   10                  15

Xaa Ala Gln Arg Ala Phe Val Glu Trp Leu Leu Ala Glu Gly Pro Ser
            20                  25                  30

Ser Gly Ala Pro Pro Pro Ser
        35

<210> SEQ ID NO 128
<211> LENGTH: 39
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 128

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Glu Gly Pro Ser
            20                  25                  30

Ser Gly Ala Pro Pro Pro Ser
        35

<210> SEQ ID NO 129
<211> LENGTH: 38
<212> TYPE: PRT
<213> ORGANISM: Artificial sequence
<220> FEATURE:
<223> OTHER INFORMATION: Synthetic construct: Peptide backbone of GIP
      analogue
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (17)..(17)
<223> OTHER INFORMATION: Xaa is Psi, wherein Psi is a residue of Lys,
      Arg, Orn or Cys in which the side chain is conjugated to a
      substituent having the formula -Z1 or -Z2-Z1, where Z1 and Z2 are
      as defined in PCT/EP2014/073970

<400> SEQUENCE: 129

Tyr Ala Glu Gly Thr Phe Thr Ser Asp Tyr Ser Ile Ala Leu Asp Lys
1               5                   10                  15

Xaa Ala Gln Arg Ala Phe Val Glu Trp Leu Leu Ala Glu Pro Ser Ser
            20                  25                  30

Gly Ala Pro Pro Pro Ser
```

```
<210> SEQ ID NO 130
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 130

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 131
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 131

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 132
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu)

<400> SEQUENCE: 132

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25
```

```
<210> SEQ ID NO 133
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-GSGSGG)

<400> SEQUENCE: 133

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 134
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-Peg3-Peg3)

<400> SEQUENCE: 134

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 135
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3-Peg3)

<400> SEQUENCE: 135

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 136
<211> LENGTH: 29
<212> TYPE: PRT
```

```
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-Dapa-Peg3-Peg3)

<400> SEQUENCE: 136

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 137
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3-
      Peg3)

<400> SEQUENCE: 137

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 138
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (2)..(2)
<223> OTHER INFORMATION: Xaa is DAla
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 138

Tyr Xaa Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 139
<211> LENGTH: 29
<212> TYPE: PRT
<213> ORGANISM: Artificial sequence
<220> FEATURE:
```

```
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 139

Tyr Ala Glu Gly Thr Phe Thr Ser Asp Tyr Ser Ile Tyr Leu Glu Lys
1               5                   10                  15

Lys Ala Ala Lys Glu Phe Val Glu Trp Leu Leu Ser Ala
            20                  25

<210> SEQ ID NO 140
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(13)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 140

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln
            20                  25

<210> SEQ ID NO 141
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 141

Tyr Ala Glu Gly Thr Phe Thr Ser Asp Tyr Ser Ile Tyr Leu Asp Lys
1               5                   10                  15

Lys Ala Gln Arg Ala Phe Val Asn Trp Leu Leu Ala Ala
            20                  25

<210> SEQ ID NO 142
<211> LENGTH: 29
<212> TYPE: PRT
<213> ORGANISM: Artificial sequence
<220> FEATURE:
<223> OTHER INFORMATION: Synthetic construct: Residues 1-29 of GIP
``` analogue of Formula I of PCT/EP2014/073970
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
    Peg3)

<400> SEQUENCE: 142

Tyr Ala Glu Gly Thr Phe Thr Ser Asp Tyr Ser Ile Ala Leu Asp Lys
1               5                   10                  15

Lys Ala Gln Arg Ala Phe Val Asn Trp Leu Val Ala Ala
            20                  25

<210> SEQ ID NO 143
<211> LENGTH: 29
<212> TYPE: PRT
<213> ORGANISM: Artificial sequence
<220> FEATURE:
<223> OTHER INFORMATION: Synthetic construct: Residues 1-29 of GIP
    analogue of Formula I of PCT/EP2014/073970
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 143

Tyr Ala Glu Gly Thr Phe Thr Ser Asp Tyr Ser Ile Ala Leu Asp Lys
1               5                   10                  15

Lys Ala Gln Arg Ala Phe Val Asn Trp Leu Val Ala Ala
            20                  25

<210> SEQ ID NO 144
<211> LENGTH: 29
<212> TYPE: PRT
<213> ORGANISM: Artificial sequence
<220> FEATURE:
<223> OTHER INFORMATION: Synthetic construct: Residues 1-29 of GIP
    analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
    Peg3)

<400> SEQUENCE: 144

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln
            20                  25

<210> SEQ ID NO 145
<211> LENGTH: 29
<212> TYPE: PRT
<213> ORGANISM: Artificial sequence
<220> FEATURE:
<223> OTHER INFORMATION: Synthetic construct: Residues 1-29 of GIP
    analogue of Formula I of PCT/EP2014/073970
<220> FEATURE:

```
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 145

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Leu Ala Gln
            20                  25

<210> SEQ ID NO 146
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 146

Tyr Ala Glu Gly Thr Phe Thr Ser Asp Leu Ser Ile Ala Leu Asp Lys
1               5                   10                  15

Lys Ala Gln Arg Ala Phe Val Asn Trp Leu Val Ala Ala
            20                  25

<210> SEQ ID NO 147
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(29)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 147

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Val Ala Ala
            20                  25

<210> SEQ ID NO 148
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
```

```
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 148

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Glu Ala Gln
            20                  25

<210> SEQ ID NO 149
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 149

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Glu Ala Gln
            20                  25

<210> SEQ ID NO 150
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 150

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln
            20                  25

<210> SEQ ID NO 151
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
```

```
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 151

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Glu Ala Gln
            20                  25

<210> SEQ ID NO 152
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 152

Tyr Ala Glu Gly Thr Phe Thr Ser Asp Leu Ser Ile Ala Leu Glu Lys
1               5                   10                  15

Lys Ala Gln Arg Ala Phe Val Glu Trp Leu Leu Ala Gln
            20                  25

<210> SEQ ID NO 153
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (2)..(2)
<223> OTHER INFORMATION: DAla
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 153

Tyr Xaa Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 154
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)
```

```
<400> SEQUENCE: 154

Tyr Ala Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln
            20                  25

<210> SEQ ID NO 155
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (2)..(2)
<223> OTHER INFORMATION: DAla
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 155

Tyr Xaa Glu Gly Thr Phe Thr Ser Asp Tyr Ser Ile Ala Leu Glu Lys
1               5                   10                  15

Lys Ala Gln Arg Ala Phe Val Glu Trp Leu Leu Ala Gln
            20                  25

<210> SEQ ID NO 156
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-Peg3-Peg3)
<220> FEATURE:
<221> NAME/KEY: SITE
<222> LOCATION: (29)..(29)
<223> OTHER INFORMATION: Linked to R2, wherein R2 is -NH2 or OH

<400> SEQUENCE: 156

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 157
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (1)..(1)
```

```
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu)
<220> FEATURE:
<221> NAME/KEY: SITE
<222> LOCATION: (29)..(29)
<223> OTHER INFORMATION: Linked to R2, wherein R2 is -NH2 or OH

<400> SEQUENCE: 157

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 158
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-Dapa-Peg3-Peg3)
<220> FEATURE:
<221> NAME/KEY: SITE
<222> LOCATION: (29)..(29)
<223> OTHER INFORMATION: Linked to R2, wherein R2 is -NH2 or OH

<400> SEQUENCE: 158

Tyr Ala Glu Gly Thr Phe Thr Ser Asp Tyr Ser Ile Tyr Leu Asp Lys
1               5                   10                  15

Lys Ala Gln Arg Ala Phe Val Glu Trp Leu Leu Ala Gln
            20                  25

<210> SEQ ID NO 159
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 159

Tyr Ala Glu Gly Thr Phe Thr Ser Asp Tyr Ser Ile Ala Leu Asp Lys
1               5                   10                  15
```

Lys Ala Gln Arg Ala Phe Val Glu Trp Leu Leu Ala Gln
            20                  25

<210> SEQ ID NO 160
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: SITE
<222> LOCATION: (2)..(2)
<223> OTHER INFORMATION: DAla
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 160

Tyr Xaa Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln
            20                  25

<210> SEQ ID NO 161
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 161

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Ala
            20                  25

<210> SEQ ID NO 162
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 162

Tyr Ala Glu Gly Thr Phe Thr Ser Asp Tyr Ser Ile Ala Leu Asp Lys
1               5                   10                  15

Lys Ala Ala Lys Glu Phe Val Glu Trp Leu Leu Ser Ala
            20                  25

<210> SEQ ID NO 163
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 163

Tyr Ala Glu Gly Thr Phe Thr Ser Asp Tyr Ser Ile Ala Leu Asp Glu
1               5                   10                  15
Lys Ala Gln Arg Ala Phe Val Glu Trp Leu Leu Ala Gln
            20                  25

<210> SEQ ID NO 164
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 164

Tyr Ala Glu Gly Thr Phe Thr Ser Asp Tyr Ser Ile Ala Leu Asp Glu
1               5                   10                  15
Lys Ala Gln Arg Ala Phe Val Glu Trp Leu Leu Ala Ala
            20                  25

<210> SEQ ID NO 165
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 165

Tyr Ala Glu Gly Thr Phe Thr Ser Asp Tyr Ser Ile Ala Leu Asp Lys
1               5                   10                  15
Lys Ala Gln Lys Ala Phe Val Glu Trp Leu Leu Ala Ala
            20                  25

<210> SEQ ID NO 166
<211> LENGTH: 29
<212> TYPE: PRT
<213> ORGANISM: Artificial sequence

```
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 166

Tyr Ala Glu Gly Thr Phe Thr Ser Asp Tyr Ser Ile Tyr Leu Asp Lys
1               5                   10                  15

Lys Ala Gln Arg Glu Phe Val Glu Trp Leu Leu Ala Gln
            20                  25

<210> SEQ ID NO 167
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 167

Tyr Ala Glu Gly Thr Phe Thr Ser Asp Tyr Ser Ile Ala Leu Asp Lys
1               5                   10                  15

Lys Ala Gln Arg Glu Phe Val Glu Trp Leu Leu Ala Gln
            20                  25

<210> SEQ ID NO 168
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 168

Tyr Ala Glu Gly Thr Phe Thr Ser Asp Tyr Ser Ile Ala Leu Asp Lys
1               5                   10                  15

Lys Ala Gln Lys Glu Phe Val Glu Trp Leu Leu Ala Gln
            20                  25

<210> SEQ ID NO 169
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
```

```
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 169

Tyr Ala Glu Gly Thr Phe Thr Ser Asp Tyr Ser Ile Ala Leu Asp Lys
1               5                   10                  15

Lys Ala Gln Lys Glu Phe Val Glu Trp Leu Leu Ala Ala
            20                  25

<210> SEQ ID NO 170
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([19-Carboxy-nonadecanoyl]-isoGlu-Peg3-Peg3)

<400> SEQUENCE: 170

Tyr Ala Glu Gly Thr Phe Thr Ser Asp Tyr Ser Ile Ala Leu Asp Lys
1               5                   10                  15

Lys Ala Gln Arg Ala Phe Ile Glu Trp Leu Leu Ala Gln
            20                  25

<210> SEQ ID NO 171
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys([17-carboxy-heptadecanoyl]-isoGlu-Peg3-
      Peg3)

<400> SEQUENCE: 171

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln
            20                  25

<210> SEQ ID NO 172
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
```

```
<220> FEATURE:
<221> NAME/KEY: SITE
<222> LOCATION: (17)..(17)
<223> OTHER INFORMATION: Lys((19-Carboxy-nonadecanoyl)-[(Piperazine-1-
      yl)-acetyl]-Peg3-Peg3)

<400> SEQUENCE: 172

Tyr Ala Glu Gly Thr Phe Thr Ser Asp Tyr Ser Ile Ala Leu Asp Lys
1               5                   10                  15

Lys Ala Gln Arg Ala Phe Val Glu Trp Leu Leu Ala Gln
            20                  25

<210> SEQ ID NO 173
<211> LENGTH: 29
<212> TYPE: PRT
<213> ORGANISM: Artificial sequence
<220> FEATURE:
<223> OTHER INFORMATION: Synthetic construct: Residues 1-29 of GIP
      analogue of Formula I of PCT/EP2014/073970
<220> FEATURE:
<221> NAME/KEY: MOD_RES
<222> LOCATION: (2)..(2)
<223> OTHER INFORMATION: Aib
<220> FEATURE:
<221> NAME/KEY: SITE
<222> LOCATION: (17)..(17)
<223> OTHER INFORMATION: Lys((19-Carboxy-nonadecanoyl)-[(Piperazine-1-
      yl)-acetyl]-Peg3)

<400> SEQUENCE: 173

Tyr Ala Glu Gly Thr Phe Thr Ser Asp Tyr Ser Ile Ala Leu Asp Lys
1               5                   10                  15

Lys Ala Gln Lys Glu Phe Val Glu Trp Leu Leu Ala Ala
            20                  25

<210> SEQ ID NO 174
<211> LENGTH: 466
<212> TYPE: PRT
<213> ORGANISM: Homo sapiens

<400> SEQUENCE: 174

Met Thr Thr Ser Pro Ile Leu Gln Leu Leu Leu Arg Leu Ser Leu Cys
1               5                   10                  15

Gly Leu Leu Leu Gln Arg Ala Glu Thr Gly Ser Lys Gly Gln Thr Ala
            20                  25                  30

Gly Glu Leu Tyr Gln Arg Trp Glu Arg Tyr Arg Arg Glu Cys Gln Glu
        35                  40                  45

Thr Leu Ala Ala Ala Glu Pro Pro Ser Gly Leu Ala Cys Asn Gly Ser
    50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
    130                 135                 140

Tyr Ser Leu Ser Leu Ala Thr Leu Leu Ala Leu Leu Ile Leu Ser
145                 150                 155                 160

Leu Phe Arg Arg Leu His Cys Thr Arg Asn Tyr Ile His Ile Asn Leu
```

165                 170                 175
Phe Thr Ser Phe Met Leu Arg Ala Ala Ala Ile Leu Ser Arg Asp Arg
                180                 185                 190

Leu Leu Pro Arg Pro Gly Pro Tyr Leu Gly Asp Gln Ala Leu Ala Leu
            195                 200                 205

Trp Asn Gln Ala Leu Ala Ala Cys Arg Thr Ala Gln Ile Val Thr Gln
    210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
            260                 265                 270

Pro Trp Val Ile Val Arg Tyr Leu Tyr Glu Asn Thr Gln Cys Trp Glu
        275                 280                 285

Arg Asn Glu Val Lys Ala Ile Trp Trp Ile Ile Arg Thr Pro Ile Leu
    290                 295                 300

Met Thr Ile Leu Ile Asn Phe Leu Ile Phe Ile Arg Ile Leu Gly Ile
305                 310                 315                 320

Leu Leu Ser Lys Leu Arg Thr Arg Gln Met Arg Cys Arg Asp Tyr Arg
                325                 330                 335

Leu Arg Leu Ala Arg Ser Thr Leu Thr Leu Val Pro Leu Leu Gly Val
            340                 345                 350

His Glu Val Val Phe Ala Pro Val Thr Glu Glu Gln Ala Arg Gly Ala
        355                 360                 365

Leu Arg Phe Ala Lys Leu Gly Phe Glu Ile Phe Leu Ser Ser Phe Gln
    370                 375                 380

Gly Phe Leu Val Ser Val Leu Tyr Cys Phe Ile Asn Lys Glu Val Gln
385                 390                 395                 400

Ser Glu Ile Arg Arg Gly Trp His His Cys Arg Leu Arg Arg Ser Leu
                405                 410                 415

Gly Glu Glu Gln Arg Gln Leu Pro Glu Arg Ala Phe Arg Ala Leu Pro
            420                 425                 430

Ser Gly Ser Gly Pro Gly Glu Val Pro Thr Ser Arg Gly Leu Ser Ser
        435                 440                 445

Gly Thr Leu Pro Gly Pro Gly Asn Glu Ala Ser Arg Glu Leu Glu Ser
    450                 455                 460

Tyr Cys
465

<210> SEQ ID NO 175
<211> LENGTH: 463
<212> TYPE: PRT
<213> ORGANISM: Homo sapiens

<400> SEQUENCE: 175

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Pro Ala Thr Asp Leu Phe Cys Asn Arg
    50                  55                  60

```
Thr Phe Asp Glu Tyr Ala Cys Trp Pro Asp Gly Glu Pro Gly Ser Phe
 65                  70                  75                  80

Val Asn Val Ser Cys Pro Trp Tyr Leu Pro Trp Ala Ser Ser Val Pro
                 85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Leu Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
    290                 295                 300

Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
        355                 360                 365

Phe Val Met Asp Glu His Ala Arg Gly Thr Leu Arg Phe Ile Lys Leu
    370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
        435                 440                 445

Ala Gly Ser Ser Met Tyr Thr Ala Thr Cys Gln Ala Ser Cys Ser
    450                 455                 460

<210> SEQ ID NO 176
<211> LENGTH: 6
<212> TYPE: PRT
```

```
<213> ORGANISM: Artificial sequence
<220> FEATURE:
<223> OTHER INFORMATION: Synthetic linker

<400> SEQUENCE: 176

Gly Ser Gly Ser Gly Gly
1               5

<210> SEQ ID NO 177
<211> LENGTH: 40
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (3)..(3)
<223> OTHER INFORMATION: Aib
<220> FEATURE:
<221> NAME/KEY: SITE
<222> LOCATION: (18)..(18)
<223> OTHER INFORMATION: Lys([17-carboxy-heptadecanoyl]-isoGlu-GSGSGG)

<400> SEQUENCE: 177

His Tyr Ala Glu Gly Thr Phe Thr Ser Asp Tyr Ser Ile Tyr Leu Asp
1               5                   10                  15

Lys Lys Ala Gln Arg Ala Phe Val Glu Trp Leu Leu Ala Gln Gly Pro
            20                  25                  30

Ser Ser Gly Ala Pro Pro Pro Ser
        35                  40

<210> SEQ ID NO 178
<211> LENGTH: 40
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (3)..(3)
<223> OTHER INFORMATION: Aib
<220> FEATURE:
<221> NAME/KEY: SITE
<222> LOCATION: (18)..(18)
<223> OTHER INFORMATION: Lys([17-carboxy-heptadecanoyl]-isoGlu-Peg3-
      Peg3-Peg3)

<400> SEQUENCE: 178

His Tyr Ala Glu Gly Thr Phe Thr Ser Asp Tyr Ser Ile Tyr Leu Asp
1               5                   10                  15

Lys Lys Ala Gln Arg Ala Phe Val Glu Trp Leu Leu Ala Gln Gly Pro
            20                  25                  30

Ser Ser Gly Ala Pro Pro Pro Ser
        35                  40

<210> SEQ ID NO 179
<211> LENGTH: 30
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (3)..(3)
<223> OTHER INFORMATION: Aib
<220> FEATURE:
<221> NAME/KEY: SITE
<222> LOCATION: (18)..(18)
<223> OTHER INFORMATION: Lys([17-carboxy-heptadecanoyl]-isoGlu-GSGSGG)
```

```
<400> SEQUENCE: 179

His Tyr Ala Glu Gly Thr Phe Thr Ser Asp Tyr Ser Ile Tyr Leu Asp
1               5                   10                  15

Lys Lys Ala Gln Arg Ala Phe Val Glu Trp Leu Leu Ala Gln
            20                  25                  30

<210> SEQ ID NO 180
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 180

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
            35                  40

<210> SEQ ID NO 181
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-Carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 181

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
            35                  40

<210> SEQ ID NO 182
<211> LENGTH: 41
<212> TYPE: PRT
<213> ORGANISM: Artificial Sequence
<220> FEATURE:
```

```
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu)
<220> FEATURE:
<221> NAME/KEY: MISC_FEATURE
<222> LOCATION: (41)..(41)
<223> OTHER INFORMATION: Xaa is NH2

<400> SEQUENCE: 182

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 183
<211> LENGTH: 42
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Aib
<220> FEATURE:
<221> NAME/KEY: MISC_FEATURE
<222> LOCATION: (19)..(19)
<223> OTHER INFORMATION: Xaa is Lys([17-carboxy-heptadecanoyl]-isoGlu-
      GSGSGG)
<220> FEATURE:
<221> NAME/KEY: MISC_FEATURE
<222> LOCATION: (42)..(42)
<223> OTHER INFORMATION: Xaa is NH2

<400> SEQUENCE: 183

His His Tyr Xaa Glu Gly Thr Phe Thr Ser Asp Tyr Ser Ile Tyr Leu
1               5                   10                  15

Asp Lys Xaa Ala Gln Arg Ala Phe Val Glu Trp Leu Leu Ala Gln Gly
            20                  25                  30

Pro Ser Ser Gly Ala Pro Pro Pro Ser Xaa
        35                  40

<210> SEQ ID NO 184
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-Peg3-
      Peg3)
<220> FEATURE:
<221> NAME/KEY: MISC_FEATURE
<222> LOCATION: (41)..(41)
<223> OTHER INFORMATION: Xaa is NH2

<400> SEQUENCE: 184
```

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 185
<211> LENGTH: 42
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Aib
<220> FEATURE:
<221> NAME/KEY: MISC_FEATURE
<222> LOCATION: (19)..(19)
<223> OTHER INFORMATION: Xaa is Lys([17-carboxy-heptadecanoyl]-isoGlu-
      Peg3-Peg3-Peg3)
<220> FEATURE:
<221> NAME/KEY: MISC_FEATURE
<222> LOCATION: (42)..(42)
<223> OTHER INFORMATION: Xaa is NH2

<400> SEQUENCE: 185

His His Tyr Xaa Glu Gly Thr Phe Thr Ser Asp Tyr Ser Ile Tyr Leu
1               5                   10                  15

Asp Lys Xaa Ala Gln Arg Ala Phe Val Glu Trp Leu Leu Ala Gln Gly
            20                  25                  30

Pro Ser Ser Gly Ala Pro Pro Pro Ser Xaa
        35                  40

<210> SEQ ID NO 186
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-Dapa-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 186

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 187
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-Carboxy-nonadecanoyl]-isoGlu-
      Peg3-Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 187

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 188
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is DAla
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 188

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 189
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 189

His Tyr Xaa Glu Gly Thr Phe Thr Ser Asp Tyr Ser Ile Tyr Leu Glu
1               5                   10                  15

Lys Xaa Ala Ala Lys Glu Phe Val Glu Trp Leu Leu Ser Ala Gly Pro
            20                  25                  30

Ser Ser Gly Ala Pro Pro Pro Ser Xaa
        35                  40

<210> SEQ ID NO 190
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (14)..(14)
<223> OTHER INFORMATION: Xaa is Aib
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (39)..(39)
<223> OTHER INFORMATION: Xaa is NH2

<400> SEQUENCE: 190

His Tyr Xaa Glu Gly Thr Phe Thr Ser Asp Tyr Ser Ile Xaa Xaa Xaa
1               5                   10                  15

Ala Gln Arg Ala Phe Val Glu Trp Leu Leu Ala Gln Gly Pro Ser Ser
            20                  25                  30

Gly Ala Pro Pro Pro Ser Xaa
        35

<210> SEQ ID NO 191
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (30)..(30)
<223> OTHER INFORMATION: Xaa is Aib
<220> FEATURE:
<221> NAME/KEY: MISC_FEATURE
<222> LOCATION: (32)..(23)
<223> OTHER INFORMATION: Xaa is NH2
<220> FEATURE:
<221> NAME/KEY: misc_feature
<222> LOCATION: (32)..(32)

<223> OTHER INFORMATION: Xaa can be any naturally occurring amino acid

<400> SEQUENCE: 191

His Tyr Xaa Glu Gly Thr Phe Thr Ser Asp Tyr Ser Ile Tyr Leu Asp
1               5                   10                  15

Lys Xaa Ala Gln Arg Ala Phe Val Asn Trp Leu Leu Ala Xaa Lys Xaa
            20                  25                  30

<210> SEQ ID NO 192
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (31)..(31)
<223> OTHER INFORMATION: Xaa is NH2

<400> SEQUENCE: 192

His Tyr Xaa Glu Gly Thr Phe Thr Ser Asp Tyr Ser Ile Tyr Leu Asp
1               5                   10                  15

Glu Xaa Ala Ala Lys Glu Phe Ile Glu Trp Leu Glu Ser Ala Xaa
            20                  25                  30

<210> SEQ ID NO 193
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (30)..(30)
<223> OTHER INFORMATION: Xaa is Aib
<220> FEATURE:
<221> NAME/KEY: MISC_FEATURE
<222> LOCATION: (41)..(41)
<223> OTHER INFORMATION: Xaa is NH2

<400> SEQUENCE: 193

His Tyr Xaa Glu Gly Thr Phe Thr Ser Asp Tyr Ser Ile Ala Leu Asp
1               5                   10                  15

Lys Xaa Ala Gln Arg Ala Phe Val Asn Trp Leu Val Ala Xaa Lys Pro
            20                  25                  30

Ser Ser Gly Ala Pro Pro Pro Ser Xaa
            35                  40

<210> SEQ ID NO 194
<211> LENGTH: 41
<212> TYPE: PRT

```
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys[19-carboxy-nonadecanoyl]-isoGlu-
     Peg3-Peg3)
<220> FEATURE:
<221> NAME/KEY: MISC_FEATURE
<222> LOCATION: (30)..(30)
<223> OTHER INFORMATION: Xaa is Aib
<220> FEATURE:
<221> NAME/KEY: MISC_FEATURE
<222> LOCATION: (41)..(41)
<223> OTHER INFORMATION: Xaa is NH2

<400> SEQUENCE: 194

His Tyr Xaa Glu Gly Thr Phe Thr Ser Asp Tyr Ser Ile Ala Leu Asp
1               5                   10                  15

Lys Xaa Ala Gln Arg Ala Phe Val Asn Trp Leu Val Ala Xaa Lys Pro
            20                  25                  30

Ser Ser Gly Ala Pro Pro Pro Ser Xaa
            35                  40

<210> SEQ ID NO 195
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
     Peg3-Peg3)
<220> FEATURE:
<221> NAME/KEY: MISC_FEATURE
<222> LOCATION: (32)..(32)
<223> OTHER INFORMATION: Xaa is NH2

<400> SEQUENCE: 195

His Tyr Xaa Glu Gly Thr Phe Thr Ser Asp Tyr Ser Ile Ala Leu Glu
1               5                   10                  15

Lys Xaa Ala Gln Arg Ala Phe Val Glu Trp Leu Leu Ala Gln Lys Xaa
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
     Peg3-Peg3)
<220> FEATURE:
<221> NAME/KEY: MISC_FEATURE
```

```
<222> LOCATION: (32)..(32)
<223> OTHER INFORMATION: Xaa is NH2

<400> SEQUENCE: 196

His Tyr Xaa Glu Gly Thr Phe Thr Ser Asp Leu Ser Ile Ala Leu Glu
1               5                   10                  15

Lys Xaa Ala Gln Arg Ala Phe Val Glu Trp Leu Leu Ala Gln Lys Xaa
            20                  25                  30

<210> SEQ ID NO 197
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (31)..(31)
<223> OTHER INFORMATION: Xaa is NH2

<400> SEQUENCE: 197

His Tyr Xaa Glu Gly Thr Phe Thr Ser Asp Tyr Ser Ile Tyr Leu Glu
1               5                   10                  15

Lys Xaa Ala Gln Arg Ala Phe Val Glu Trp Leu Leu Arg Ala Xaa
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
      Peg3-Peg3)
<220> FEATURE:
<221> NAME/KEY: MISC_FEATURE
<222> LOCATION: (30)..(30)
<223> OTHER INFORMATION: Xaa is Aib
<220> FEATURE:
<221> NAME/KEY: MISC_FEATURE
<222> LOCATION: (32)..(32)
<223> OTHER INFORMATION: Xaa is NH2

<400> SEQUENCE: 198

His Tyr Xaa Glu Gly Thr Phe Thr Ser Asp Tyr Ser Ile Ala Leu Asp
1               5                   10                  15

Lys Xaa Ala Gln Arg Ala Phe Val Asn Trp Leu Val Ala Xaa Lys Xaa
            20                  25                  30

<210> SEQ ID NO 199
<211> LENGTH: 32
<212> TYPE: PRT
<213> ORGANISM: Artificial Sequence
<220> FEATURE:
```

<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
    Peg3-Peg3)
<220> FEATURE:
<221> NAME/KEY: MISC_FEATURE
<222> LOCATION: (30)..(30)
<223> OTHER INFORMATION: Xaa is Aib
<220> FEATURE:
<221> NAME/KEY: MISC_FEATURE
<222> LOCATION: (32)..(32)
<223> OTHER INFORMATION: Xaa is NH2

<400> SEQUENCE: 199

His Tyr Xaa Glu Gly Thr Phe Thr Ser Asp Leu Ser Ile Ala Leu Asp
1               5                   10                  15

Lys Xaa Ala Gln Arg Ala Phe Val Asn Trp Leu Val Ala Xaa Lys Xaa
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is K([17-carboxy-heptadecanoyl]-isoGlu-
    Peg3-Peg3)
<220> FEATURE:
<221> NAME/KEY: MISC_FEATURE
<222> LOCATION: (30)..(30)
<223> OTHER INFORMATION: Xaa is Aib
<220> FEATURE:
<221> NAME/KEY: MISC_FEATURE
<222> LOCATION: (32)..(32)
<223> OTHER INFORMATION: Xaa is NH2

<400> SEQUENCE: 200

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Val Ala Xaa Lys Xaa
            20                  25                  30

<210> SEQ ID NO 201
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
    Peg3-Peg3)
<220> FEATURE:
<221> NAME/KEY: MISC_FEATURE
<222> LOCATION: (41)..(41)

<223> OTHER INFORMATION: Xaa is NH2

<400> SEQUENCE: 201

His Tyr Xaa Glu Gly Thr Phe Thr Ser Asp Tyr Ser Ile Ala Leu Glu
1               5                   10                  15

Lys Xaa Ala Gln Arg Ala Phe Val Glu Trp Leu Glu Ala Gln Gly Pro
            20                  25                  30

Ser Ser Gly Ala Pro Pro Pro Ser Xaa
        35                  40

<210> SEQ ID NO 202
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
    Peg3-Peg3)
<220> FEATURE:
<221> NAME/KEY: MISC_FEATURE
<222> LOCATION: (32)..(32)
<223> OTHER INFORMATION: Xaa is NH2

<400> SEQUENCE: 202

His Tyr Xaa Glu Gly Thr Phe Thr Ser Asp Tyr Ser Ile Ala Leu Glu
1               5                   10                  15

Lys Xaa Ala Gln Arg Ala Phe Val Glu Trp Leu Glu Ala Gln Lys Xaa
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
    Peg3-Peg3)
<220> FEATURE:
<221> NAME/KEY: MISC_FEATURE
<222> LOCATION: (32)..(32)
<223> OTHER INFORMATION: Xaa is NH2

<400> SEQUENCE: 203

His Tyr Xaa Glu Gly Thr Phe Thr Ser Asp Leu Ser Ile Ala Leu Glu
1               5                   10                  15

Lys Xaa Ala Gln Arg Ala Phe Val Glu Trp Leu Glu Ala Gln Lys Xaa
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: Synthetic construct
<220> FEATURE:

```
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys[19-carboxy-nonadecanoyl]-isoGlu-
      Peg3-Peg3)
<220> FEATURE:
<221> NAME/KEY: MISC_FEATURE
<222> LOCATION: (32)..(32)
<223> OTHER INFORMATION: Xaa is NH2
<220> FEATURE:
<221> NAME/KEY: MISC_FEATURE
<222> LOCATION: (32)..(32)
<223> OTHER INFORMATION: Xaa is NH2

<400> SEQUENCE: 204

His Tyr Xaa Glu Gly Thr Phe Thr Ser Asp Tyr Ser Ile Ala Leu Glu
1               5                   10                  15

Lys Xaa Ala Gln Arg Ala Phe Val Glu Trp Leu Leu Ala Gln Lys Xaa
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys[19-carboxy-nonadecanoyl]-isoGlu-
      Peg3-Peg3)
<220> FEATURE:
<221> NAME/KEY: MISC_FEATURE
<222> LOCATION: (32)..(32)
<223> OTHER INFORMATION: Xaa is NH2

<400> SEQUENCE: 205

His Tyr Xaa Glu Gly Thr Phe Thr Ser Asp Leu Ser Ile Ala Leu Glu
1               5                   10                  15

Lys Xaa Ala Gln Arg Ala Phe Val Glu Trp Leu Glu Ala Gln Lys Xaa
            20                  25                  30

<210> SEQ ID NO 206
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (32)..(32)
<223> OTHER INFORMATION: Xaa is NH2

<400> SEQUENCE: 206

His Tyr Xaa Glu Gly Thr Phe Thr Ser Asp Leu Ser Ile Ala Leu Glu
1               5                   10                  15
```

```
Lys Xaa Ala Gln Arg Ala Phe Val Glu Trp Leu Leu Ala Gln Lys Xaa
            20                  25                  30

<210> SEQ ID NO 207
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (31)..(31)
<223> OTHER INFORMATION: Xaa is NH2

<400> SEQUENCE: 207

His Tyr Xaa Glu Gly Thr Phe Thr Ser Asp Tyr Ser Ile Tyr Leu Glu
1               5                   10                  15

Lys Xaa Ala Gln Arg Ala Phe Val Glu Trp Leu Leu Arg Ala Xaa
            20                  25                  30

<210> SEQ ID NO 208
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is DAla
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 208

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
            35                  40

<210> SEQ ID NO 209
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
```

<223> OTHER INFORMATION: Xaa is Lys([19-carboxy-nonadecanoyl]-isoGlu-
    Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 209

His Tyr Xaa Glu Gly Thr Phe Thr Ser Asp Tyr Ser Ile Ala Leu Glu
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 210
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
    Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 210

His Tyr Xaa Glu Gly Thr Phe Thr Ser Asp Tyr Ser Ile Ala Leu Glu
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 211
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
    Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 211

His Tyr Xaa Glu Gly Thr Phe Thr Ser Asp Leu Ser Ile Ala Leu Glu
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
            35                  40

<210> SEQ ID NO 212
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 212

His Tyr Xaa Glu Gly Thr Phe Thr Ser Asp Leu Ser Ile Ala Leu Glu
1               5                   10                  15

Lys Xaa Ala Gln Arg Ala Phe Val Glu Trp Leu Leu Ala Gln Lys Pro
            20                  25                  30

Ser Ser Gly Ala Pro Pro Pro Ser Xaa
            35                  40

<210> SEQ ID NO 213
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 213

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
            35                  40

<210> SEQ ID NO 214
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-IsoGlu)
<220> FEATURE:
<221> NAME/KEY: MISC_FEATURE
<222> LOCATION: (41)..(41)
<223> OTHER INFORMATION: Xaa is NH2

<400> SEQUENCE: 214

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 215
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-Dapa-Peg3-
      Peg3)
<220> FEATURE:
<221> NAME/KEY: MISC_FEATURE
<222> LOCATION: (41)..(41)
<223> OTHER INFORMATION: Xaa is NH2

<400> SEQUENCE: 215

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 216
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 216

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Gln Lys Pro
            20                  25                  30

Ser Ser Gly Ala Pro Pro Pro Ser Xaa
        35                  40

<210> SEQ ID NO 217
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 217

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Gln Lys Pro
            20                  25                  30

Ser Ser Gly Ala Pro Pro Pro Ser Xaa
        35                  40

<210> SEQ ID NO 218
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (40)..(40)
<223> OTHER INFORMATION: Xaa is NH2

<400> SEQUENCE: 218

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Ala Pro Ser
            20                  25                  30

Ser Gly Ala Pro Pro Pro Ser Xaa
        35                  40

<210> SEQ ID NO 219
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:

```
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 219

His Tyr Xaa Glu Gly Thr Phe Thr Ser Asp Tyr Ser Ile Ala Leu Asp
1               5                   10                  15

Lys Xaa Ala Ala Lys Glu Phe Val Glu Trp Leu Leu Ser Ala Gly Pro
            20                  25                  30

Ser Ser Gly Ala Pro Pro Pro Ser Xaa
            35                  40

<210> SEQ ID NO 220
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 220

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
            35                  40

<210> SEQ ID NO 221
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 221

His Tyr Xaa Glu Gly Thr Phe Thr Ser Asp Tyr Ser Ile Ala Leu Asp
1               5                   10                  15

Glu Xaa Ala Gln Arg Ala Phe Val Glu Trp Leu Leu Ala Gln Gly Pro
```

```
                20                  25                  30

Ser Ser Gly Ala Pro Pro Ser Xaa
        35                  40

<210> SEQ ID NO 222
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 222

His Tyr Xaa Glu Gly Thr Phe Thr Ser Asp Tyr Ser Ile Ala Leu Asp
1               5                   10                  15

Glu Xaa Ala Gln Arg Ala Phe Val Glu Trp Leu Leu Ala Ala Gly Pro
                20                  25                  30

Ser Ser Gly Ala Pro Pro Ser Xaa
        35                  40

<210> SEQ ID NO 223
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 223

His Tyr Xaa Glu Gly Thr Phe Thr Ser Asp Tyr Ser Ile Ala Leu Asp
1               5                   10                  15

Lys Xaa Ala Gln Lys Ala Phe Val Glu Trp Leu Leu Ala Ala Gly Pro
                20                  25                  30

Ser Ser Gly Ala Pro Pro Ser Xaa
        35                  40

<210> SEQ ID NO 224
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
```

```
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 224

His Tyr Xaa Glu Gly Thr Phe Thr Ser Asp Tyr Ser Ile Tyr Leu Asp
1               5                   10                  15

Lys Xaa Ala Gln Arg Glu Phe Val Glu Trp Leu Leu Ala Gln Gly Pro
            20                  25                  30

Ser Ser Gly Ala Pro Pro Pro Ser Xaa
        35                  40

<210> SEQ ID NO 225
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 225

His Tyr Xaa Glu Gly Thr Phe Thr Ser Asp Tyr Ser Ile Ala Leu Asp
1               5                   10                  15

Lys Xaa Ala Gln Arg Glu Phe Val Glu Trp Leu Leu Ala Gln Gly Pro
            20                  25                  30

Ser Ser Gly Ala Pro Pro Pro Ser Xaa
        35                  40

<210> SEQ ID NO 226
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 226

His Tyr Xaa Glu Gly Thr Phe Thr Ser Asp Tyr Ser Ile Ala Leu Asp
1               5                   10                  15
```

Lys Xaa Ala Gln Lys Glu Phe Val Glu Trp Leu Leu Ala Gln Gly Pro
            20                  25                  30

Ser Ser Gly Ala Pro Pro Pro Ser Xaa
            35                  40

<210> SEQ ID NO 227
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 227

His Tyr Xaa Glu Gly Thr Phe Thr Ser Asp Tyr Ser Ile Ala Leu Asp
1               5                   10                  15

Lys Xaa Ala Gln Lys Glu Phe Val Glu Trp Leu Leu Ala Ala Gly Pro
            20                  25                  30

Ser Ser Gly Ala Pro Pro Pro Ser Xaa
            35                  40

<210> SEQ ID NO 228
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 228

His Tyr Xaa Glu Gly Thr Phe Thr Ser Asp Tyr Ser Ile Ala Leu Asp
1               5                   10                  15

Lys Xaa Ala Gln Arg Ala Phe Ile Glu Trp Leu Leu Ala Gln Gly Pro
            20                  25                  30

Ser Ser Gly Ala Pro Pro Pro Ser Xaa
            35                  40

<210> SEQ ID NO 229
<211> LENGTH: 41
<212> TYPE: PRT
<213> ORGANISM: Artificial Sequence
<220> FEATURE:
<223> OTHER INFORMATION: Synthetic construct
<220> FEATURE:

<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([17-carboxy-heptadecanoyl]-isoGlu-
    Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 229

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 230
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys((19-Carboxy-nonadecanoyl)-
    [(Piperazine-1-yl)-acetyl]-Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 230

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Gln Gly Pro
            20                  25                  30

Ser Ser Gly Ala Pro Pro Pro Ser Xaa
        35                  40

<210> SEQ ID NO 231
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys((19-Carboxy-nonadecanoyl)-
    [(Piperazine-1-yl)-acetyl]-Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 231

-continued

```
His Tyr Xaa Glu Gly Thr Phe Thr Ser Asp Tyr Ser Ile Ala Leu Asp
1               5                   10                  15

Lys Xaa Ala Gln Lys Glu Phe Val Glu Trp Leu Leu Ala Ala Gly Pro
            20                  25                  30

Ser Ser Gly Ala Pro Pro Pro Ser Xaa
        35                  40

<210> SEQ ID NO 232
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-Carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 232

His Tyr Xaa Glu Gly Thr Phe Thr Ser Asp Tyr Ser Ile Tyr Leu Asp
1               5                   10                  15

Lys Xaa Ala Gln Arg Ala Phe Val Glu Trp Leu Leu Ala Glu Gly Pro
            20                  25                  30

Ser Ser Gly Ala Pro Pro Pro Ser Xaa
        35                  40

<210> SEQ ID NO 233
<211> LENGTH: 41
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (41)..(41)
<223> OTHER INFORMATION: Xaa is NH2

<400> SEQUENCE: 233

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Glu Gly Pro
            20                  25                  30

Ser Ser Gly Ala Pro Pro Pro Ser Xaa
        35                  40

<210> SEQ ID NO 234
<211> LENGTH: 40
<212> TYPE: PRT
<213> ORGANISM: Artificial Sequence
<220> FEATURE:
```

```
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (18)..(18)
<223> OTHER INFORMATION: Xaa is Lys([19-carboxy-nonadecanoyl]-isoGlu-
      Peg3-Peg3)
<220> FEATURE:
<221> NAME/KEY: MISC_FEATURE
<222> LOCATION: (40)..(40)
<223> OTHER INFORMATION: Xaa is NH2

<400> SEQUENCE: 234

His Tyr Xaa Glu Gly Thr Phe Thr Ser Asp Tyr Ser Ile Ala Leu Asp
1               5                   10                  15

Lys Xaa Ala Gln Arg Ala Phe Val Glu Trp Leu Leu Ala Glu Pro Ser
            20                  25                  30

Ser Gly Ala Pro Pro Pro Ser Xaa
        35                  40

<210> SEQ ID NO 235
<211> LENGTH: 466
<212> TYPE: PRT
<213> ORGANISM: Homo sapiens

<400> SEQUENCE: 235

Met Thr Thr Ser Pro Ile Leu Gln Leu Leu Arg Leu Ser Leu Cys
1               5                   10                  15

Gly Leu Leu Leu Gln Arg Ala Glu Thr Gly Ser Lys Gly Gln Thr Ala
            20                  25                  30

Gly Glu Leu Tyr Gln Arg Trp Glu Arg Tyr Arg Arg Glu Cys Gln Glu
        35                  40                  45

Thr Leu Ala Ala Ala Glu Pro Pro Ser Gly Leu Ala Cys Asn Gly Ser
    50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
    130                 135                 140

Tyr Ser Leu Ser Leu Ala Thr Leu Leu Leu Ala Leu Leu Ile Leu Ser
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
            180                 185                 190

Leu Leu Pro Arg Pro Gly Pro Tyr Leu Gly Asp Gln Ala Leu Ala Leu
        195                 200                 205

Trp Asn Gln Ala Leu Ala Ala Cys Arg Thr Ala Gln Ile Val Thr Gln
    210                 215                 220

Tyr Cys Val Gly Ala Asn Tyr Thr Trp Leu Leu Val Glu Gly Val Tyr
225                 230                 235                 240
```

```
Leu His Ser Leu Leu Val Leu Val Gly Gly Ser Glu Glu Gly His Phe
                245                 250                 255

Arg Tyr Tyr Leu Leu Gly Trp Gly Ala Pro Ala Leu Phe Val Ile
        260                 265                 270

Pro Trp Val Ile Val Arg Tyr Leu Tyr Glu Asn Thr Gln Cys Trp Glu
            275                 280                 285

Arg Asn Glu Val Lys Ala Ile Trp Trp Ile Arg Thr Pro Ile Leu
        290                 295                 300

Met Thr Ile Leu Ile Asn Phe Leu Ile Phe Ile Arg Ile Leu Gly Ile
305                 310                 315                 320

Leu Leu Ser Lys Leu Arg Thr Arg Gln Met Arg Cys Arg Asp Tyr Arg
                325                 330                 335

Leu Arg Leu Ala Arg Ser Thr Leu Thr Leu Val Pro Leu Leu Gly Val
            340                 345                 350

His Glu Val Val Phe Ala Pro Val Thr Glu Glu Gln Ala Arg Gly Ala
        355                 360                 365

Leu Arg Phe Ala Lys Leu Gly Phe Glu Ile Phe Leu Ser Ser Phe Gln
    370                 375                 380

Gly Phe Leu Val Ser Val Leu Tyr Cys Phe Ile Asn Lys Glu Val Gln
385                 390                 395                 400

Ser Glu Ile Arg Arg Gly Trp His His Cys Arg Leu Arg Arg Ser Leu
                405                 410                 415

Gly Glu Glu Gln Arg Gln Leu Pro Glu Arg Ala Phe Arg Ala Leu Pro
            420                 425                 430

Ser Gly Ser Gly Pro Gly Glu Val Pro Thr Ser Arg Gly Leu Ser Ser
        435                 440                 445

Gly Thr Leu Pro Gly Pro Gly Asn Glu Ala Ser Arg Glu Leu Glu Ser
    450                 455                 460

Tyr Cys
465

<210> SEQ ID NO 236
<211> LENGTH: 463
<212> TYPE: PRT
<213> ORGANISM: Homo sapiens

<400> SEQUENCE: 236

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140
```

```
Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
            195                 200                 205

Ala Gln Gln His Gln Trp Asp Gly Leu Leu Ser Tyr Gln Asp Ser Leu
        210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Leu Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
290                 295                 300

Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
        355                 360                 365

Phe Val Met Asp Glu His Ala Arg Gly Thr Leu Arg Phe Ile Lys Leu
370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
        435                 440                 445

Ala Gly Ser Ser Met Tyr Thr Ala Thr Cys Gln Ala Ser Cys Ser
450                 455                 460
```

The invention claimed is:

1. A GIP analogue having the general Formula I:

(I)
(SEQ ID NO: 56)
R¹-Tyr-X2-Glu-Gly-Thr-Phe-Thr-Ser-Asp-X10-Ser-Ile-X13-Leu-X15-X16-Ψ-Ala-X19-X20-X21-Phe-X23-X24-Trp-Leu-X27-X28-X29-X30-R² wherein

R¹ is H, $C_{1-4}$ alkyl, acetyl, formyl, benzoyl, trifluoroacetyl or pGlu;
X2 is Aib;
X10 is Tyr;
X13 is Ala;
X15 is Asp;
X16 is Lys;
X19 is Gln;
X20 is Arg;
X21 is Ala;
X23 is Val;
X24 is Glu;
X27 is Leu;
X28 is Ala;
X29 is Gln;
X30 is Y1;
Y1 is Lys-Pro-Ser-Ser-Gly-Ala-Pro-Pro-Ser (SEQ ID NO: 58);

Ψ is K([19-carboxy-nonadecanoyl]-isoGlu-Peg3-Peg3); and

R² is —NH₂ or —OH;

or a pharmaceutically acceptable salt thereof.

2. A pharmaceutical composition comprising a GIP analogue according to claim 1, or a pharmaceutically acceptable salt thereof, in admixture with a carrier, wherein the composition is formulated as a liquid suitable for administration by injection or infusion, or formulated to cause slow release of said GIP analogue.

3. A method of treatment and/or prevention of diabetes or a diabetes related disorder, or obesity or an obesity related disorder, comprising administering to a subject in need thereof a GIP analogue according to claim 1, or a pharmaceutically acceptable salt thereof.

4. The method according to claim 3, wherein:
(a) the diabetes related disorder is insulin resistance, glucose intolerance, increased fasting glucose, hypoglycemia, pre-diabetes, type 1 diabetes, type 2 diabetes, gestational diabetes hypertension, dyslipidemia, bone related disorder or a combination thereof; or
(b) the diabetes related disorder is atherosclerosis, arteriosclerosis, coronary heart disease, peripheral artery disease, stroke, or a condition associated with atherogenic dyslipidemia, a blood fat disorder, elevated blood pressure, hypertension, a prothrombotic state, or a proinflammatory state; or
(c) the obesity related disorder is obesity linked inflammation, obesity linked gallbladder disease, obesity induced sleep apnea, or a condition associated with atherogenic dyslipidemia, a blood fat disorder, elevated blood pressure, hypertension, a prothrombotic state, a proinflammatory state, or a combination thereof.

5. The GIP analogue of claim 1, wherein R1 is H— and R2 is —NH₂ and the GIP analogue has the sequence of:

```
                                        (SEQ ID NO: 216)
H-Y-Aib-EGTFTSDYSIALDK-K([19-carboxynonadecanoyl]-isoGlu-Peg3-Peg3)-

AQRAFVEWLLAQKPSSGAPPPS-NH₂.
```

6. The method according to claim 4, wherein:
(a) the bone related disorder is osteoporosis;
(b) the blood fat disorder is high triglycerides, low HDL cholesterol, high LDL cholesterol, plaque buildup in artery walls, or a combination thereof.

* * * * *